(12) United States Patent
Aoyama

(10) Patent No.: US 11,694,330 B2
(45) Date of Patent: Jul. 4, 2023

(54) MEDICAL IMAGE PROCESSING APPARATUS, SYSTEM, AND METHOD

(71) Applicant: CANON MEDICAL SYSTEMS CORPORATION, Otawara (JP)

(72) Inventor: Gakuto Aoyama, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 72 days.

(21) Appl. No.: 17/349,435

(22) Filed: Jun. 16, 2021

(65) Prior Publication Data
US 2022/0012878 A1    Jan. 13, 2022

(30) Foreign Application Priority Data

Jul. 13, 2020 (JP) ................................ 2020-119732
Jun. 2, 2021 (JP) ................................ 2021-093178

(51) Int. Cl.
*G06T 7/00* (2017.01)
*G06T 11/00* (2006.01)
*A61B 6/00* (2006.01)

(52) U.S. Cl.
CPC ............ *G06T 7/0012* (2013.01); *G06T 11/00* (2013.01); *A61B 6/503* (2013.01); *A61B 6/5217* (2013.01); *G06T 2207/10081* (2013.01); *G06T 2207/30048* (2013.01); *G06T 2207/30104* (2013.01)

(58) Field of Classification Search
None
See application file for complete search history.

(56) References Cited

U.S. PATENT DOCUMENTS

2017/0245821 A1* 8/2017 Itu ........................... G06V 10/42
2018/0092615 A1* 4/2018 Sakaguchi ............. A61B 6/504
2020/0126219 A1* 4/2020 Wang ....................... A61B 8/06

FOREIGN PATENT DOCUMENTS

| JP | 2011-062358 A | 3/2011 |
| JP | 2016-533815 A | 11/2016 |
| JP | 2020-51 8362 A | 6/2020 |
| WO | WO 2015/023495 A1 | 2/2015 |

* cited by examiner

*Primary Examiner* — Yanna Wu
(74) *Attorney, Agent, or Firm* — Oblon, McClelland, Maier & Neustadt, L.L.P.

(57) ABSTRACT

A medical image processing apparatus according to an embodiment includes processing circuitry. The processing circuitry is configured to extract a degree of a disease related to the heart from a medical image; and display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated on the basis of the medical image.

39 Claims, 23 Drawing Sheets

EXPRESSED WITH COLORS

EXPRESSED WITH TEXTURES

EXPRESSED WITH QUANTITY AND DIRECTIONS OF ARROWS

WHEN NOT ACTIVE

WHEN FFR IS ACTIVE

WHEN WSS IS ACTIVE

FIG.8
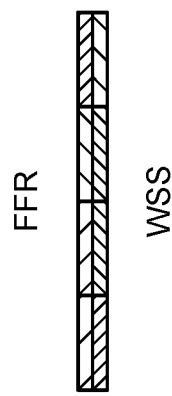

FIG.9
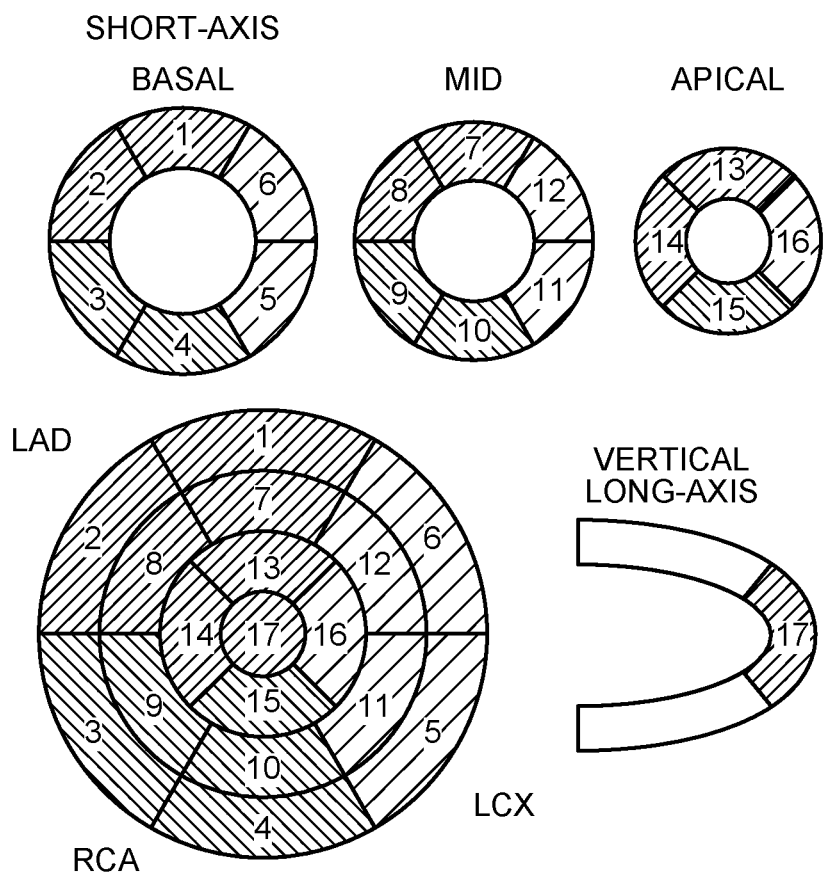
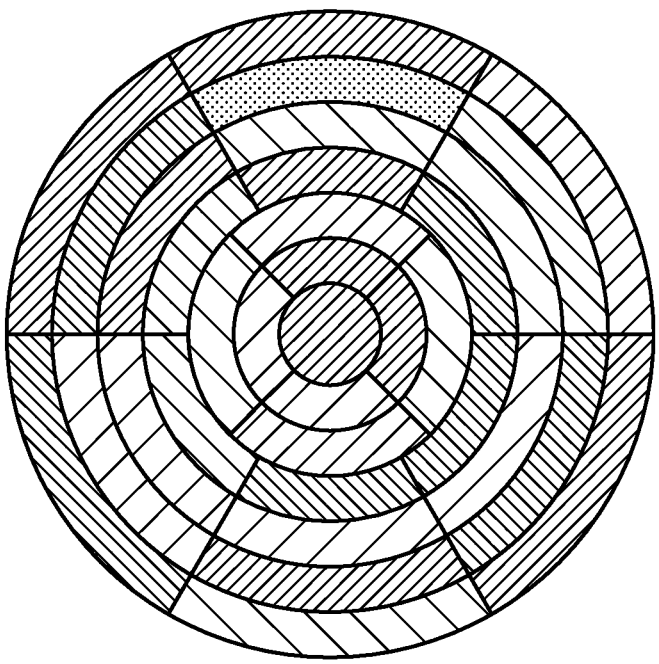

POST-TREATMENT
PREDICTED WSS

PLAQUE

MEDICAL IMAGE PROCESSING APPARATUS, SYSTEM, AND METHOD

CROSS-REFERENCE TO RELATED APPLICATIONS

This application is based upon and claims the benefit of priority from Japanese Patent Application No. 2020-119732, filed on Jul. 13, 2020 and Japanese Patent Application No. 2021-093178, filed on Jun. 2, 2021; the entire contents of which are incorporated herein by reference.

FIELD

Embodiments described herein relate generally to an apparatus, a system, and a method for medical image processing.

BACKGROUND

As a technique for assisting diagnosing and treatment planning processes or the like related to cardiac diseases, a technique is conventionally known by which, on the basis of a medical image related to blood vessels of the heart of a subject, various types of information related to blood flows of the blood vessels are calculated and presented. For example, a technique is known by which, as one type of information related to the blood flows, Wall Shear Stress (WSS) in various positions in the blood vessels is calculated and displayed.

Generally speaking, when the diagnosing and treatment planning processes or the like are performed by using the technique described above, users such as medical doctors make comprehensive judgment by integrating various types of information together in addition to the WSS values. However, when multiple types of information are presented without any restriction, the work to obtain or understand the information would be complicated and thus increase trouble of the users.

BRIEF DESCRIPTION OF THE DRAWINGS

FIG. 8 is a drawing illustrating an example of information display performed by a display controlling function according to a fourth modification example of the first embodiment;

FIG. 9 is a drawing illustrating another example of the information display performed by the display controlling function according to the fourth modification example of the first embodiment;

DETAILED DESCRIPTION

A medical image processing apparatus according to an embodiment includes an extracting unit and a display controlling unit. The extracting unit is configured to extract a degree of a disease related to the heart from a medical image. The display controlling unit is configured to display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated on the basis of the medical image.

Exemplary embodiments of an apparatus, a system, and a method for medical image processing will be explained in detail below, with reference to the accompanying drawings.

First Embodiment

Figure 1:
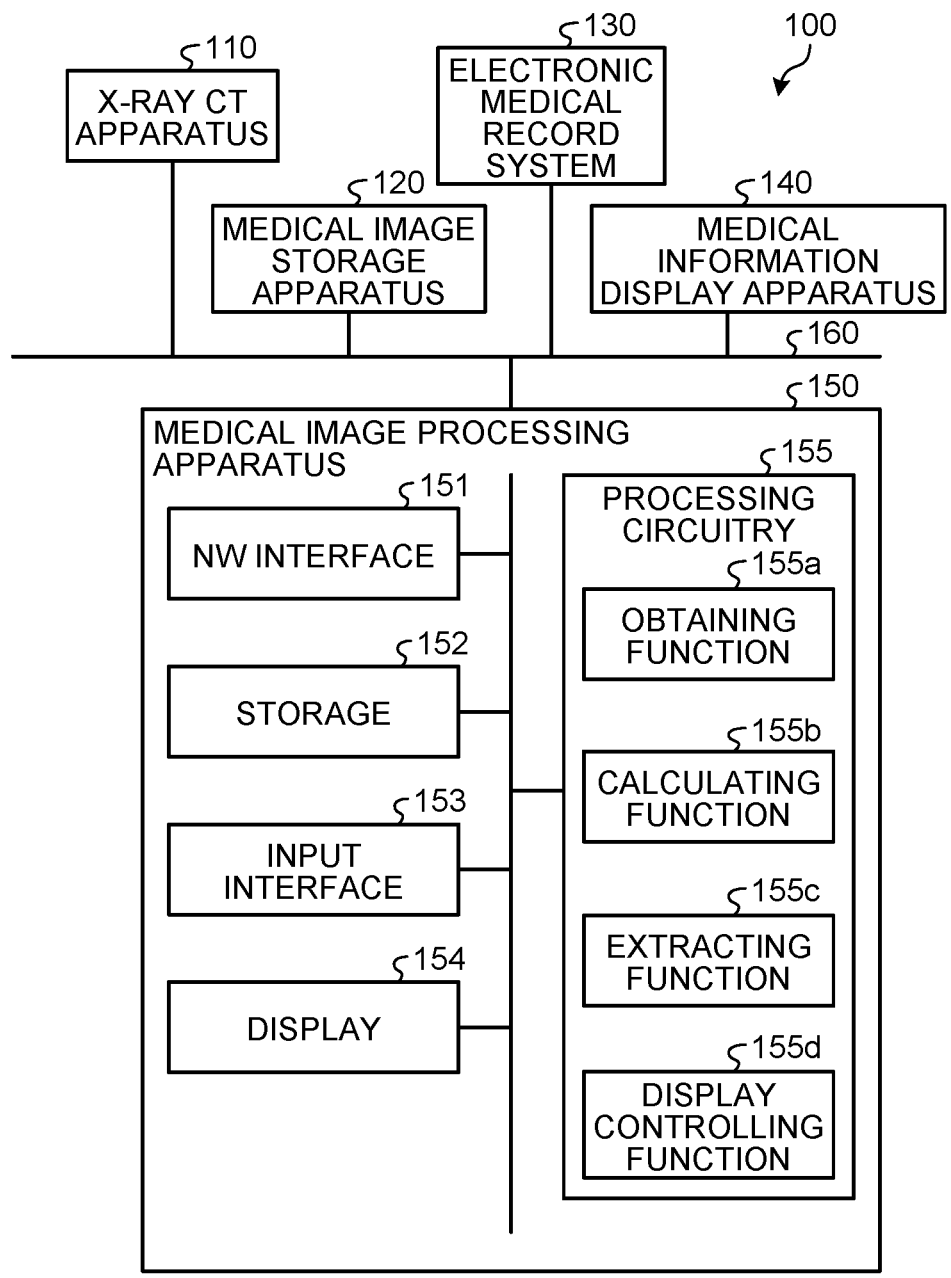
FIG. 1 is a diagram illustrating an exemplary configuration of a medical image processing system and a medical image processing apparatus according to a first embodiment.

FIG. 1 is a diagram illustrating an exemplary configuration of a medical image processing system and a medical image processing apparatus according to a first embodiment.

For example, as illustrated in FIG. 1, a medical image processing system 100 according to the present embodiment includes an X-ray Computed Tomography (CT) apparatus 110, a medical image storage apparatus 120, an electronic medical record system 130, a medical information display apparatus 140, and a medical image processing apparatus 150. In the present example, the apparatuses and the system are communicably connected via a network 160.

In addition to the X-ray CT apparatus 110, the medical image processing system 100 may further include one or more other medical image diagnosis apparatuses such as a Magnetic Resonance Imaging (MRI) apparatus, an ultrasound diagnosis apparatus, a Positron Emission Tomography (PET) apparatus, a Single Photon Emission Computed Tomography (SPECT) apparatus, and/or the like. Further, in addition to the electronic medical record system 130, the medical image processing system 100 may further include one or more other systems such as a Hospital Information System (HIS), a Radiology Information System (RIS), and/or the like.

The X-ray CT apparatus 110 is configured to generate a CT image related to a subject. More specifically, the X-ray CT apparatus 110 is configured to acquire projection data expressing a distribution of X-rays that have passed through the subject, by moving an X-ray tube and an X-ray detector to turn on a circular trajectory around the subject. Further, on the basis of the acquired projection data, the X-ray CT apparatus 110 generates the CT image.

The medical image storage apparatus 120 is configured to store therein various types of images related to the subject. More specifically, the medical image storage apparatus 120 is configured to obtain the CT image from the X-ray CT apparatus 110 via the network 160 and to save and store the CT image in a storage therein. For example, the medical image storage apparatus 120 may be realized by using a computer device such as a server or a workstation. Alternatively, for example, the medical image storage apparatus 120 may be realized by using a Picture Archiving and Communication System (PACS) or the like so as to store the CT image therein in a format compliant with Digital Imaging and Communications in Medicine (DICOM).

The electronic medical record system 130 is configured to store therein various types of diagnosis/treatment data related to diagnosis/treatment records and patient information of the subject. More specifically, the electronic medical record system 130 is configured to generate the diagnosis/treatment data related to the subject or to obtain the diagnosis data from another apparatus via the network 160, and to further save and store the diagnosis/treatment data in a storage therein. For example, the electronic medical record system 130 is realized by using a computer device such as a server or a workstation.

The medical information display apparatus 140 is configured to display various types of medical information related to the subject. More specifically, the medical information display apparatus 140 is configured to obtain the medical information such as the CT image or processing results of image processing from the medical image processing apparatus 150 via the network 160 and to display the medical information on a display therein. For example, the medical information display apparatus 140 is realized by using a computer device such as a workstation, a personal computer, or a tablet terminal.

The medical image processing apparatus 150 is configured to perform various types of image processing processes related to the subject. More specifically, the medical image processing apparatus 150 is configured to obtain the CT image from either the X-ray CT apparatus 110 or the medical image storage apparatus 120 via the network 160, to obtain the diagnosis/treatment data from the electronic medical record system 130, and to perform the various types of image processing processes by using the CT image and the diagnosis/treatment data. For example, the medical image processing apparatus 150 is realized by using a computer device such as a server or a workstation.

For example, the medical image processing apparatus 150 includes a network (NW) interface 151, a storage 152, an input interface 153, a display 154, and processing circuitry 155.

The NW interface 151 is configured to control transfer and communication of various types of data transmitted and received between the medical image processing apparatus 150 and the other apparatuses connected via the network 160. More specifically, the NW interface 151 is connected to the processing circuitry 155 and is configured to transmit the data received from the other apparatuses to the processing circuitry 155 and to transmit the data received from the processing circuitry 155 to any of the other apparatuses. For example, the NW interface 151 is realized by using a network card, a network adaptor, or a Network Interface Controller (NIC).

The storage 152 is configured to store therein various types of data and various types of programs. More specifically, the storage 152 is connected to the processing circuitry 155 and is configured to store the data received from the processing circuitry 155 therein and to read and transmit any of the stored data to the processing circuitry 155. For example, the storage 152 is realized by using a semiconductor memory element such as a Random Access Memory (RAM) or a flash memory, or a hard disk, an optical disk, or the like.

The input interface 153 is configured to receive operations to input various types of instructions and various types of information from a user. More specifically, the input interface 153 is connected to the processing circuitry 155 and is configured to convert the input operations received from the user into electrical signals and to transmit the electrical signals to the processing circuitry 155. For example, the input interface 153 is realized by using a trackball, a switch button, a mouse, a keyboard, a touchpad on which input operations can be performed by touching an operation surface thereof, a touch screen in which a display screen and a touchpad are integrally formed, a contactless input interface using an optical sensor, an audio input interface, and/or the like. In the present disclosure, the input interface 153 does not necessarily have to include one or more physical operation component parts such as a mouse, a keyboard, and/or the like. Possible examples of the input interface 153 include, for instance, electrical signal processing circuitry configured to receive electrical signals corresponding to input operations from an external input device provided separately from the apparatus and to transmit the electrical signals to a control circuit.

The display 154 is configured to display various types of information and various types of data. More specifically, the display 154 is connected to the processing circuitry 155 and is configured to display the various types of information and the various types of data received from the processing circuitry 155. For example, the display 154 is realized by using a liquid crystal monitor, a Cathode Ray Tube (CRT) monitor, a touch panel, or the like.

The processing circuitry 155 is configured to control the entirety of the medical image processing apparatus 150. For example, the processing circuitry 155 is configured to perform various types of processes in accordance with the input operations received from the user via the input interface 153. Further, for example, the processing circuitry 155 is configured to receive data transmitted from any of the other apparatuses through the NW interface 151 and to store the received data into the storage 152. Further, for example, the processing circuitry 155 is configured to transmit data received from the storage 152 to the NW interface 151, so as to transmit the data to any of the other apparatuses. Further, for example, the processing circuitry 155 is configured to cause the display 154 to display any of the data received from the storage 152.

The exemplary configuration of the medical image processing system 100 and the medical image processing apparatus 150 according to the present embodiment has thus been explained. For example, the medical image processing system 100 and the medical image processing apparatus 150 according to the present embodiment are installed in a medical facility such as a hospital or a clinic and are configured to assist diagnosing and treatment planning processes or the like related to cardiac diseases and performed by the user such as a medical doctor.

More specifically, on the basis of a medical image, the medical image processing apparatus 150 is configured to calculate and present various types of information related to blood flows of pertinent blood vessels. For example, as one type of information related to the blood flows, the medical image processing apparatus 150 is configured to calculate and display WSS in various positions in the blood vessel.

Generally speaking, when a diagnosing process is performed, a treatment plan is determined, or the like by using the technique described above, users such as medical doctors make comprehensive judgment by integrating various types of information together in addition to the WSS values. However, when multiple types of information are presented without any restriction, the work to obtain or understand the information would be complicated and thus increase trouble of the users.

For this reason, the medical image processing apparatus 150 according to the present embodiment is configured to be able to reduce the trouble of the user at the time of performing a diagnosis process, determining a treatment plan, or the like, in relation to cardiac diseases.

More specifically, as the information related to the blood flows of the blood vessels and calculated on the basis of the medical image, the medical image processing apparatus 150 is configured to display a first index value related to the blood vessels and calculated from one of blood pressure and the blood flows and WSS serving as a second index value related to the blood vessels. Further, on the basis of information about the subject, the medical image processing apparatus 150 is configured to switch the display between the first index value and the WSS. In this situation, the first index value is an index value of a different type from the wall shear stress serving as the second index value.

In this situation, the medical image processing apparatus 150 is configured to extract a degree of a disease related to the heart, from the medical image. Further, as the information related to the blood flows of the blood vessels and calculated on the basis of the medical image, the medical image processing apparatus 150 is configured to display the first index value related to the blood vessels and calculated from one of blood pressure and the blood flows when the degree of the disease related to the heart is high and is configured to display the WSS serving as the second index value related to the blood vessels when the degree of the disease related to the heart is low.

With this arrangement, it is possible to appropriately switch the display between the WSS and the other index value calculated from the medical image, in accordance with the state of the subject. Consequently, it is possible to reduce the trouble of the user at the time of performing a diagnosing process, making a treatment plan, or the like in relation to cardiac diseases.

Next, details of the medical image processing apparatus 150 configured as described above will be explained. In the following sections, an example will be explained in which a coronary artery CT image is used as the medical image, whereas Fractional Flow Reserve (FFR) is displayed as the first index value related to the blood vessels and calculated from one of blood pressure and the blood flows.

For example, as illustrated in FIG. 1, in the present embodiment, the processing circuitry 155 of the medical image processing apparatus 150 includes an obtaining function 155a, a calculating function 155b, an extracting function 155c, and a display controlling function 155d. In this situation, the extracting function 155c is an example of the extracting unit. Further, the display controlling function 155d is an example of the display controlling unit.

Via the NW interface 151, the obtaining function 155a is configured to obtain the coronary artery CT image of the subject from either the X-ray CT apparatus 110 or the medical image storage apparatus 120.

The calculating function 155b is configured to calculate the FFR and the WSS on the basis of the coronary artery CT image of the subject obtained by the obtaining function 155a.

For example, from the coronary artery CT image of the subject, the calculating function 155b calculates the FFR and the WSS in various positions in the coronary arteries, by implementing a known method using Computational Fluid Dynamics (CFD), machine learning, or the like.

The extracting function 155c is configured to extract a degree of a disease related to the heart, from the coronary artery CT image of the subject obtained by the obtaining function 155a. In this situation, the "degree of the disease" includes not only the state in which the disease is present, but also the state in which the disease is absent. In other words, the "degree of the disease" is able to indicate not only the degree of the disease when the disease is present, but also that the disease is absent.

For example, as the degree of the disease related to the heart, the extracting function 155c extracts a degree of a coronary artery disease, from the coronary artery CT image of the subject obtained by the obtaining function 155a.

More specifically, the extracting function 155c extracts a disease degree indicating the degree of the coronary artery disease, by analyzing the coronary artery CT image of the subject. Further, for example, as the disease degree indicating the degree of the coronary artery disease, the extracting function 155c extracts a probability of the presence (hereinafter, "presence probability") of myocardial ischemia. In this situation, for example, the extracting function 155c may extract the presence probability on the basis of a distribution of CT values in myocardial regions or may extract the presence probability by using a discriminator that has learned, in advance, characteristics of images in which myocardial ischemia is present and images in which myocardial ischemia is not present through the machine learning technology.

In the present embodiment, the disease degree extracted by the extracting function 155c and indicating the degree of the coronary artery disease does not necessarily have to be the presence probability of myocardial ischemia. The disease degree may be expressed with any value, as long as the value is calculated by the user for the purpose of controlling the display of the FFR and the WSS as described below. For example, the extracting function 155c may directly assign a value serving as a disease degree on the basis of a result of a diagnosing process separately performed for the subject by the user such as a medical doctor or may extract, as a disease degree, a value indicating seriousness of the myocardial ischemia on the basis of a perfusion index obtained from the coronary artery CT image.

As the information related to the blood flows of the coronary arteries and calculated on the basis of the coronary artery CT image of the subject obtained by the obtaining function 155a, the display controlling function 155d is configured to cause display 154 to display the FFR and the WSS calculated by the calculating function 155b. Further, on the basis of the information about the subject, the display controlling function 155d is configured to switch the display between the FFR and the WSS.

In this situation, as the information related to the blood flows of the coronary arteries and calculated on the basis of the coronary artery CT image of the subject obtained by the obtaining function 155a, the display controlling function 155d is configured to display the FFR when the degree of the coronary artery disease extracted by the extracting function 155c is high and is configured to display the WSS when the degree of the coronary artery disease is low.

More specifically, when the disease degree indicating the degree of the coronary artery disease is higher than a first threshold value, the display controlling function 155d is configured to display the FFR. In another example, when the disease degree indicating the degree of the coronary artery disease is lower than a second threshold value smaller than the first threshold value, the display controlling function 155d is configured to display the WSS. In yet another example, when the disease degree indicating the degree of the coronary artery disease falls between the first threshold value and the second threshold value, the display controlling function 155d is configured to display the FFR and the WSS.

Figure 2:
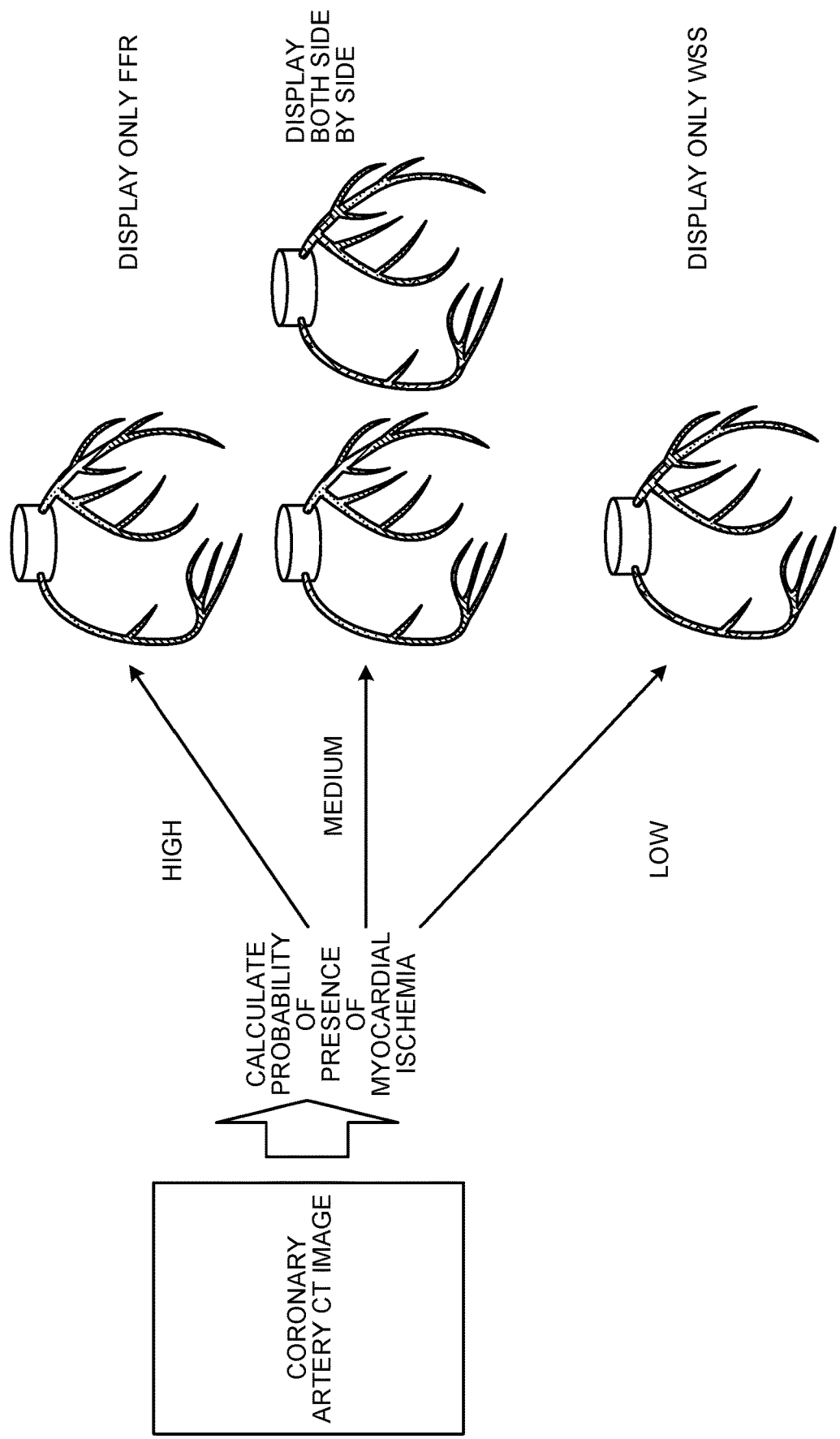
FIG. 2 is a drawing illustrating an example of information display performed by a display controlling function according to the first embodiment.

FIG. 2 is a drawing illustrating an example of the information display performed by the display controlling function 155d according to the first embodiment.

For example, as illustrated in FIG. 2, on the basis of the presence probability of myocardial ischemia extracted by the extracting function 155c, the display controlling function 155d determines the type of information to be displayed on the display 154. In this situation, for example, when the presence probability of myocardial ischemia is higher than the first threshold value set in advance (presence probability: high), the display controlling function 155d determines the type of information to be displayed as the FFR. As another example, when the presence probability of myocardial ischemia is lower than the second threshold value (<the first threshold value) set in advance (presence probability: low), the display controlling function 155d determines the type of information to be displayed as the WSS. As yet another example, when the presence probability of myocardial ischemia falls in the range from the first threshold value to the second threshold value (presence probability: medium), the display controlling function 155d determines the type of information to be displayed as both the FFR and the WSS.

In other words, when the presence probability of myocardial ischemia is high, because it is expected that treatment applicability needs to be assessed and a treatment plan needs to be made urgently, the display controlling function 155d is configured to determine to display only the information of the FFR, which is information necessary for the urgent decision. In contrast, when the presence probability of myocardial ischemia is low, because it is expected that a long-term treatment plan needs to be made, the display controlling function 155d is configured to determine to display only the information of the WSS, which is information necessary for the long-term decision.

Further, the display controlling function 155d is configured to cause the display 154 to display the determined type of information. For example, at first, by three-dimensionally reconstructing a blood vessel region of the coronary arteries in the coronary artery CT image, the display controlling function 155d generates a three-dimensional image (e.g., a Volume Rendering [VR] image or a Surface Rendering [SF] image) of the coronary arteries. Further, on the basis of a maximum value and a minimum value among the FFR values and the WSS values in the various positions in the coronary arteries, the display controlling function 155d is configured to identify a possible range of the FFR values and the WSS values and to further set a color array (a color lookup table) on the basis of the identified ranges. Subsequently, with respect to the FFR and the WSS, the display controlling function 155d generates color map images by assigning a color corresponding to each of the different positions in the three-dimensional image of the coronary arteries. After that, when the type of information to be displayed is determined as the FFR, the display controlling function 155d causes the display 154 to display the color map image of the FFR. In another example, when the type of information to be displayed is determined as the WSS, the display controlling function 155d causes the display 154 to display the color map image of the WSS. In yet another example, when the type of information to be displayed is determined as both the FFR and the WSS, the display controlling function 155d causes the display 154 to display the color maps of the FFR and the WSS arranged side by side.

In the present embodiment, the display mode of the pieces of information displayed by the display controlling function 155d does not necessarily have to be color map images. It is acceptable to use any display mode, as long as the user is able to correctly recognize the pieces of information. For example, the display controlling function 155d may generate images by setting an array of patterns or textures on the basis of the identified possible ranges of the FFR values and the WSS values and further assigning a corresponding pattern or texture to each of the different positions in the three-dimensional image of the coronary arteries, with respect to the FFR and the WSS. Alternatively, for example, the display controlling function 155d may allow the user to arbitrarily set a display mode of each of the pieces of information, by using a user interface realized with the input interface 153 and the display 154. Further, for example, when displaying both the FFR and the WSS, the display controlling function 155d may cause the two images to be displayed in conjunction with each other by calculating corresponding points between the two images or may automatically rotate the display by using cine display or the like. In another example, the display controlling function 155d may display a moving picture by reconstructing the images as the moving picture on the basis of a rotation speed or an angle set in advance.

The processing functions included in the processing circuitry 155 have thus been explained. In this situation, for example, the processing circuitry 155 is realized by using a processor. In that situation, the processing function described above are stored in the storage 152 in the form of computer-executable programs. Further, the processing circuitry 155 realizes the functions corresponding to the programs, by reading and executing the programs stored in the storage 152. In other words, when having read the programs, the processing circuitry 155 has the processing functions illustrated in FIG. 1.

Alternatively, the processing circuitry 155 may be structured by combining together a plurality of independent processors, so that the processing functions are realized as a result of the processors executing the programs. Further, the processing functions included in the processing circuitry 155 may be realized as being distributed among or integrated together in one or more pieces of processing circuitry, as appropriate. Further, the processing functions included in the processing circuitry 155 may be realized with a combination of hardware (e.g., circuits) and software. Further, although the example was explained above in which the programs corresponding to the processing functions are stored in the single storage (i.e., the storage 152), possible embodiments are not limited to this example. For instance, the programs corresponding to the processing functions may be stored in a plurality of storages in a distributed manner, so that the processing circuitry 155 reads and executes the programs from the storages.

Figure 3:
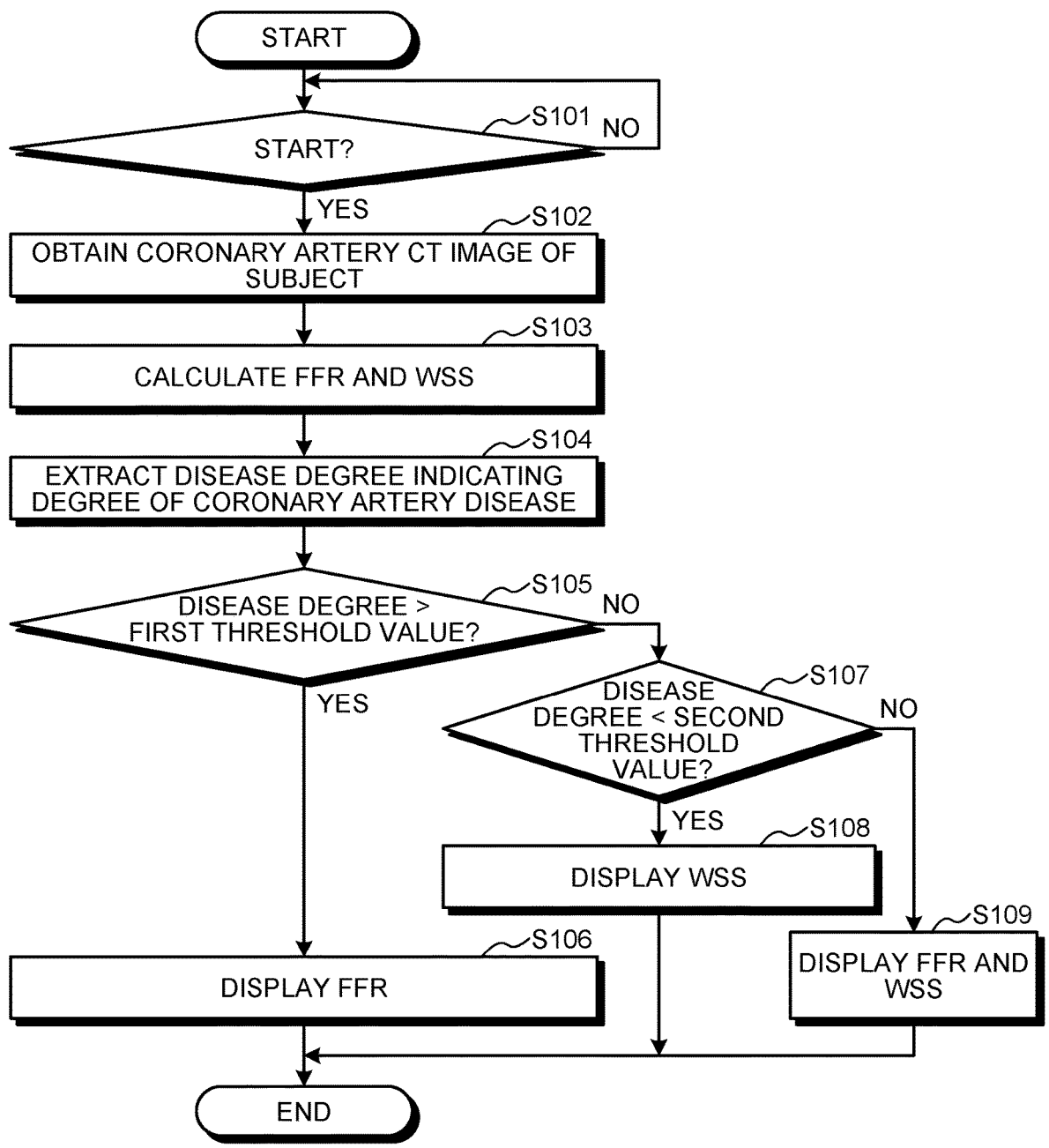
FIG. 3 is a flowchart illustrating a processing procedure of a process performed by processing functions included in processing circuitry of the medical image processing apparatus according to the first embodiment.

FIG. 3 is a flowchart illustrating a processing procedure of a process performed by the processing functions included in the processing circuitry 155 of the medical image processing apparatus 150 according to the first embodiment.

For example, as illustrated in FIG. 3, in the present embodiment, upon receipt of an instruction to start the process from the user via the input interface 153 (step S101: Yes), the obtaining function 155a obtains a coronary artery CT image of the subject from either the X-ray CT apparatus 110 or the medical image storage apparatus 120 (step S102). For example, this process is realized as a result of the processing circuitry 155 invoking and executing the program corresponding to the obtaining function 155a from the storage 152.

Subsequently, on the basis of the coronary artery CT image of the subject obtained by the obtaining function 155a, the calculating function 155b calculates FFR and WSS (step S103). For example, this process is realized as a result of the processing circuitry 155 invoking and executing the program corresponding to the calculating function 155b from the storage 152.

After that, the extracting function 155c extracts the disease degree indicating a degree of a coronary artery disease from the coronary artery CT image of the subject obtained by the obtaining function 155a (step S104). For example, this process is realized as a result of the processing circuitry 155 invoking and executing the program corresponding to the extracting function 155c from the storage 152.

Subsequently, when the disease degree indicating the degree of the coronary artery disease is higher than the first threshold value (step S105: Yes), the display controlling function 155d displays the FFR calculated by the calculating function 155b (step S106). In another example, when the disease degree indicating the degree of the coronary artery disease is lower than the second threshold value smaller than the first threshold value (step S105: No; step S107: Yes), the display controlling function 155d displays the WSS calculated by the calculating function 155b (step S108). In yet another example, when the disease degree indicating the degree of the coronary artery disease falls between the first threshold value and the second threshold value (step S107: No), the display controlling function 155d displays the FFR and the WSS calculated by the calculating function 155b (step S109). For example, this process is realized as a result of the processing circuitry 155 invoking and executing the program corresponding to the display controlling function 155d from the storage 152.

As described above, in the first embodiment, the medical image processing apparatus 150 is configured to switch the display between the WSS and the FFR calculated from the coronary artery CT image in accordance with the state of the subject. As a result, when a diagnosing process is performed or a treatment plan is made in relation to cardiac diseases, it is possible to automatically display the WSS and the FFR with appropriate timing. Consequently, according to the first embodiment, it is possible to reduce the trouble of the user at the time of performing the diagnosing process, making the treatment plan, or the like in relation to cardiac diseases.

A First Modification Example of the First Embodiment

In the first embodiment described above, the example was explained in which the display is switched between the FFR and the WSS in accordance with the degree of the coronary artery disease; however, possible embodiments are not limited to this example.

Generally speaking, it is known that examples of FFR values include one-dimensional FFR (hereinafter, "1D-

FFR") and three-dimensional FFR (hereinafter, "3D-FFR"), depending on the calculation method thereof. Similarly, it is known that examples of WSS values include one-dimensional WSS (hereinafter, "1D-WSS") and three-dimensional WSS (hereinafter, "3D-WSS"), depending on the calculation method thereof. More specifically, for the 3D-FFR, a method is implemented to calculate FFR in each of various positions in a blood vessel. In contrast, for the 1D-FFR, a method is implemented to calculate FFR in each of various cross-sectional positions in a blood vessel, while using the centerline of the blood vessel as a reference. Similarly, for the 3D-WSS, a method is implemented to calculate WSS in each of various positions in a blood vessel. In contrast, for the 1D-WSS, a method is implemented to calculate WSS in each of various cross-sectional positions in a blood vessel, while using the centerline of the blood vessel as a reference.

In this regard, because the 3D-FFR and the 3D-WSS are obtained by calculating the WSS and the FFR in the local positions, there is an advantage where it is possible to provide more accurate information. However, there is also a disadvantage where the calculation cost is higher in terms of calculation time, processing performed by a computer, how much volume of a storage region is used, and the like. In contrast, the 1D-FFR and the 1D-WSS have a disadvantage where the accuracy of the information is lower than that of the 3D-FFR and the 3D-WSS. However, there is an advantage where the calculation cost is lower in terms of calculation time, processing performed by a computer, how much volume of a storage region is used, and the like.

Accordingly, as a first modification example of the first embodiment, for instance, the medical image processing apparatus 150 may be configured to switch the display between one or both of the 1D-FFR and the 1D-WSS and one or both of the 3D-FFR and the 3D-WSS, in accordance with the disease degree indicating the degree of a coronary artery disease.

More specifically, on the basis of the coronary artery CT image of the subject, the calculating function 155b calculates the 1D-FFR and the 1D-WSS, as well as the 3D-FFR and the 3D-WSS, as information related to the blood flows of the coronary arteries.

After that, when the disease degree indicating the degree of the coronary artery disease is high, the display controlling function 155d displays one or both of the 1D-FFR and the 1D-WSS calculated by the calculating function 155b. On the contrary, when the disease degree indicating the degree of the coronary artery disease is low, the display controlling function 155d displays one or both of the 3D-FFR and the 3D-WSS calculated by the calculating function 155b.

Figure 4:
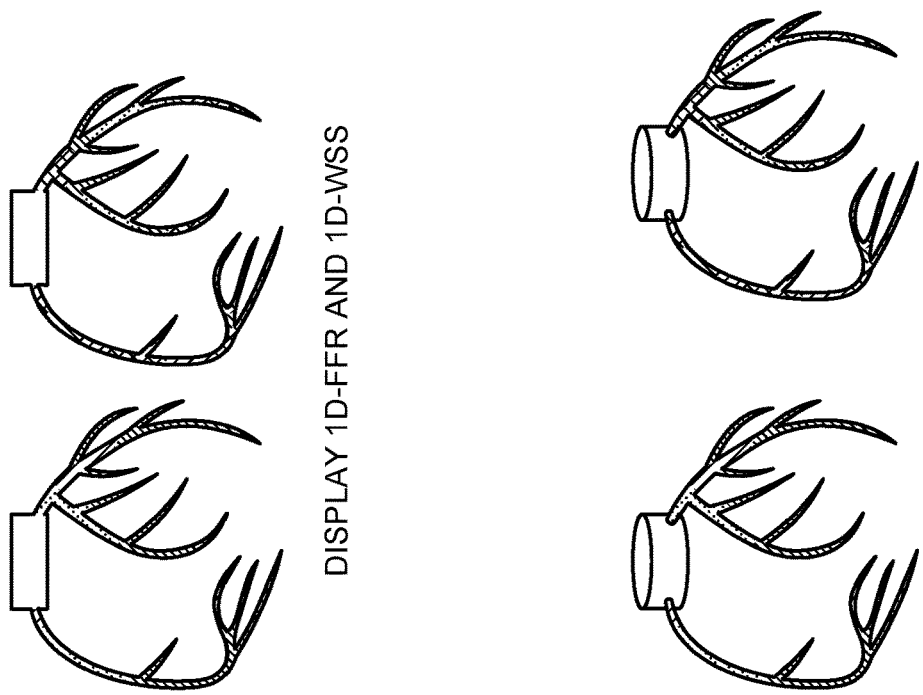
FIG. 4 is a drawing illustrating an example of information display performed by a display controlling function according to a first modification example of the first embodiment.

FIG. 4 is a drawing illustrating an example of the information display performed by the display controlling function 155d according to the first modification example of the first embodiment.

For example, as illustrated in FIG. 4, the display controlling function 155d determines the type of information to be displayed on the display 154, on the basis of the presence probability of myocardial ischemia extracted by the extracting function 155c. In this situation, for example, when the presence probability of myocardial ischemia is higher than the threshold value, the display controlling function 155d determines the type of information to be displayed as the 1D-FFR and the 1D-WSS. In contrast, when the presence probability of myocardial ischemia is lower than the threshold value, the display controlling function 155d determines the type of information to be displayed as the 3D-FFR and the 3D-WSS.

In other words, when the presence probability of myocardial ischemia is high, because it is expected that treatment applicability needs to be assessed and a treatment plan needs to be made urgently while there is little time to spare, the display controlling function 155d is configured to determine to display the 1D-FFR and the 1D-WSS, which can be calculated in a shorter period of time. In contrast, when the presence probability of myocardial ischemia is low, because it is expected that there is some time to spare, the display controlling function 155d is configured to determine to display the 3D-FFR and the 3D-WSS, which are more accurate information.

Possible examples of displaying the FFR and the WSS according to the present modification example are not limited to this example. For instance, when the presence probability of myocardial ischemia is higher than the threshold value, the display controlling function 155d may determine the type of information to be displayed as one selected from between the 1D-FFR and the 1D-WSS. Also, when the presence probability of myocardial ischemia is lower than the threshold value, the display controlling function 155d may determine the type of information to be displayed as one selected from between the 3D-FFR and the 3D-WSS. In each of these situations, for example, the display controlling function 155d determines to display information designated by the user from between the FFR and the WSS. Alternatively, for example, the display controlling function 155d may further prepare another threshold value larger than the abovementioned threshold value, so that when the presence probability of myocardial ischemia is higher than the additionally-prepared threshold value, the display controlling function 155d determines the type of information to be displayed as only the 1D-FFR.

A Second Modification Example of the First Embodiment

In the first embodiment described above, the example was explained in which the type of information to be displayed is changed in accordance with the degree of the coronary artery disease; however, possible embodiments are not limited to this example.

For instance, as a second modification example of the first embodiment, the medical image processing apparatus 150 may be configured to change the size of a display region of the displayed information in accordance with a degree of a coronary artery disease.

More specifically, the display controlling function 155d simultaneously displays the FFR and the WSS calculated by the calculating function 155b. Further, the display controlling function 155d makes the display region of the FFR larger than the display region of the WSS when the disease degree indicating the degree of the coronary artery disease is high and makes the display region of the WSS larger than the display region of the FFR when the disease degree indicating the degree of the coronary artery disease is low.

Figure 5:
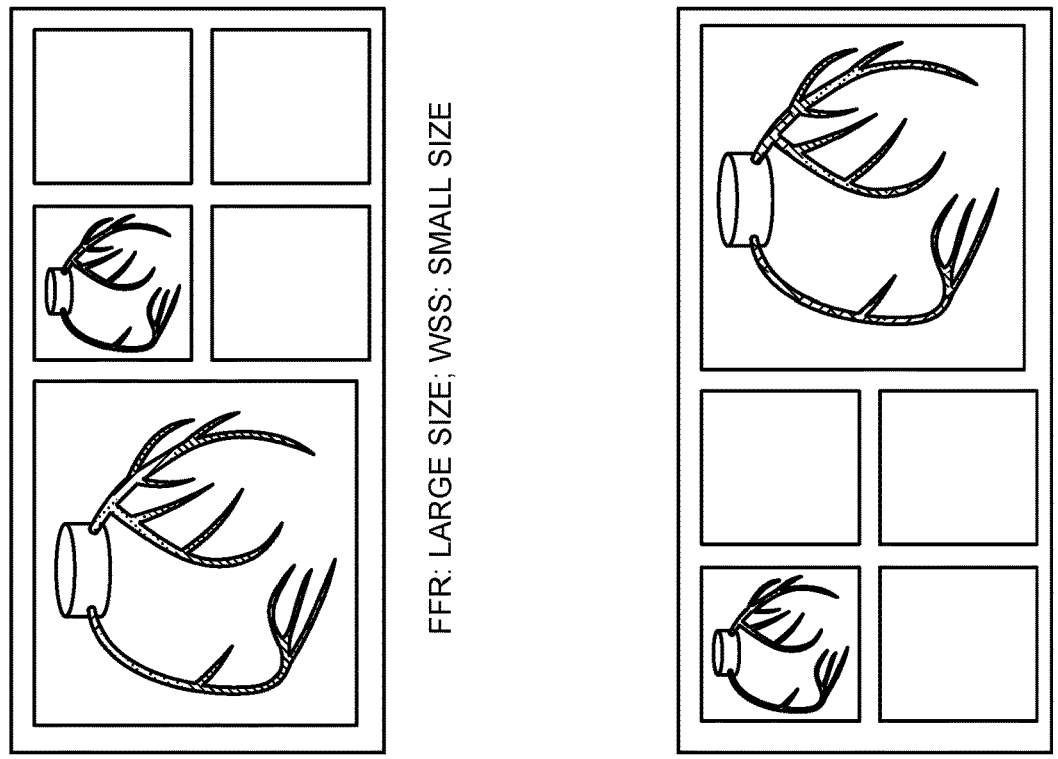
FIG. 5 is a drawing illustrating an example of information display performed by a display controlling function according to a second modification example of the first embodiment.

FIG. 5 is a drawing illustrating an example of the information display performed by the display controlling function 155d according to the second modification example of the first embodiment.

For example, as illustrated in FIG. 5, on the basis of the presence probability of myocardial ischemia extracted by the extracting function 155c, the display controlling function 155d determines the type of information to be displayed on the display 154. In this situation, for example, when the presence probability of myocardial ischemia is high, the display controlling function 155d determines to enlarge the display size of the color map image of the FFR and to reduce the display size of the color map image of the WSS. On the contrary, when the presence probability of myocardial ischemia is low, the display controlling function 155d determines to reduce the display size of the color map image of the FFR and to enlarge the display size of the color map image of the WSS.

Possible examples of displaying the FFR and the WSS according to the present modification example are not limited to the configuration described above. For instance, instead of changing the sizes of the display regions between the FFR and the WSS, the display controlling function 155d may change display colors, levels of transparency, or display positions of the display regions. For example, the display controlling function 155d may display the FFR and the WSS arranged side by side in the left-and-right direction and may determine to display the FFR on the left side when the presence probability of myocardial ischemia is high and to display the WSS on the left side when the presence probability of myocardial ischemia is low.

A Third Modification Example of the First Embodiment

Further, in the first embodiment described above, the example was explained in which the FFR and the WSS are displayed in the color map images on the basis of the color array (the color lookup table); however, possible embodiments are not limited to this example.

For instance, when the FFR and the WSS are displayed in the color maps on the basis of mutually the same color array, the generated images may look extremely similar to each other, and there is a possibility that the user may mistake one of the FFR and the WSS for the other.

To cope with this situation, for example, as a third modification example of the first embodiment, the medical image processing apparatus 150 may be configured to display the FFR and the WSS by using mutually-different display modes.

More specifically, the display controlling function 155d may be configured to display the FFR and the WSS calculated by the calculating function 155b in the mutually-different display modes.

Figure 6:
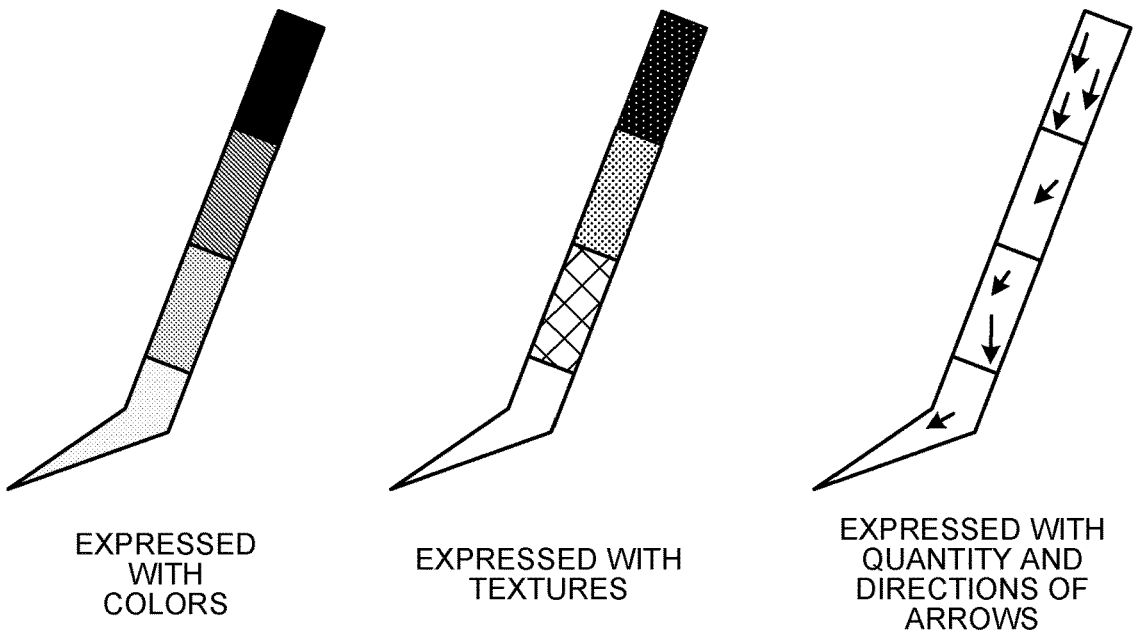
FIG. 6 is a drawing illustrating an example of information display performed by a display controlling function according to a third modification example of the first embodiment.
Figure 7:
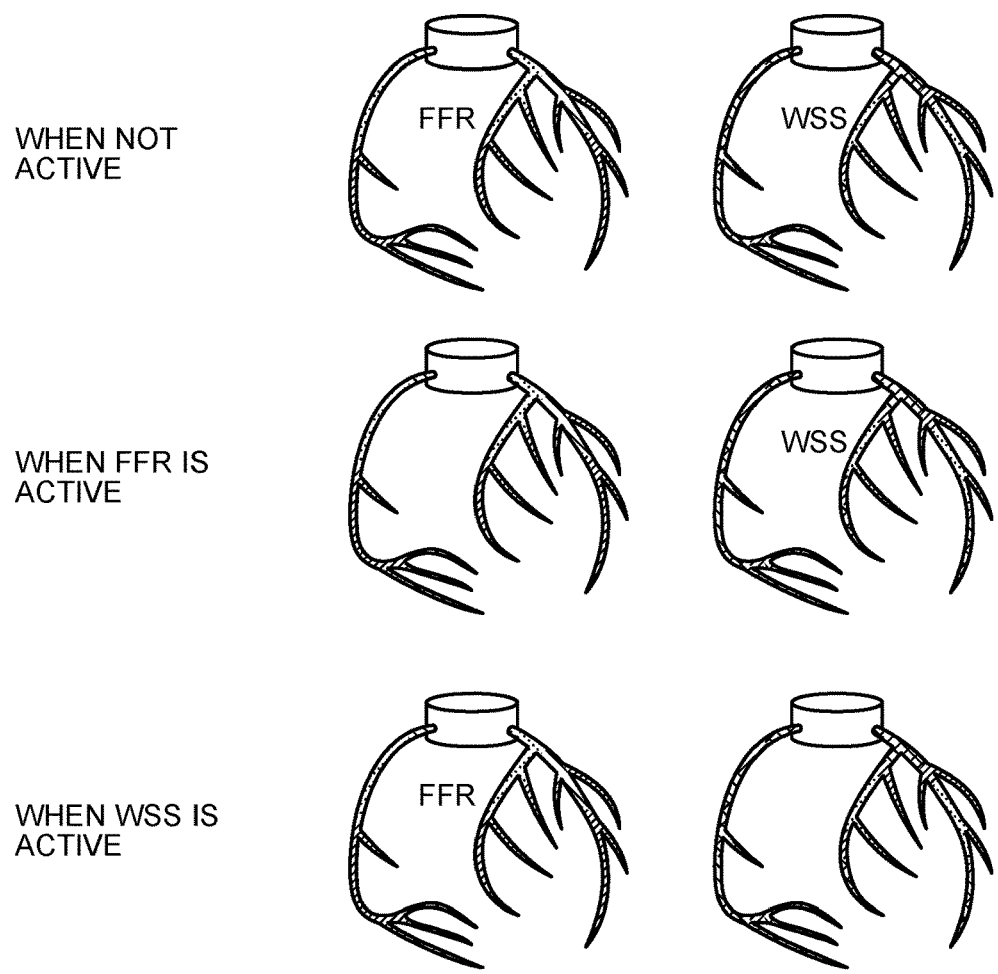
FIG. 7 is a drawing illustrating another example of the information display performed by the display controlling function according to the third modification example of the first embodiment.

FIGS. 6 and 7 are drawings illustrating examples of the information display performed by the display controlling function 155d according to the third modification example of the first embodiment.

For example, as illustrated in the left and the middle sections of FIG. 6, when simultaneously displaying an FFR image and a WSS image, the display controlling function 155d may display one of the two by using a color map image in which colors are assigned ("expressed with colors") and display the other by using an image in which textures are assigned ("expressed with textures"). In another example, as illustrated in the right section of FIG. 6, the display controlling function 155d may display a WSS image by using an image in which magnitudes and directions of the WSS are expressed with the quantity and directions of the arrows, respectively ("expressed with quantity and directions of arrows"). In this situation, for example, when the user is enabled to arbitrarily set a display mode for each of the pieces of information by using the user interface as mentioned above, the display controlling function 155d may be configured to display a warning when the user sets the display modes of the images to be the same as or similar to each other. In another example, to prevent the situation where one is mistaken for the other, the display controlling function 155d may exercise control so that the user is unable to select display modes that are the same as or similar to each other.

In yet another example, as illustrated in FIG. 7, the display controlling function 155d may display mutually-different text sets or marks within an FFR image and a WSS image. In this situation, for example, because the displayed text or marks may hinder the observation, the display controlling function 155d may hide the text or mark displayed within whichever image being observed, when the image starts being observed by the user (e.g., when the user has performed an operation to make the display window active, an operation to view (browse) the image, or an operation to direct a line of sight onto the image). In yet another example, when the images are displayed in conjunction with each other as described above, the display controlling function 155d may exercise control so that the text or mark displayed within one of the images being observed is hidden, whereas the text or mark displayed within the other image not being observed is not hidden.

A Fourth Modification Example of the First Embodiment

Further, for instance, in the first embodiment described above, the example was explained in which the FFR and the WSS are displayed by using the three-dimensional images (e.g., VR images or SR images) of the coronary arteries; however, possible embodiments are not limited to this example.

For instance, as a fourth modification example of the first embodiment, the medical image processing apparatus 150 may be configured to display the FFR and the WSS by using another image indicating the coronary arteries.

More specifically, the display controlling function 155d may be configured to display the image indicating the coronary arteries so as to display, within the image, the FFR and the WSS calculated by the calculating function 155b and arranged either on top of each other or side by side.

For example, the display controlling function 155d may display the WSS and/or the FFR corresponding to each of the various positions in the coronary artery CT image so as to be arranged on top of each other.

FIGS. 8 and 9 are drawings illustrating examples of the information display performed by the display controlling function 155d according to the fourth modification example of the first embodiment.

For example, as illustrated in the left section of FIG. 8, the display controlling function 155d may reconstruct a curved Multi Planar Reconstruction (MPR) image linearly expressing a coronary artery by implementing curved MPR so that in the display a corresponding WSS or FFR value is assigned to each of the positions in the curved MPR image.

In another example, as illustrated in the right section of FIG. 8, when displaying the curved MPR image, the display controlling function 155d may display the right half of the blood vessel by using a display mode corresponding to the FFR and display the left half by using a display mode corresponding to the WSS. This arrangement makes it possible to efficiently observe the positions in the blood vessel with the FFR and the WSS at the same time.

Possible examples of displaying the FFR and the WSS so as to be divided into the left and the right sections are not limited to the example using the curved MPR. For instance, the display controlling function 155d may use a VR image or an SR image. In that situation, for example, the display controlling function 155d may divide the VR image or the SR image into left and right sections while using the display direction of a display screen (e.g., the direction from the front to the back of the screen) as an axis, to exercise control so that, even when the VR image or the SR image is rotated, the FFR and the WSS are displayed on the left side and the right side of each blood vessel branch at all times. This example is effective when using a calculation method by which blood vessel cross-sections in mutually the same position have mutually the same value, like the 1D-FFR or the 1D-WSS.

In another example, the display controlling function 155d may display the FFR and/or the WSS by using polar coordinate display (which may be referred to as a "polar map") of segments of the myocardia. In this situation, the polar coordinate display of the myocardia segments is presented as an image in which the myocardia are developed and schematically expressed. In the image, as illustrated in the top section of FIG. 9, for example, a basal part ("Basal"), a middle part ("Mid"), and an apical part ("Apical") of the myocardia are each expressed with an annular region centered on a short axis, so that each of the regions corresponding to the different parts is divided into a plurality of segments along the circumferential direction. Further, in the polar coordinate display of the myocardia segments, each of the segments is categorized as one of the following: a Left Anterior Descending artery (LAD) dominant region; a Left Circumflex artery (LCX) dominant region; and a Right Coronary Artery (RCA) dominant region. In this situation, as illustrated in the bottom section of FIG. 9, for example, the display controlling function 155d divides each of the regions corresponding to the segments in the polar coordinate display of the myocardia segments into a top half and a bottom half, so as to display the FFR in one of the two and to display the WSS in the other. In that situation, for example, with respect to each of the segments in the polar coordinate display of the myocardia segments, the display controlling function 155d identifies a blood vessel corresponding to the segment, further calculates a representative value such as an average value or a maximum value for the FFR and the WSS values in various positions in the identified blood vessel, so as to assign the calculated values to the segment.

A Fifth Modification Example of the First Embodiment

Further, in the first embodiment described above, the example was explained in which the type of information to be displayed on the display 154 is determined in accordance with the degree of the coronary artery disease; however, possible embodiments are not limited to this example.

For instance, as a fifth modification example of the first embodiment, the medical image processing apparatus 150 may be configured to determine the type of information to be displayed on the display 154 according to an instruction from the user.

More specifically, the display controlling function 155d may be configured to receive, from the user, an operation to select the type of information to be displayed on the display 154 and to cause the display 154 to display one or both of the FFR and the WSS calculated by the calculating function 155b in accordance with the received operation.

For example, the display controlling function 155d may present, to the user, the presence probability of myocardial ischemia in the coronary artery CT image, by using the user interface realized with the input interface 153 and the display 154. Further, by using the user interface, the display controlling function 155d receives, from the user, the operation to select the type of information to be displayed on the display 154 from between the FFR and the WSS. After that, the display controlling function 155d causes the display 154 to display the type of information selected by the user, in accordance with the received operation.

A Sixth Modification Example of the First Embodiment

In the first embodiment described above, only the FFR is displayed when the disease degree indicating the degree of the coronary artery disease is higher than the first threshold value, whereas only the WSS is displayed when the disease degree indicating the degree of the coronary artery disease is lower than the second threshold value; however, possible embodiments are not limited to this example.

For instance, as a sixth modification example of the first embodiment, the medical image processing apparatus 150 may be configured to switch the display from displaying only one of the FFR and the WSS, to displaying the other, according to an instruction from the user.

More specifically, the display controlling function 155d may receive, from the user, an operation to switch the display between the FFR and the WSS, so as to switch, according to the received operation, from the state in which one of the FFR and the WSS calculated by the calculating function 155b is displayed, to the state in which the other is displayed.

For example, while only one of the FFR and the WSS is displayed, the display controlling function 155d receives, from the user, an operation to switch the display to the other, via the input interface 153. Further, according to the received operation, the display controlling function 155d switches the display from the FFR to the WSS or from the WSS to the FFR.

Second Embodiment

In the first embodiment described above, the example was explained in which the FFR and/or the WSS are displayed in accordance with the degree of the coronary artery disease; however, possible embodiments are not limited to this example.

For instance, when the time at which the medical image was taken (hereinafter, "imaging time of the medical image") was before the subject was treated, predicted FFR and/or predicted WSS after the treatment may be displayed by applying virtual treatment to the blood vessels while using the medical image. In the following sections, this example will be explained as a second embodiment. The following will describe configurations of a medical image processing system and a medical image processing apparatus according to the second embodiment, while a focus is placed on differences from the first embodiment. Some of the constituent elements that are the same will be referred to by using the same reference characters, and detailed explanations thereof will be omitted.

Figure 10:
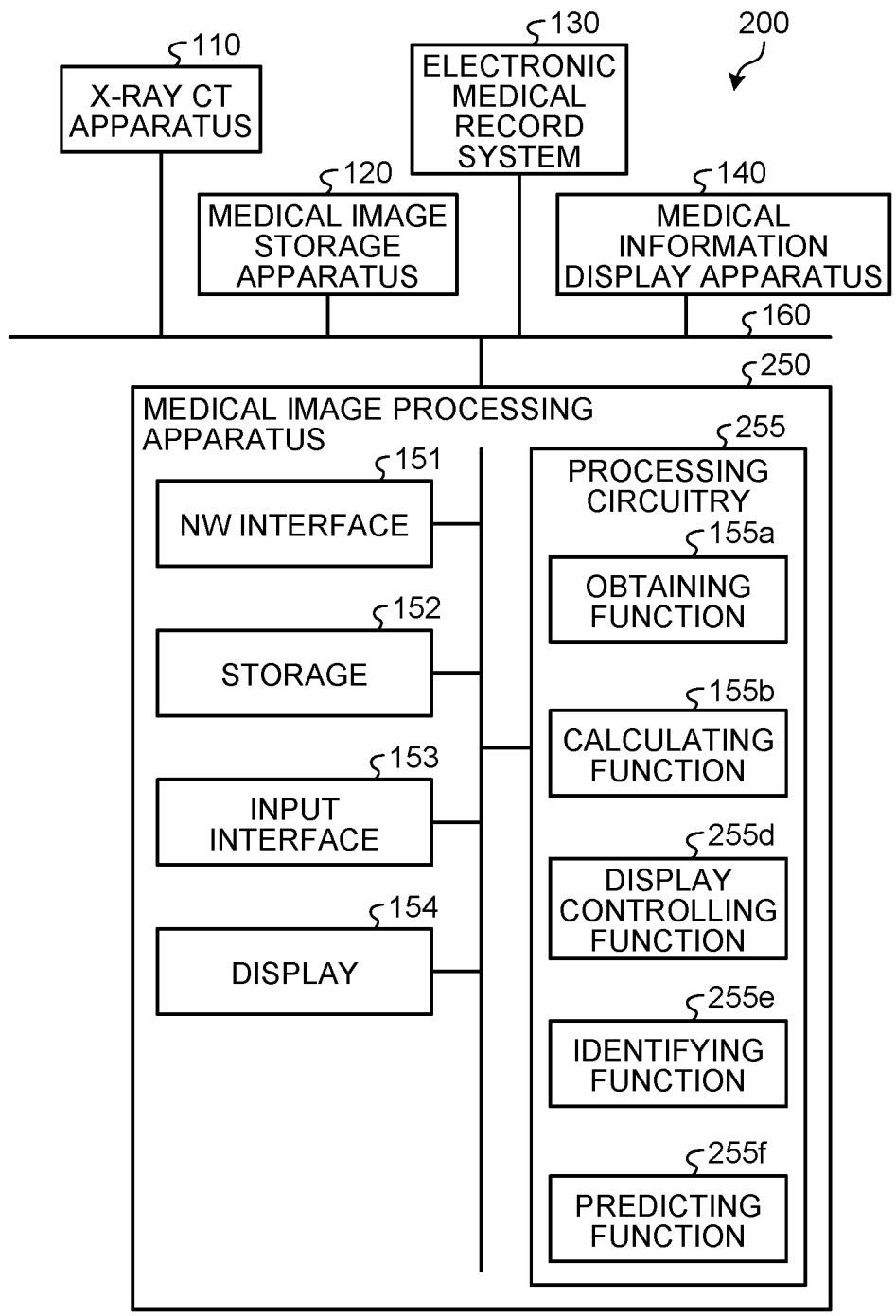
FIG. 10 is a diagram illustrating an exemplary configuration of a medical image processing system and a medical image processing apparatus according to a second embodiment.

FIG. 10 is a diagram illustrating an exemplary configuration of a medical image processing system and a medical image processing apparatus according to the second embodiment.

For example, as illustrated in FIG. 10, a medical image processing system 200 according to the present embodiment includes the X-ray CT apparatus 110, the medical image storage apparatus 120, the electronic medical record system 130, the medical information display apparatus 140, and a medical image processing apparatus 250. In the present example, the apparatuses and the system are communicably connected via the network 160.

The medical image processing apparatus 250 is configured to perform various types of image processing processes related to the subject. More specifically, the medical image processing apparatus 250 is configured to obtain the CT image from either the X-ray CT apparatus 110 or the medical image storage apparatus 120 via the network 160, to obtain the diagnosis/treatment data from the electronic medical record system 130, and to perform the various types of image processing processes by using the CT image and the diagnosis/treatment data. For example, the medical image processing apparatus 250 is realized by using a computer device such as a server or a workstation.

For example, the medical image processing apparatus 250 includes the NW interface 151, the storage 152, the input interface 153, the display 154, and processing circuitry 255.

Further, in the present embodiment, the processing circuitry 255 of the medical image processing apparatus 250 includes the obtaining function 155a, an identifying function 255e, the calculating function 155b, a predicting function 255f, and a display controlling function 255d. In this situation, the identifying function 255e is an example of the identifying unit. The predicting function 255f is an example of the predicting unit. Further, the display controlling function 255d is an example of the display controlling unit.

The identifying function 255e is configured to identify whether the imaging time of the coronary artery CT image of the subject obtained by the obtaining function 155a was before the subject was treated or after the subject was treated.

For example, on the basis of the imaging time of the coronary artery CT image, the identifying function 255e judges whether or not it is possible to perform the process at the next step. In this situation, for example, the identifying function 255e obtains the patient information of the subject from the electronic medical record system 130 via the NW interface 151 and identifies the imaging time of the coronary artery CT image on the basis of the obtained information. In this situation, the identifying function 255e may obtain the patient information from the HIS, the RIS, or the like. When the imaging time is identified as before the subject had surgery, the identifying function 255e determines that it is possible to perform the process at the next step. On the contrary, when the imaging time is identified as after the subject had surgery, the identifying function 255e determines that it is not possible to perform the process at the next step. In another example, when the imaging time is identified as before a medication was administered for the subject, the identifying function 255e determines that it is possible to perform the process at the next step. On the contrary, when the imaging time is identified as after a medication was administered for the subject, the identifying function 255e determines that it is not possible to perform the process at the next step. In these situations, the surgery and having the medication administered are examples of treatment.

Possible methods for identifying the imaging time are not limited to the example described above, and it is possible to use any of various types of methods. For example, the identifying function 255e may detect a treatment device from the coronary artery CT image by using a known method, so as to identify whether the imaging time was before treatment or after treatment, depending on the presence/absence of the treatment device.

When the identifying function 255e identifies that the imaging time of the coronary artery CT image of the subject was before the subject was treated, the predicting function 255f is configured to calculate one or both of predicted FFR being post-treatment FFR and predicted WSS being post-treatment WSS, by applying virtual treatment to the coronary arteries while using the coronary artery CT image. In this situation, the predicted FFR is an example of the first predicted index value, whereas the predicted WSS is an example of the second predicted index value.

For example, when the identifying function 255e determines that it is possible to perform the process at the next step, the predicting function 255f predicts and calculates FFR and WSS in each of various positions in the blood vessels after the treatment, by applying virtual treatment to the coronary arteries on a computer, while using the coronary artery CT image of the subject. For example, the predicting function 255f applies the virtual treatment by using a method such as that described in Gijsen, Frank J. H. et al., "Simulation of stent deployment in a realistic human coronary artery", Biomedical Engineering Online 7.1 (2008): 23. In this situation, generally speaking, because the virtual treatment process requires a high processing cost and long processing time on a computer, it is also acceptable to use a dedicated computation processing device. On the contrary, when the identifying function 255e determines that it is not possible to perform the process at the next step, the predicting function 255f does not apply the virtual treatment.

When the identifying function 255e identifies that the imaging time of the coronary artery CT image of the subject was before the subject was treated, the display controlling function 255d causes the display 154 to display one or both of the predicted FFR and the predicted WSS calculated by the predicting function 255f.

More specifically, when the imaging time is identified as before the subject was treated, the display controlling function 255d displays one or both of the FFR and the WSS calculated by the calculating function 155b on the basis of the coronary artery CT image of the subject and one or both of the predicted FFR and the predicted WSS calculated by the predicting function 255f. In contrast, when the imaging time is identified as after the subject was treated, the display controlling function 255d displays one or both of the FFR and the WSS calculated by the calculating function 155b on the basis of the coronary artery CT image of the subject.

Figure 11:
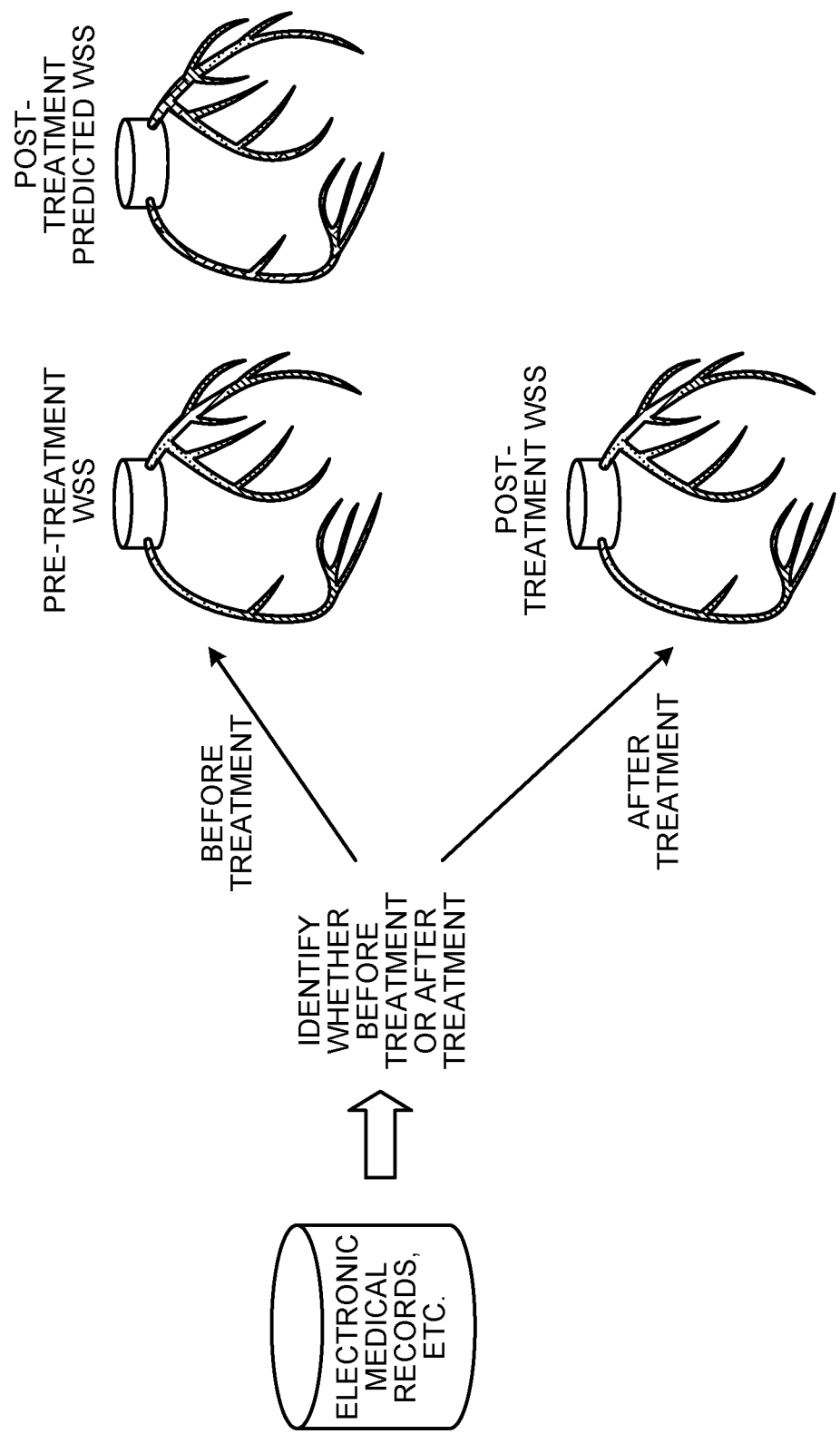
FIG. 11 is a drawing illustrating an example of information display performed by a display controlling function according to the second embodiment.
Figure 12:
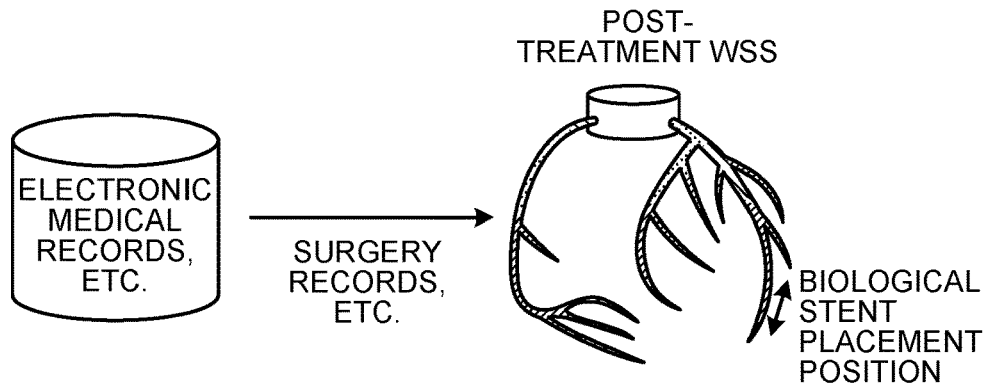
FIG. 12 is a drawing illustrating another example of the information display performed by the display controlling function according to the second embodiment.

FIGS. 11 and 12 are drawings illustrating examples of the information display performed by the display controlling function 255d according to the second embodiment.

For example, as illustrated in FIG. 11, the display controlling function 255d determines the type of information to be displayed on the display 154, on the basis of the imaging time of the coronary artery CT image identified by the identifying function 255e. In this situation, for example, when the identifying function 255e identifies that the imaging time was before the subject was treated, the display controlling function 255d determines the type of information to be displayed as the WSS (pre-treatment WSS) calculated by the calculating function 155b and the predicted WSS (post-treatment predicted WSS) calculated by the predicting function 255f. On the contrary, when the identifying function 255e identifies that the imaging time was after the subject was treated, the display controlling function 255d determines the type of information to be displayed as the WSS (post-treatment WSS) calculated by the calculating function 155b.

In this situation, for example, when displaying the WSS calculated by the calculating function 155b, the display controlling function 255d may further determine to also display the FFR calculated by the calculating function 155b.

In another example, when displaying the predicted WSS calculated by the predicting function 255f, the display controlling function 255d may further determine to also display the predicted FFR calculated by the predicting function 255f.

After that, the display controlling function 255d causes the display 154 to display the determined type of information. For example, similarly to the first embodiment and the modification examples thereof, the display controlling function 255d displays the determined type of information. In this situation, for example, on the basis of the patient information of the subject obtained by the identifying function 255e, the display controlling function 255d may display, at the same time, information such as a treatment history, a medication history, or a blood test value (e.g., a hematocrit value) of the subject. For example, as illustrated in FIG. 12, when the imaging time was after treatment, the display controlling function 255d may display, at the same time, information such as the type of a treatment device (e.g., a biological stent) and a placement position, on the basis of a surgery record or the like included in the patient information of the subject.

Further, for example, by performing a known image processing process on the coronary artery CT image, the display controlling function 255d may calculate an image feature value (e.g., a calcium score or information related to the blood vessel diameter) related to a coronary artery disease and further display the image feature value at the same time. In another example, the display controlling function 255d may display, at the same time, additional information (e.g., the imaging period or a cardiac phase) of the image obtained from information in a DICOM header or the like associated with the coronary artery CT image. In yet another example, the display controlling function 255d may display, at the same time, a reliability of the computation at the time of calculating the WSS and/or the FFR or a reliability of the computation for the calculation during the treatment simulation. In this situation, for example, when machine learning is used, it is possible to calculate the reliability on the basis of how much the data in question deviates from a learning model, or the like.

Further, for example, similarly to the fourth modification example of the first embodiment, by using the curved MPR, the display controlling function 255d may display the FFR and the WSS calculated by the calculating function 155b so as to be divided into left and right sections or may display the predicted FFR and the predicted WSS calculated by the predicting function 255f so as to be divided into left and right sections. Further, for example, by using the polar coordinate display of the myocardia segments, the display controlling function 255d may display the FFR and the WSS calculated by the calculating function 155b so as to be divided into top and bottom sections or may display the predicted FFR and the predicted WSS calculated by the predicting function 255f so as to be divided into top and bottom sections.

Figure 13:
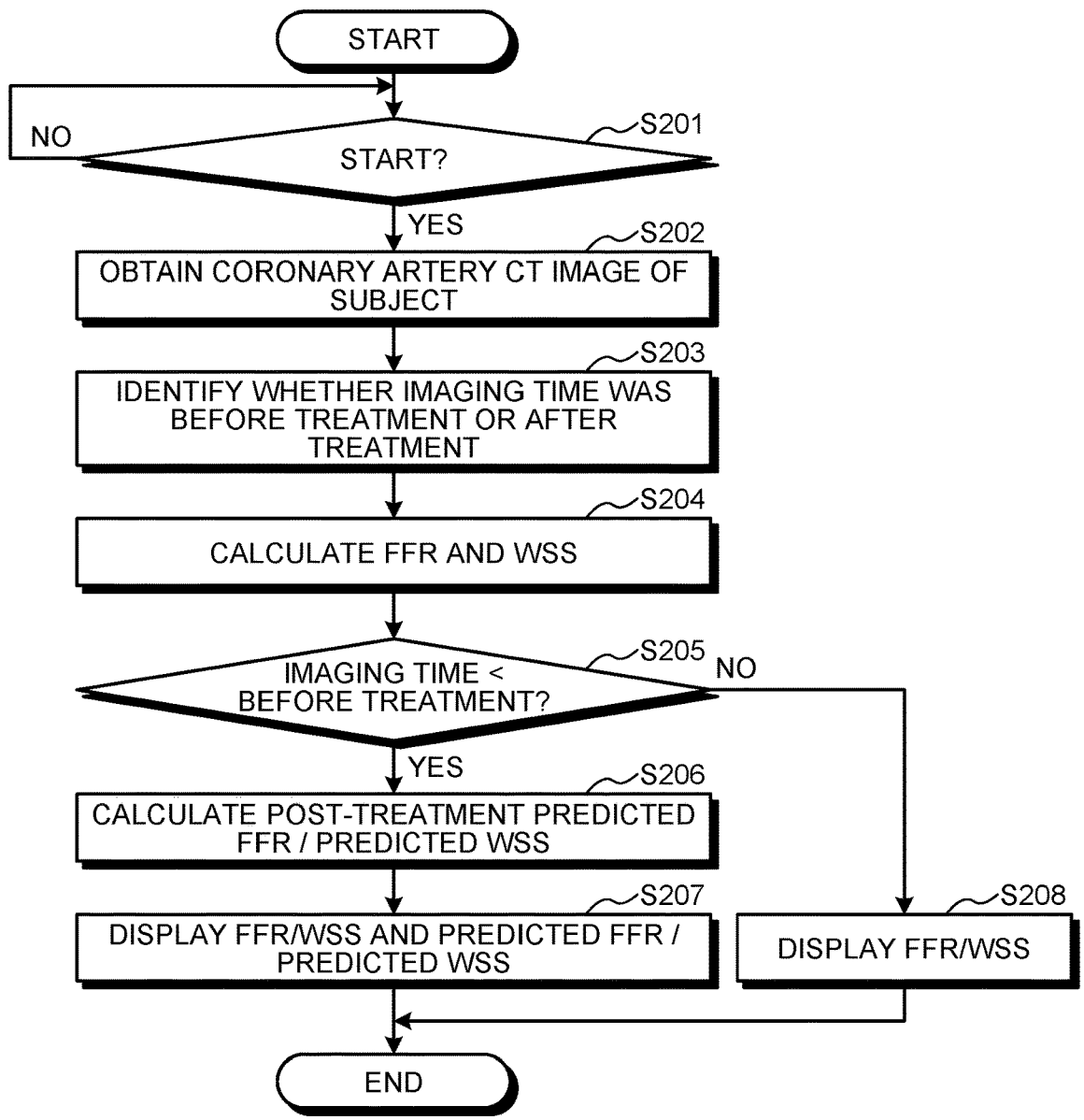
FIG. 13 is a flowchart illustrating a processing procedure of a process performed by processing functions included in processing circuitry of the medical image processing apparatus according to the second embodiment.

FIG. 13 is a flowchart illustrating a processing procedure of a process performed by the processing functions included in the processing circuitry 255 of the medical image processing apparatus 250 according to the second embodiment.

For example, as illustrated in FIG. 13, in the present embodiment, upon receipt of an instruction to start the process from the user via the input interface 153 (step S201: Yes), the obtaining function 155a obtains a coronary artery CT image of the subject from either the X-ray CT apparatus 110 or the medical image storage apparatus 120 (step S202). For example, this process is realized as a result of the processing circuitry 255 invoking and executing the program corresponding to the obtaining function 155a from the storage 152.

Subsequently, the identifying function 255e identifies whether the imaging time of the coronary artery CT image of the subject obtained by the obtaining function 155a was before the subject was treated or after the subject was treated (step S203). For example, this process is realized as a result of the processing circuitry 255 invoking and executing a program corresponding to the identifying function 255e from the storage 152.

After that, on the basis of the coronary artery CT image of the subject obtained by the obtaining function 155a, the calculating function 155b calculates FFR and WSS as the information related to the blood flows of the coronary arteries (step S204). For example, this process is realized as a result of the processing circuitry 255 invoking and executing the program corresponding to the calculating function 155b from the storage 152.

Subsequently, when the identifying function 255e identifies that the imaging time of the coronary artery CT image of the subject was before the subject was treated (step S205: Yes), the predicting function 255f calculates one or both of the predicted FFR and the predicted WSS after the treatment, by applying the virtual treatment to the coronary arteries while using the coronary artery CT image (step S206). For example, this process is realized as a result of the processing circuitry 255 invoking and executing a program corresponding to the predicting function 255f from the storage 152.

Subsequently, when the identifying function 255e identifies that the imaging time was before the subject was treated (step S205: Yes), the display controlling function 255d displays one or both of the FFR and the WSS calculated by the calculating function 155b on the basis of the coronary artery CT image of the subject and one or both of the predicted FFR and the predicted WSS calculated by the predicting function 255f (step S207). On the contrary, when the identifying function 255e identifies that the imaging time was after the subject was treated (step S205: No), the display controlling function 255d displays one or both of the FFR and the WSS calculated by the calculating function 155b on the basis of the coronary artery CT image of the subject (step S208). For example, this process is realized as a result of the processing circuitry 255 invoking and executing a program corresponding to the display controlling function 255d from the storage 152.

As explained above, in the second embodiment, when the imaging time of the medical image was before the subject was treated, the medical image processing apparatus 250 is configured to calculate and display the predicted FFR and/or the predicted WSS after the treatment, by applying the virtual treatment to the blood vessels while using the medical image. With this arrangement, it is possible to automatically display the information indicating the advantageous effects of the treatment at the time of performing a diagnosing process or making a treatment plan in relation to cardiac diseases. Consequently, according to the second embodiment, it is possible to reduce the trouble of the user at the time of performing the diagnosing process, making the treatment plan, or the like in relation to cardiac diseases.

A First Modification Example of the Second Embodiment

In the second embodiment described above, the example was explained in which, when the imaging time of the coronary artery CT image of the subject was before the subject was treated, the predicted FFR and/or the predicted WSS after the treatment are displayed; however, possible embodiments are not limited to this example.

For instance, as a first modification example of the second embodiment, the medical image processing apparatus 250 may be configured to switch the display between one or both of the 1D-FFR and the 1D-WSS and one or both of the 3D-FFR and the 3D-WSS, in accordance with the imaging time of the coronary artery CT image.

More specifically, when the identifying function 255e identifies that the imaging time was before the subject was treated, the display controlling function 255d displays one or both of the 3D-FFR and the 3D-WSS calculated by the calculating function 155b. On the contrary, when the identifying function 255e identifies that the imaging time was after the subject was treated, the display controlling function 255d displays one or both of the 1D-FFR and the 1D-WSS calculated by the calculating function 155b.

Figure 14:
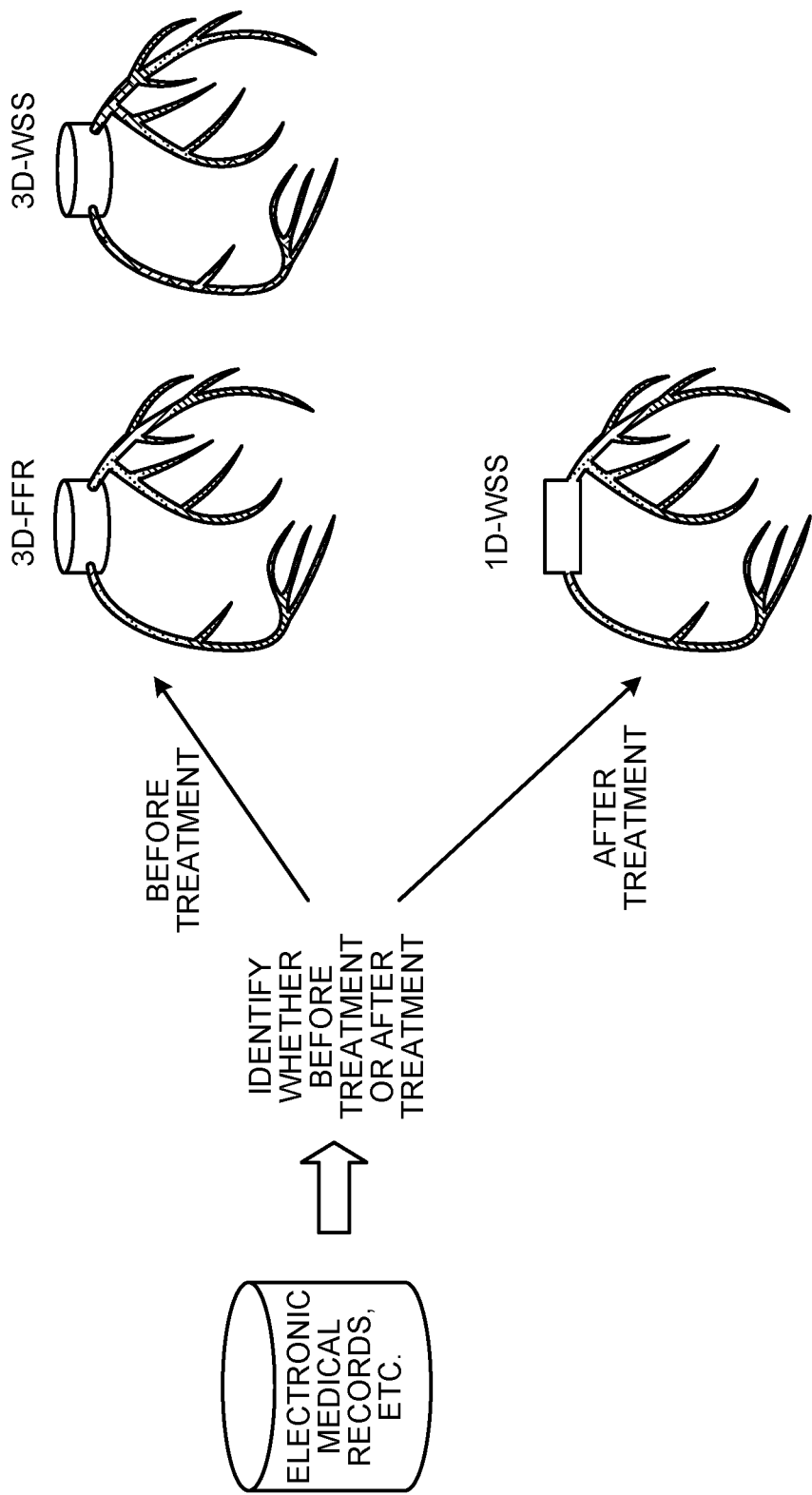
FIG. 14 is a drawing illustrating an example of information display performed by a display controlling function according to a first modification example of the second embodiment.

FIG. 14 is a drawing illustrating an example of the information display performed by the display controlling function 255d according to the first modification example of the second embodiment.

For example, as illustrated in FIG. 14, when the identifying function 255e identifies that the imaging time was before the subject was treated, the display controlling function 255d determines the type of information to be displayed as the 3D-FFR and the 3D-WSS calculated by the calculating function 155b. On the contrary, when the identifying function 255e identifies that the imaging time was after the subject was treated, the display controlling function 255d determines the type of information to be displayed as the 1D-WSS calculated by the calculating function 155b.

Possible examples of displaying the FFR and the WSS in the present modification example are not limited to the configuration described above. For instance, when the imaging time is identified as before the subject was treated, the display controlling function 255d may determine the type of information to be displayed as one of the 3D-FFR and the 3D-WSS. Alternatively, when the imaging time is identified as before the subject was treated, the display controlling function 255d may determine the type of information to be displayed either as the 1D-FFR or as both the 1D-FFR and the 3D-WSS. In each of these situations, for example, the display controlling function 255d may determine to display information designated by the user from between the FFR and the WSS.

A Second Modification Example of the Second Embodiment

Further, in the second embodiment described above, the example was explained in which the predicted FFR and/or the predicted WSS are calculated before the type of information to be displayed is determined; however, possible embodiments are not limited to this example.

For instance, as a second modification example of the second embodiment, the medical image processing apparatus 250 may be configured to calculate the predicted FFR and/or the predicted WSS after determining the type of information to be displayed.

More specifically, the predicting function 255f may calculate one or both of the predicted FFR and the predicted WSS, after the display controlling function 255d determines to display the one or both of the predicted FFR and the predicted WSS.

A Third Modification Example of the Second Embodiment

Further, in the second embodiment described above, the example was explained in which the predicted FFR and/or the predicted WSS after the treatment are calculated without any input from the user, by applying the virtual treatment to the coronary arteries while using the coronary artery CT image; however, possible embodiments are not limited to this example.

Generally speaking, to apply virtual treatment, it is necessary to postulate and set various parameters. For example, any of the following may be postulated and set: the firmness of the blood vessels, a physical property value of the blood (e.g., a hematocrit value), the shape of the blood vessels after the treatment (e.g., the curvatures of the blood vessel branches), an anatomical characteristic such as of the property of plaque, the type of a treatment device, and treatment methods such as the type and the quantity of a medication.

Accordingly, for example, as a third modification example of the second embodiment, the medical image processing apparatus 250 may be configured to receive, from the user, parameters to be used at the time of applying the virtual treatment.

More specifically, the predicting function 255f may receive, from the user, an operation to input the parameters to be used at the time of applying the virtual treatment, so as to calculate one or both of the predicted FFR and the predicted WSS by using the received parameters.

For example, the predicting function 255f may receive the input of the parameters to be used at the time of applying the virtual treatment, by using the user interface realized with the input interface 153 and the display 154. In this situation, for example, the predicting function 255f may allow numerical values of the parameters to be directly designated or may allow the user to arbitrarily select from among a plurality of parameter set candidates determined in advance. Further, the predicting function 255f calculates the predicted FFR and the predicted WSS by applying the virtual treatment while using the input parameters and further presents, to the user, the calculated predicted FFR and WSS, by using the user interface.

Figure 15:
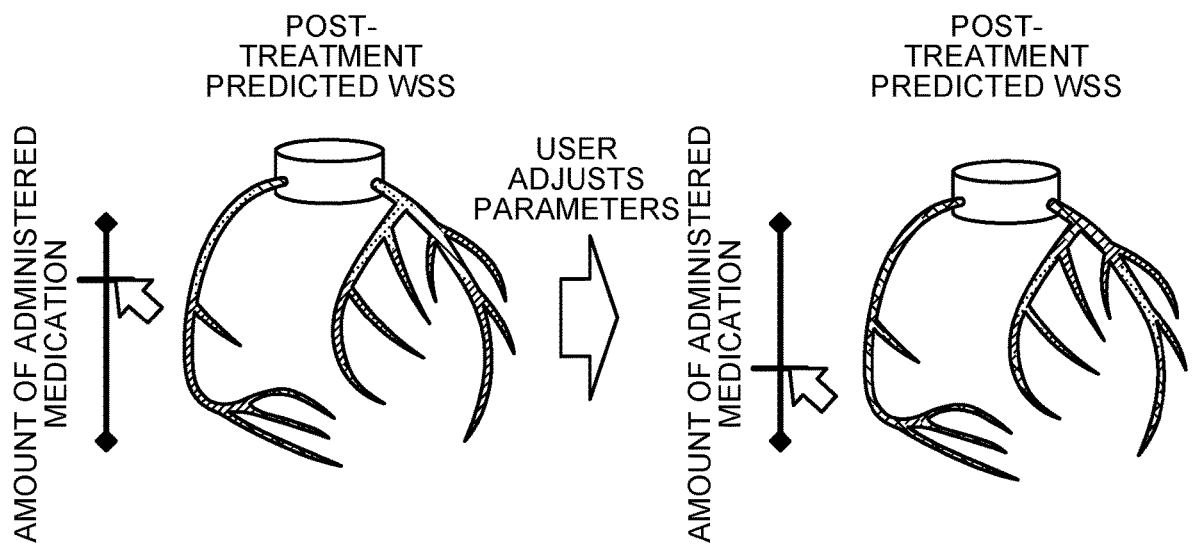
FIG. 15 is a drawing illustrating an example of a user interface used by a predicting function according to a third modification example of the second embodiment.
Figure 16:
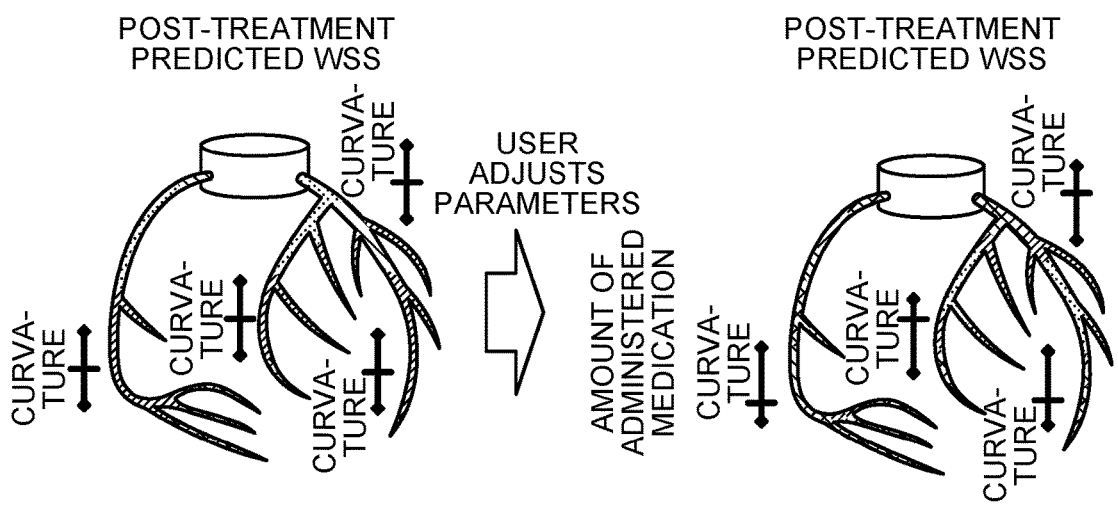
FIG. 16 is a drawing illustrating another example of the user interface used by the predicting function according to the third modification example of the second embodiment.
Figure 17:
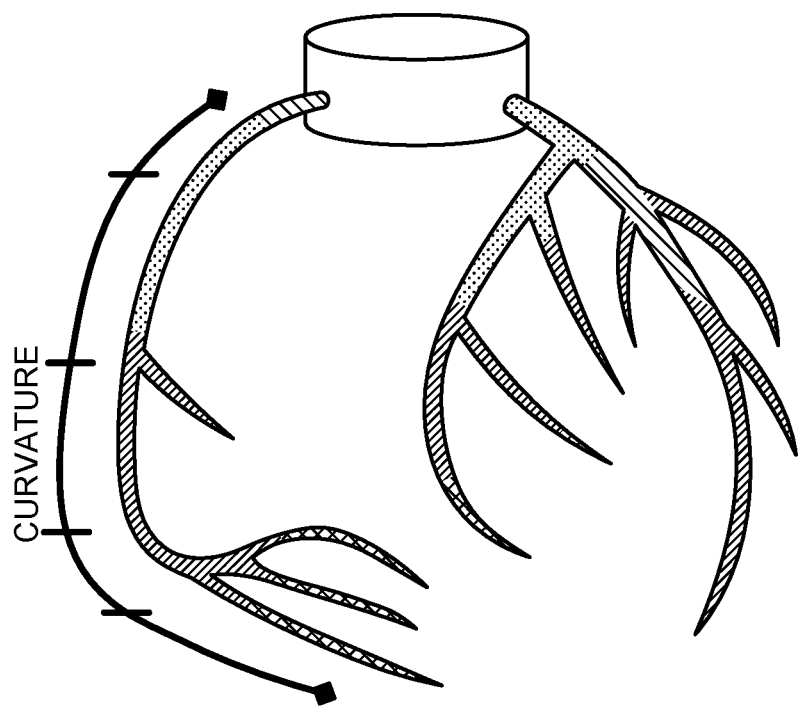
FIG. 17 is a drawing illustrating yet another example of the user interface used by the predicting function according to the third modification example of the second embodiment.

FIGS. 15 to 17 are drawings illustrating examples of the user interface used by the predicting function 255f according to the third modification example of the second embodiment.

For example, as illustrated in FIGS. 15 to 17, the predicting function 255f causes the display 154 to display an image in which predicted WSS (post-treatment predicted WSS) calculated by using input parameters is assigned, as well as slider bars corresponding to values of the parameters. In this situation, the predicting function 255f allows the user to set arbitrary parameters, by receiving, from the user, an operation to adjust the slider bars via the input interface 153. Further, when the parameters have been adjusted by the user, the predicting function 255f calculates predicted WSS by using the adjusted parameters and further updates the image displayed on the display 154 on the basis of the calculate predicted WSS.

In this situation, for example, the predicting function 255f may be configured to change items of parameters that can be set with the slider bars, depending on the magnification ratio of the image. For example, while the user is observing the entirety of the coronary arteries by using a low magnification ratio, because one or more parameters having an impact on the entirety are expected to be changed, the predicting function 255f sets one or more parameter items (e.g., "amount of administered medication") having an impact on the entirety of the coronary arteries, as illustrated in FIG. 15. On the contrary, for example, while the user is observing various positions in the blood vessels by using a high magnification ratio, because one or more parameters having an impact on the various positions are expected to be changed, the predicting function 255f sets one or more parameter items (e.g., "curvature") having an impact on the various positions in the blood vessels, as illustrated in FIG. 16.

Further, for example, as illustrated in FIG. 17, the predicting function 255f may display a slider bar in a curved shape that is bent to fit the shape of a blood vessel. In this situation, for example, the predicting function 255f may make it possible to set various curvatures with the single slide bar, by setting a point of variation for each of sections having a specific curvature. For example, the predicting function 255f may set the point of variation with respect to each of the segments of the coronary arteries classified by an academic institution or the like. In another example, the predicting function 255f may restrict moving of the point of variation on the slider bar (e.g., the width or the speed with which the point of variation can be moved) in accordance with a condition related to the structures of the blood vessels or a condition related to a treatment device. In yet another example, the predicting function 255f may display text, a mark, graduation, or the like on the slider bar in the position of a predicted WSS value corresponding to a threshold value used for determining whether or not treatment is required.

Further, in yet another example, the predicting function 255f may receive an input of one or more parameters other than the parameters used at the time of applying the virtual treatment. In that situation, for example, the predicting function 255f receives an input of a heart rate, estimates a change in the blood pressure on the basis of the input heart rate, and calculates predicted WSS on the basis of the estimated blood pressure.

Although FIGS. 15 to 17 illustrate the examples of the user interface at the time of calculating and displaying the predicted WSS, the predicting function 255f may, for example, calculate and display predicted FFR by receiving an input of one or more parameters using the same or a similar user interface.

A Fourth Modification Example of the Second Embodiment

In the second embodiment described above, the example was explained in which the information corresponding to a single point in time obtained from the coronary artery CT image subject to the analysis is displayed; however, possible embodiments are not limited to this example.

For instance, as a fourth modification example of the second embodiment, the medical image processing apparatus 250 may be configured to display information corresponding to plurality of points in time.

More specifically, when the identifying function 255e identifies that the imaging time was after the subject was treated, the display controlling function 255d may display one or both of FFR and WSS calculated by the calculating function 155b on the basis of a coronary artery CT image of the subject before the treatment and one or both of FFR and WSS calculated by the calculating function 155b on the basis of a coronary artery CT image of the subject after the treatment.

Figure 18:
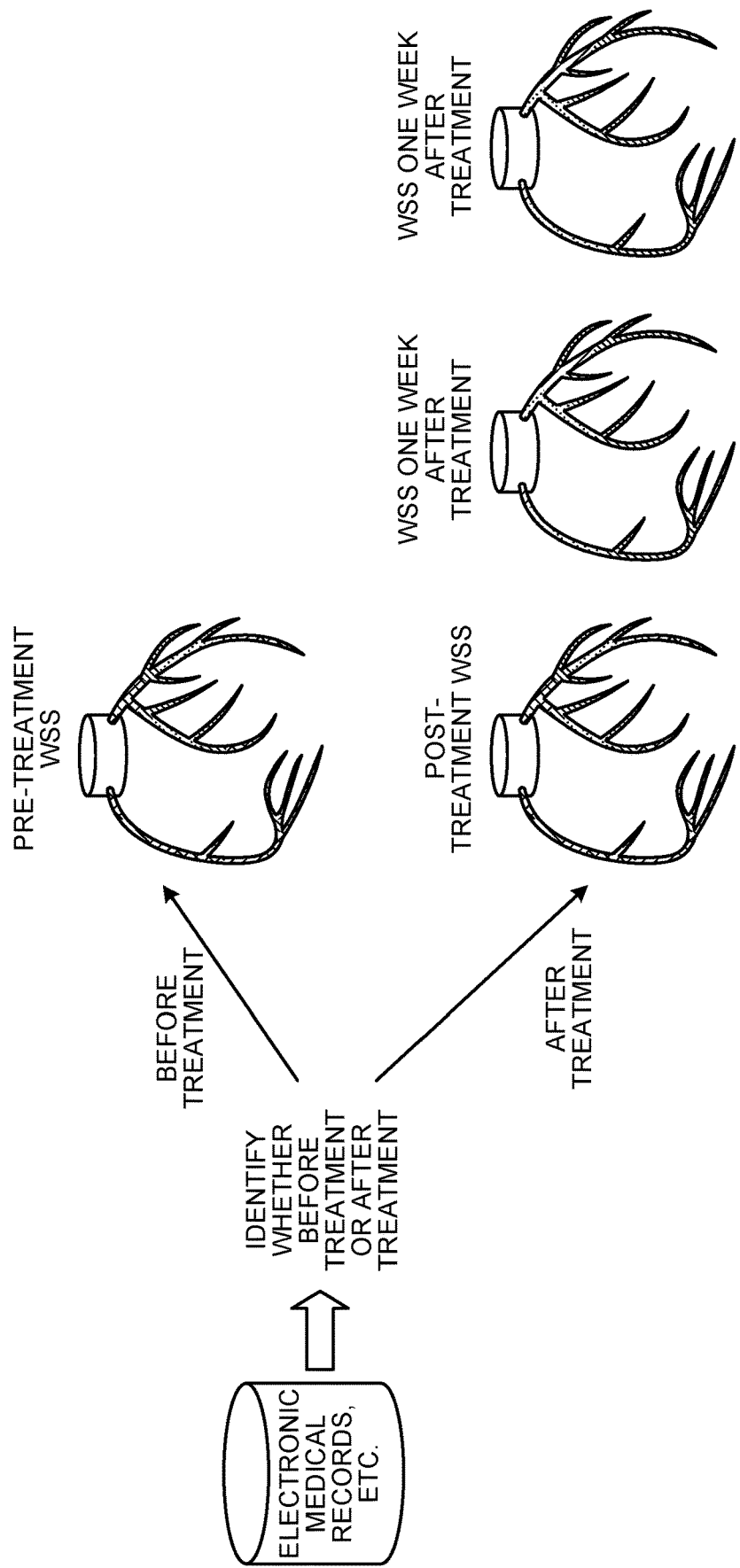
FIG. 18 is a drawing illustrating an example of information display performed by a display controlling function according to a fourth modification example of the second embodiment.

FIG. 18 is a drawing illustrating an example of the information display performed by the display controlling function 255d according to the fourth modification example of the second embodiment.

For example, as illustrated in FIG. 18, when the identifying function 255e identifies that the imaging time was after the subject was treated, the display controlling function 255d determines the type of information to be displayed as the WSS (pre-treatment WSS) calculated by the calculating function 155b on the basis of the pre-treatment coronary artery CT image and the WSS calculated on the basis of the post-treatment coronary artery CT image. In this situation, for example, the display controlling function 255d may determine the WSS based on the post-treatment coronary artery CT image to be WSS values at a plurality of points in time after the treatment. For example, the display controlling function 255d determines the type of information to be displayed as a WSS value calculated on the basis of a coronary artery CT image taken one week after the treatment and a WSS value calculated on the basis of a coronary artery CT image taken one month after the treatment.

In another example, when the imaging time is identified as after stress is imposed on the subject, the display controlling function 255d may determine the type of information to be displayed to be a WSS value calculated on the basis of a coronary artery CT image taken before the stress and a WSS value calculated on the basis of a coronary artery CT image taken after the stress.

In yet another example, as for after the treatment, the display controlling function 255d may display WSS values regularly calculated after the treatment so as to be chronologically arranged, for the purpose of assessing advantageous effects of the treatment or may calculate the difference in WSS values between before the treatment and after the treatment so as to display an image in which the calculated difference is assigned.

Further, although FIG. 18 illustrates the example of displaying the WSS values, the display controlling function 255d may display, for example, FFR values at a plurality of points in time or both FFR and WSS values at a plurality of points in time, by using the same or a similar method.

Third Embodiment

In the first embodiment described above, the example was explained in which the FFR and/or the WSS are displayed in accordance with the degree of the coronary artery disease; however possible embodiments are not limited to this example.

For instance, it is acceptable to calculate, with respect to each of the blood vessel branches of the coronary arteries, the position and a rupture probability of plaque occurring at the blood vessel branch, so as to display FFR and/or WSS in accordance with the rupture probability. In the following sections, this example will be explained as a third embodiment. The following will describe configurations of a medical image processing system and a medical image processing apparatus according to the third embodiment, while a focus is placed on differences from the first embodiment. Some of the constituent elements that are the same will be referred to by using the same reference characters, and detailed explanations thereof will be omitted.

Figure 19:
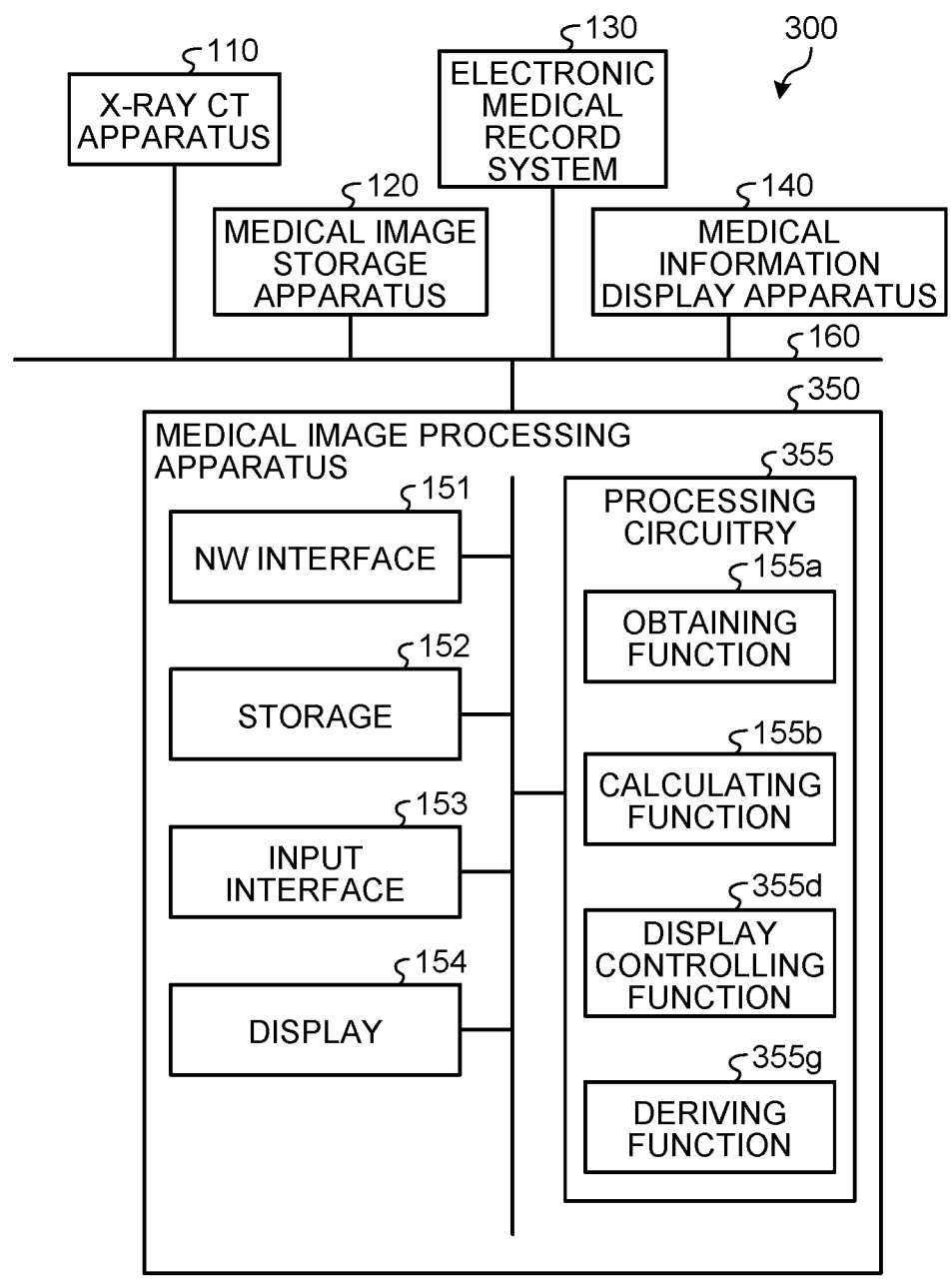
FIG. 19 is a diagram illustrating an exemplary configuration of a medical image processing system and a medical image processing apparatus according to a third embodiment.

FIG. 19 is a diagram illustrating an exemplary configuration of a medical image processing system and a medical image processing apparatus according to the third embodiment.

For example, as illustrated in FIG. 19, a medical image processing system 300 according to the present embodiment includes the X-ray CT apparatus 110, the medical image storage apparatus 120, the electronic medical record system 130, the medical information display apparatus 140, and a medical image processing apparatus 350. In the present example, the apparatuses and the system are communicably connected via the network 160.

The medical image processing apparatus 350 is configured to perform various types of image processing processes related to the subject. More specifically, the medical image processing apparatus 350 is configured to obtain the CT image from either the X-ray CT apparatus 110 or the medical image storage apparatus 120 via the network 160, to obtain the diagnosis/treatment data from the electronic medical record system 130, and to perform the various types of image processing processes by using the CT image and the diagnosis/treatment data. For example, the medical image processing apparatus 350 is realized by using a computer device such as a server or a workstation.

For example, the medical image processing apparatus 350 includes the NW interface 151, the storage 152, the input interface 153, the display 154, and processing circuitry 355.

Further, in the present embodiment, the processing circuitry 355 of the medical image processing apparatus 350 includes the obtaining function 155a, the calculating function 155b, a deriving function 355g, and a display controlling function 355d. In this situation, the deriving function 355g is an example of the deriving unit. The display controlling function 355d is an example of the display controlling unit.

On the basis of the coronary artery CT image of the subject obtained by the obtaining function 155a, the deriving function 355g is configured to derive, with respect to each of the blood vessel branches of the coronary arteries, the position and a rupture probability of plaque occurring at the blood vessel branch.

For example, by analyzing the coronary artery CT image of the subject, the deriving function 355g derives, with respect to each of the blood vessel branches of the coronary arteries, the position and the rupture probability of the plaque. In an example, the deriving function 355g may derive the position and the rupture probability of the plaque from information about the blood vessel diameters of the coronary arteries. In another example, the deriving function 355g may derive the position and the rupture probability of the plaque by performing a threshold value process using the coronary artery CT image. In yet another example, the deriving function 355g may derive the position and the rupture probability of the plaque by using a discriminator that has learned, in advance, characteristics of a distribution of pixel values in plaque through the machine learning technology.

With respect to each of the blood vessel branches of the coronary arteries, the display controlling function 355d causes the display 154 to display one of the FFR and the WSS calculated by the calculating function 155b, in accordance with the position and the rupture probability of the plaque derived by the deriving function 355g.

More specifically, the display controlling function 355d displays the FFR with respect to any of the blood vessel branches having plaque of which the rupture probability derived by the deriving function 355g is high. In contrast, the display controlling function 355d displays WSS with respect to any of the blood vessel branches having no plaque or having plaque of which the rupture probability is low.

Figure 20:
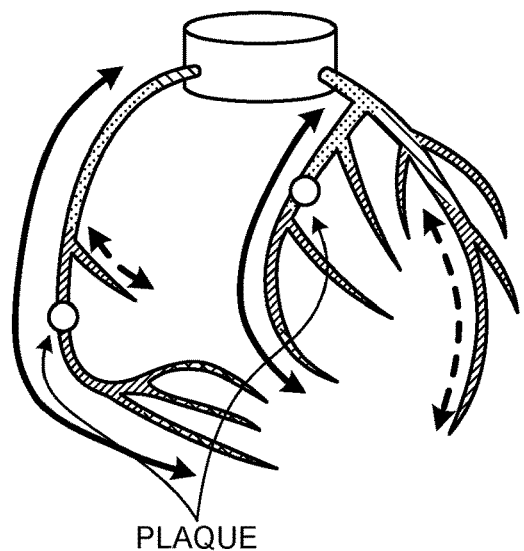
FIG. 20 is a drawing illustrating an example of information display performed by a display controlling function according to the third embodiment.

FIG. 20 is a drawing illustrating an example of the information display performed by the display controlling function 355d according to the third embodiment.

For example, as illustrated in FIG. 20, on the basis of the position and the rupture probability of the plaque derived by the deriving function 355g, the display controlling function 355d determines the type of information to be displayed on the display 154 in correspondence with each of the blood vessel branches. For example, with respect to any of the blood vessel branches (the spans indicated with the solid arrows in FIG. 20) having plaque of which the rupture probability is high, the display controlling function 355d determines the type of information to be displayed as the FFR. In contrast, with respect to any of the blood vessel branches (the span indicated with the broken-line arrow in FIG. 20) having no plaque or having plaque of which the rupture probability is low, the display controlling function 355d determines the type of information to be displayed as the WSS.

After that, the display controlling function 355d causes the display 154 to display the determined types of information. For example, similarly to the first embodiment and the modification examples thereof, the display controlling function 355d displays the determined types of information. It should be noted, however, in the present embodiment, that the display controlling function 355d displays an image in which both the FFR and WSS values are present. In this situation, for example, the display controlling function 355d may display the FFR and the WSS by using mutually-different display modes, similarly to the third modification example of the first embodiment.

In another example, the display controlling function 355d may simultaneously display the positions and the rupture probabilities of the plaque derived by the deriving function 355g. In yet another example, the display controlling function 355d may calculate a dominant region of each of the coronary arteries by using a known method so as to simultaneously display the calculated dominant regions of the coronary arteries. When the dominant regions of the coronary arteries are simultaneously displayed in this manner, it is possible to identify dominant regions that can be restored by treatment. It is therefore possible to more accurately identify the plaque that requires treatment. In yet another example, the display controlling function 355d may identify a region having inflammation, on the basis of a distribution of pixel values in the myocardial region in the surroundings of the coronal arteries, so as to simultaneously display the region having the inflammation. In this situation, for example, when the position of the inflammation is recognizable in another medical image such as a myocardial SPECT image, the display controlling function 355d may identify the region having the inflammation, by obtaining the other medical image and performing a position aligning process between the other medical image and the coronary artery CT image.

Figure 21:
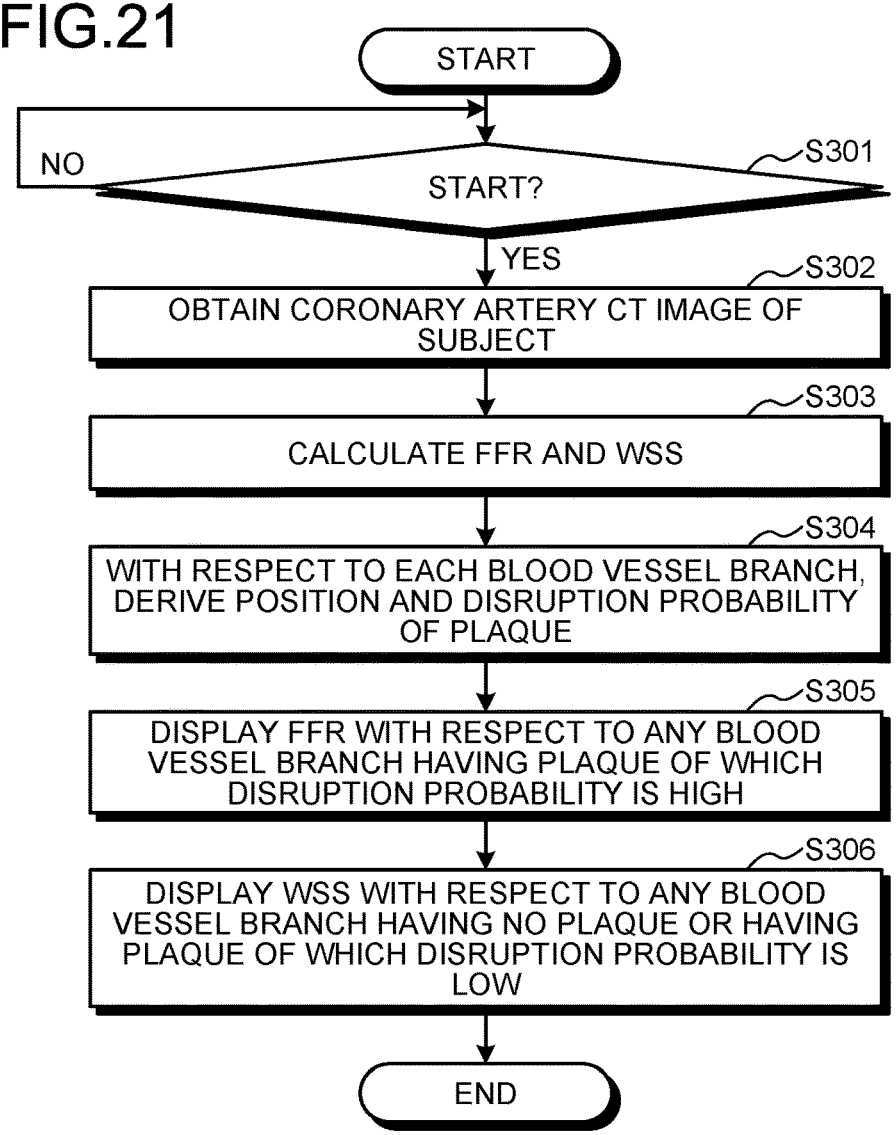
FIG. 21 is a flowchart illustrating a processing procedure of a process performed by processing functions included in processing circuitry of the medical image processing apparatus according to the third embodiment.

FIG. 21 is a flowchart illustrating a processing procedure of a process performed by the processing functions included in the processing circuitry 355 of the medical image processing apparatus 350 according to the third embodiment.

For example, as illustrated in FIG. 21, in the present embodiment, upon receipt of an instruction to start the process from the user via the input interface 153 (step S301: Yes), the obtaining function 155a obtains a coronary artery CT image of the subject from either the X-ray CT apparatus 110 or the medical image storage apparatus 120 (step S302). For example, this process is realized as a result of the processing circuitry 355 invoking and executing the program corresponding to the obtaining function 155a from the storage 152.

After that, on the basis of the coronary artery CT image of the subject obtained by the obtaining function 155a, the calculating function 155b calculates FFR and WSS as the information related to the blood flows of the coronary arteries (step S303). For example, this process is realized as a result of the processing circuitry 355 invoking and executing the program corresponding to the calculating function 155b from the storage 152.

Subsequently, on the basis of the coronary artery CT image of the subject obtained by the obtaining function 155a, the deriving function 355g derives, with respect to each of the blood vessel branches of the coronary arteries, the position and a rupture probability of the plaque occurring at the blood vessel branch (step S304). For example, this process is realized as a result of the processing circuitry 355 invoking and executing a program corresponding to the deriving function 355g from the storage 152.

After that, the display controlling function 355d displays the FFR calculated by the calculating function 155b, with respect to any of the blood vessel branches having plaque of which the rupture probability derived by the deriving function 355g is high (step S305) and displays the WSS calculated by the calculating function 155b, with respect to any of the blood vessel branches having no plaque or having plaque of which the rupture probability is low (step S306). For example, this process is realized as a result of the processing circuitry 355 invoking and executing a program corresponding to the display controlling function 355d from the storage 152.

As explained above, in the third embodiment, with respect to each of the blood vessel branches of the coronary arteries, the medical image processing apparatus 350 is configured to display the FFR and/or the WSS in accordance with the position and the rupture probability of the plaque occurring at the blood vessel branch. With this arrangement, when a diagnosing process is performed or a treatment plan is made in relation to cardiac diseases, it is possible to automatically display the WSS and the FFR with respect to each of the blood vessel branches of the coronary arteries. Consequently, according to the third embodiment, it is possible to reduce the trouble of the user at the time of performing the diagnosing process, making the treatment plan, or the like in relation to cardiac diseases.

A First Modification Example of the Third Embodiment

In the third embodiment described above, the example was explained in which one of the FFR and the WSS is displayed with respect to each of the blood vessel branches of the coronal arteries; however possible embodiments are not limited to this example.

For instance, as a first modification example of the third embodiment, the medical image processing apparatus 350 may be configured to display one of a representative FFR value and a representative WSS value, with respect to each of the blood vessel branches of the coronary arteries.

More specifically, with respect to any of the blood vessel branches having plaque of which the rupture probability derived by the deriving function 355g is high, the display controlling function 355d may display a first representative for one of the FFR and the WSS of the blood vessel branch. In contrast, with respect to any of the blood vessel branches having no plaque and any of the blood vessel branches having plaque of which the rupture probability is low, the display controlling function 355d may display a second representative value different from the first representative value for one of the FFR and the WSS of the blood vessel branch.

Figure 22:
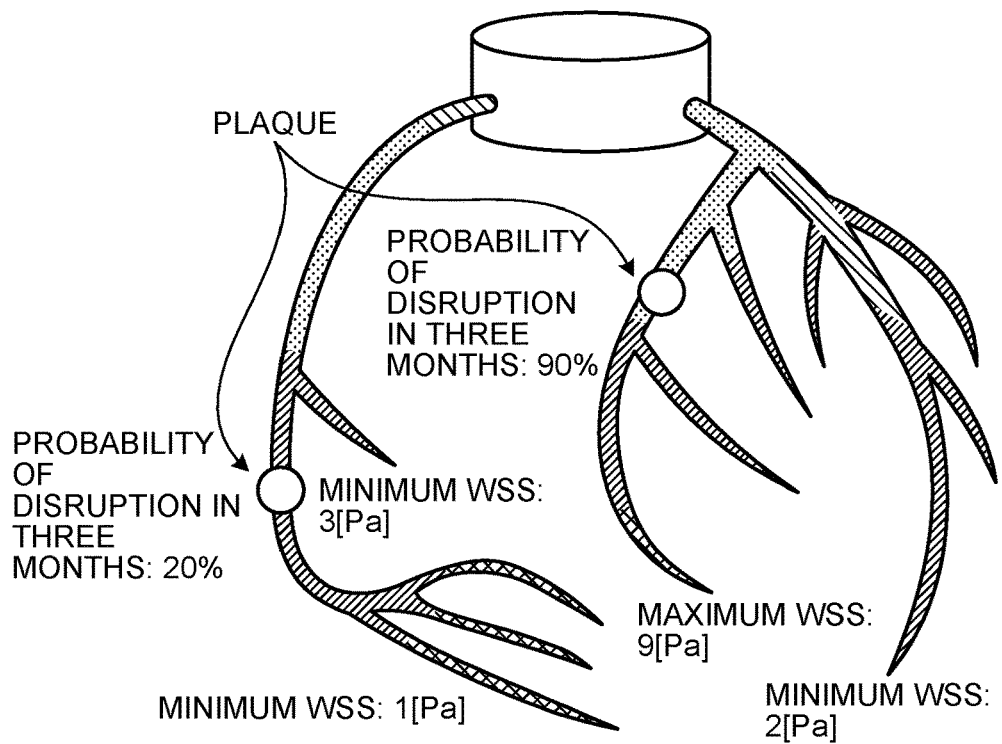
FIG. 22 is a drawing illustrating an example of information display performed by a display controlling function according to a first modification example of the third embodiment.

FIG. 22 is a drawing illustrating an example of the information display performed by the display controlling function 355d according to the first modification example of the third embodiment.

For example, as illustrated in FIG. 22, with respect to each of the blood vessel branches, the display controlling function 355d displays a representative WSS value (e.g., maximum WSS or minimum WSS) in a position corresponding to the blood vessel, in accordance with the position and the rupture probability of the plaque derived by the deriving function 355g. For example, it has been reported that low WSS has a correlation with development risk of plaque, whereas high WSS has a correlation with plaque rupture risk. Accordingly, for example, with respect to any of the blood vessel branches having plaque of which the rupture probability is high, the display controlling function 355d displays a maximum WSS value of the blood vessel branch in a position corresponding to the blood vessel branch. In contrast, with respect to any of the blood vessel branches having no plaque and any of the blood vessel branches having plaque of which the rupture probability is low, the display controlling function 355d displays a minimum WSS value of the blood vessel branch in a position corresponding to the blood vessel branch.

Although FIG. 22 illustrates the example of displaying the representative WSS values, the display controlling function 355d may display, for example, either a representative FFR value or both a representative FFR value and a representative WSS value, by using the same or a similar method.

A Second Modification Example of the Third Embodiment

Further, in the third embodiment described above, the example was explained in which the information (the FFR and/or the WSS) calculated from the coronary artery CT image is displayed; however, possible embodiments are not limited to this example.

For instance, as a second modification example of the third embodiment, the medical image processing apparatus 350 may be configured to display a medical image taken by another medical image diagnosis apparatus or information obtained from the medical image.

More specifically, with respect any of the blood vessel branches having plaque of which the rupture probability derived by the deriving function 355g is high, the display controlling function 355d may display one of: a medical image taken by a first medical image diagnosis apparatus; and information obtained from the medical image. In contrast, with respect any of the blood vessel branches having no plaque and any of the blood vessel branches having plaque of which the rupture probability is low, the display controlling function 355d may display one of: a medical image taken by a second medical image diagnosis apparatus different from the first medical image diagnosis apparatus; and information obtained from the medical image.

For example, with respect to any of the blood vessel branches having plaque of which the rupture probability is high, the display controlling function 355d displays a Hyper Intensity Plaque (HIP) image taken by an MRI apparatus, an intravascular ultrasound (IVUS) image taken by an ultrasound diagnosis apparatus, an intravascular Optical Coherence Tomography (OCT) image, or the like.

Figure 23:
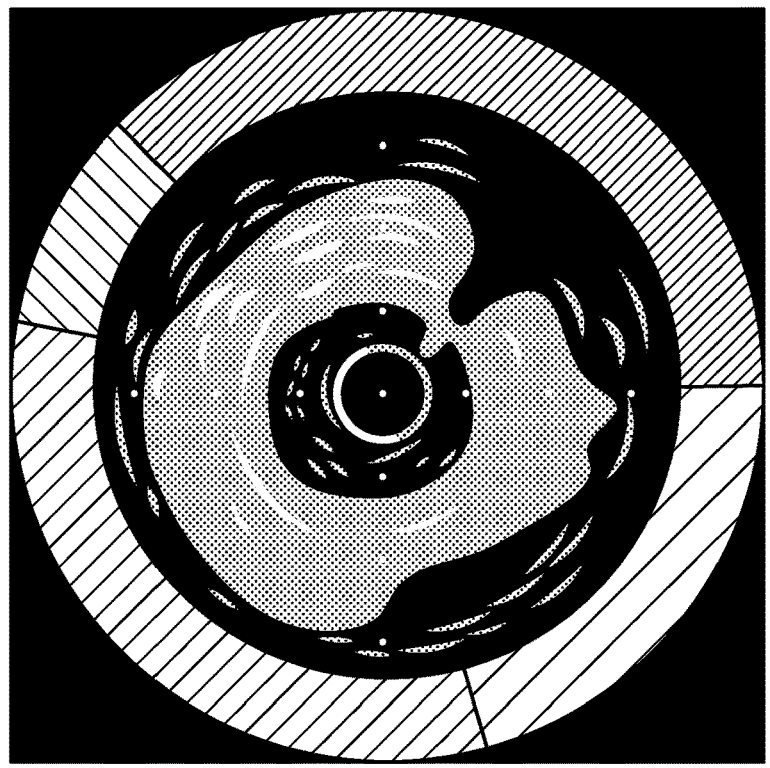
FIG. 23 is a drawing illustrating another example of the information display performed by the display controlling function according to the first modification example of the third embodiment.

FIG. 23 is a drawing illustrating another example of the information display performed by the display controlling function 355d according to the first modification example of the third embodiment.

For example, as illustrated in FIG. 23, when displaying the IVUS image or the intravascular OCT image, the display controlling function 355d may display, in a superimposed manner, colors each indicating a corresponding WSS or FFR value in various positions in the blood vessel so as to be positioned around the blood vessel rendered in the IVUS image or the intravascular OCT image.

Fourth Embodiment

In the first embodiment described above, the example was explained in which the FFR and/or the WSS are displayed in accordance with the degree of the disease related to the heart; however, possible embodiments are not limited to this example.

For instance, it is also acceptable to display FFR and/or WSS calculated on the basis of a medical image in a specific cardiac phase in accordance with the degree of a disease related to the heart. In the following sections, this example will be explained as a fourth embodiment. The following will describe configurations of a medical image processing system and a medical image processing apparatus according to the fourth embodiment, while a focus is placed on differences from the first embodiment. Some of the constituent elements that are the same will be referred to by using the same reference characters, and detailed explanations thereof will be omitted.

Figure 24:
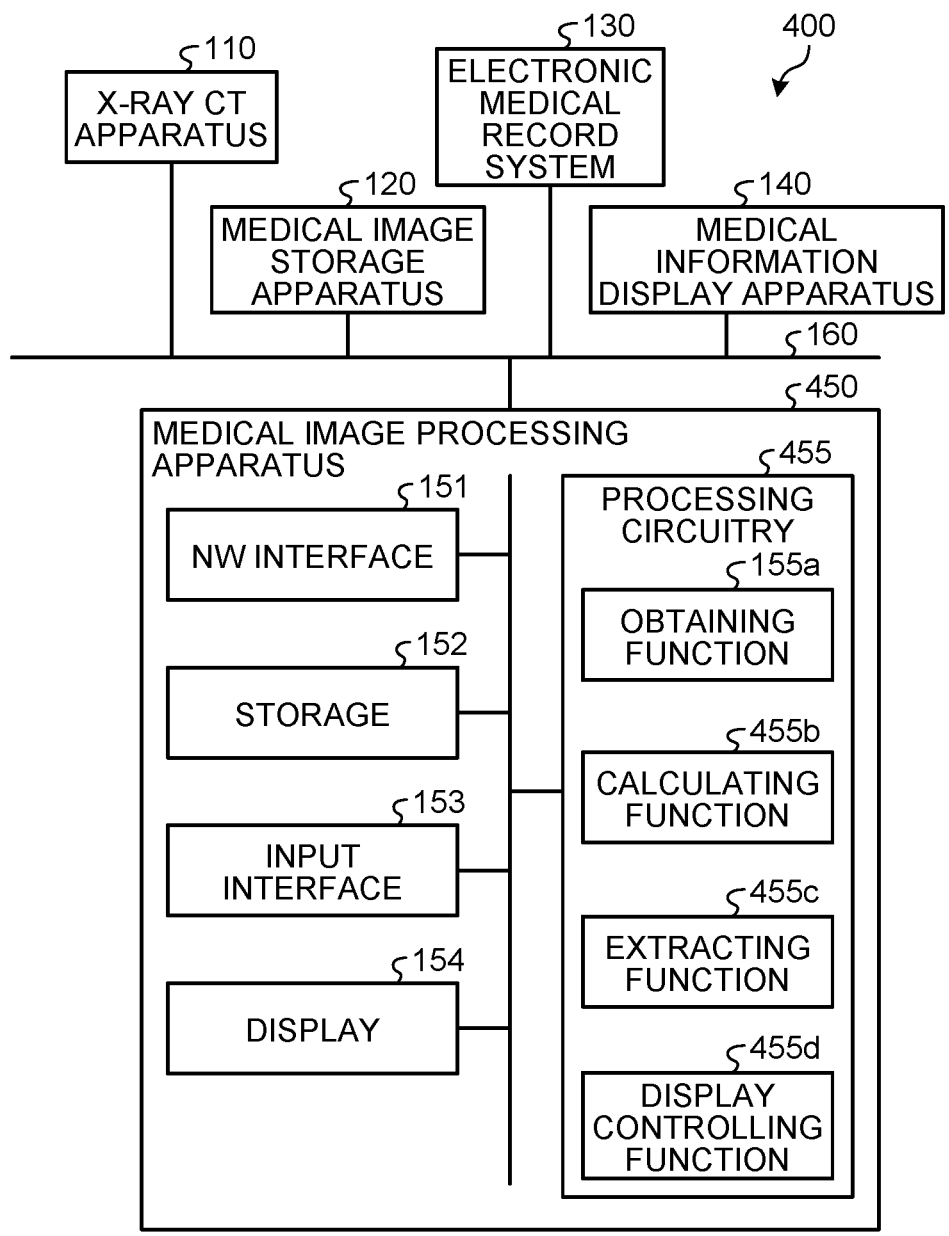
FIG. 24 is a diagram illustrating an exemplary configuration of a medical image processing system and a medical image processing apparatus according to a fourth embodiment.

FIG. 24 is a diagram illustrating an exemplary configuration of the medical image processing system and the medical image processing apparatus according to the fourth embodiment.

For example, as illustrated in FIG. 24, a medical image processing system 400 according to the present embodiment includes the X-ray CT apparatus 110, the medical image storage apparatus 120, the electronic medical record system 130, the medical information display apparatus 140, and a medical image processing apparatus 450. In the present example, the apparatuses and the system are communicably connected via the network 160.

The medical image processing apparatus 450 is configured to perform various types of image processing processes related to the subject. More specifically, the medical image processing apparatus 450 is configured to obtain the CT image from either the X-ray CT apparatus 110 or the medical image storage apparatus 120 via the network 160, to obtain the diagnosis/treatment data from the electronic medical record system 130, and to perform the various types of image processing processes by using the CT image and the diagnosis/treatment data. For example, the medical image processing apparatus 450 is realized by using a computer device such as a server or a workstation.

For example, the medical image processing apparatus 450 includes the NW interface 151, the storage 152, the input interface 153, the display 154, and processing circuitry 455.

Further, in the present embodiment, the processing circuitry 455 of the medical image processing apparatus 450 includes the obtaining function 155a, an extracting function 455c, a calculating function 455b, and a display controlling function 455d. In this situation, the extracting function 455c is an example of the extracting unit. The display controlling function 455d is an example of the display controlling unit.

The extracting function 455c is configured to extract a degree of a disease related to the heart from the coronary artery CT image of the subject obtained by the obtaining function 155a.

For example, as the degree of the disease related to the heart, the extracting function 455c extracts a degree of a myocardial bridge from the coronary artery CT image of the subject obtained by the obtaining function 155a.

More specifically, the extracting function 455c extracts a disease degree indicating the degree of a myocardial bridge, by analyzing the coronary artery CT image of the subject. In another example, the extracting function 455c extracts a presence probability of a myocardial bridge, as a disease degree indicating the degree of a myocardial bridge. In this situation, for example, the extracting function 455c may extract the presence probability on the basis of a distribution of CT values in various myocardial regions or may extract the presence probability by using a discriminator that has learned, in advance, characteristics of images in which a myocardial bridge is present and images in which no myocardial bridge is present through the machine learning technology.

In the present embodiment, the disease degree indicating the degree of the myocardial bridge extracted by the extracting function 455c does not necessarily have to be the presence probability. The disease degree may be expressed with any value, as long as the value is calculated by the user for the purpose of controlling the display of the FFR and the WSS described below. For example, the extracting function 455c may directly assign a value serving as a disease degree, on the basis of a result of a diagnosing process separately performed for the subject by the user such as a medical doctor or may extract, as a disease degree, a value indicating seriousness of the myocardial bridge on the basis of a perfusion index obtained from the coronary artery CT image.

In accordance with the disease degree extracted by the extracting function 455c, the calculating function 455b reconstructs a coronary artery CT image in a specific cardiac phase from the coronary artery CT image of the subject obtained by the obtaining function 155a and further calculates FFR and WSS on the basis of the reconstructed image.

More specifically, when the disease degree indicating the degree of the myocardial bridge extracted by the extracting function 455c is high, the calculating function 455b reconstructs a coronary artery CT image in the end-diastolic phase and calculates one or both of FFR and WSS on the basis of the reconstructed coronary artery CT image. In contrast, when the disease degree indicating the degree of the myocardial bridge extracted by the extracting function 455c is low, the calculating function 455b reconstructs a coronary artery CT image in the end-diastolic phase and a coronary artery CT image in the end-systolic phase and calculates one or both of FFR and WSS on the basis of each of the coronary artery CT images.

For example, in accordance with the presence probability of a myocardial bridge calculated by the extracting function 455c, the calculating function 455b reconstructs the coronary artery CT image in the specific cardiac phase and further calculates the FFR and the WSS on the basis of the coronary artery CT image. In this situation, for example, when the presence probability of a myocardial bridge is higher than a threshold value set in advance, the calculating function 455b reconstructs a coronary artery CT image corresponding to a point in time in the end-diastolic phase and further calculates FFR and WSS on the basis of the coronary artery CT image. In contrast, when the presence probability of a myocardial bridge is lower than the threshold value, the calculating function 455b reconstructs a coronary artery CT image corresponding to a point in time in the end-diastolic phase and a coronary artery CT image corresponding to a point in time in the end-systolic phase and further calculates FFR and WSS on the basis of each of the images.

The reason can be explained as follows: Normally, FFR and WSS are calculated from an image corresponding to a point in time in the end-systolic phase. However, in the state having a myocardial bridge (a state in which a coronary artery is embedded in the myocardia), high pressure is applied to the coronary artery from the myocardia positioned outside the coronary artery at the point in time in the end-systolic phase. Accordingly, there is a possibility that it may be impossible to calculate an FFR or WSS value based on impacts of the blood flows.

The display controlling function 455d causes the display 154 to display one or both of the FFR and the WSS calculated on the basis of the coronary artery CT image in the specific cardiac phase that was reconstructed by the calculating function 455b in accordance with the disease degree.

More specifically, when the disease degree indicating the degree of the myocardial bridge is high, the display controlling function 455d displays one or both of the FFR and the WSS calculated by the calculating function 455b on the basis of the coronary artery CT image in the end-diastolic phase. In contrast, when the disease degree indicating the degree of the myocardial bridge is low, the display controlling function 455d displays one or both of the FFR and the WSS calculated by the calculating function 455b on the basis of each of the coronary artery CT image in the end-diastolic phase and the coronary artery CT image in the end-systolic phase.

Figure 25:
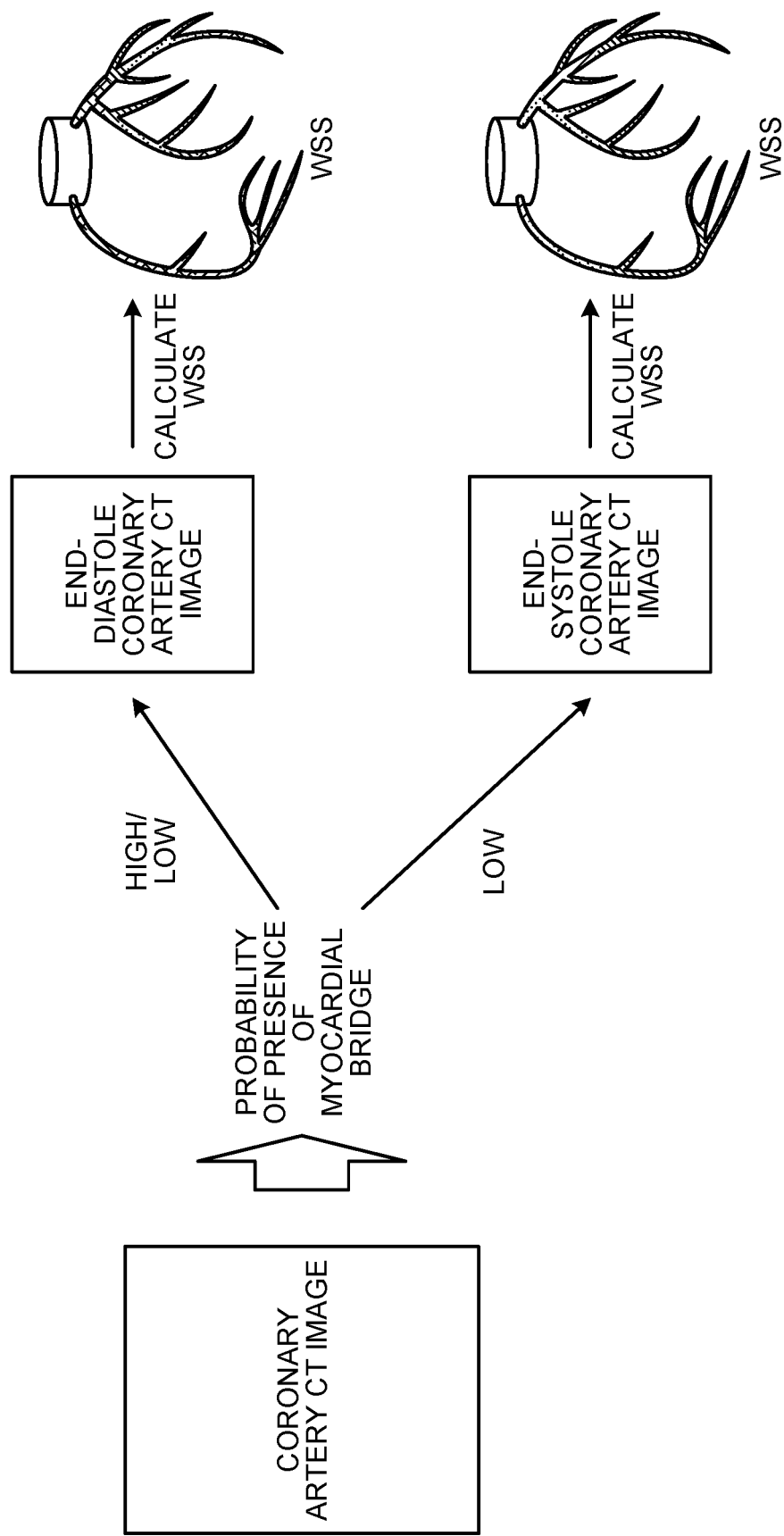
FIG. 25 is a drawing illustrating an example of information display performed by a display controlling function according to the fourth embodiment.

FIG. 25 is a drawing illustrating an example of the information display performed by the display controlling function 455d according the fourth embodiment.

For example, as illustrated in FIG. 25, the display controlling function 455d determines the type of information to be displayed on the display 154, on the basis of the presence probability of a myocardial bridge extracted by the extracting function 455c. In this situation, for example, when the presence probability of a myocardial bridge is higher than the threshold value set in advance, the display controlling function 455d determines the type of information to be displayed as the WSS calculated by the calculating function 455b from the coronary artery CT image corresponding to the point in time in the end-diastolic phase. In contrast, when the presence probability of a myocardial bridge is lower than the threshold value, the display controlling function 455d determines the type of information to be displayed as the WSS calculated from the coronary artery CT image corresponding to the point in time in the end-diastolic phase and the WSS calculated from the coronary artery CT image corresponding to the point in time in the end-systolic phase, by the calculating function 455b. Alternatively, for example, the display controlling function 455d may determine the type of information to be displayed either as the FFR or as both the FFR and the WSS.

After that, the display controlling function 455d causes the display 154 to display the determined type of information. For example, the display controlling function 455d causes the determined type of information to be displayed, similarly to the first embodiment and the modification examples thereof. In this situation, for example, when displaying both the WSS calculated from the coronary artery CT image corresponding to the point in time in the end-diastolic phase and the WSS calculated from the coronary artery CT image corresponding to the point in time in the end-systolic phase, the display controlling function 455d may display these pieces of information arranged side by side or may calculate the differences between the FFR values and the WSS values at the different points in time by performing a position aligning process so as to display an image indicating the differences in the FFR and WSS values.

Figure 26:
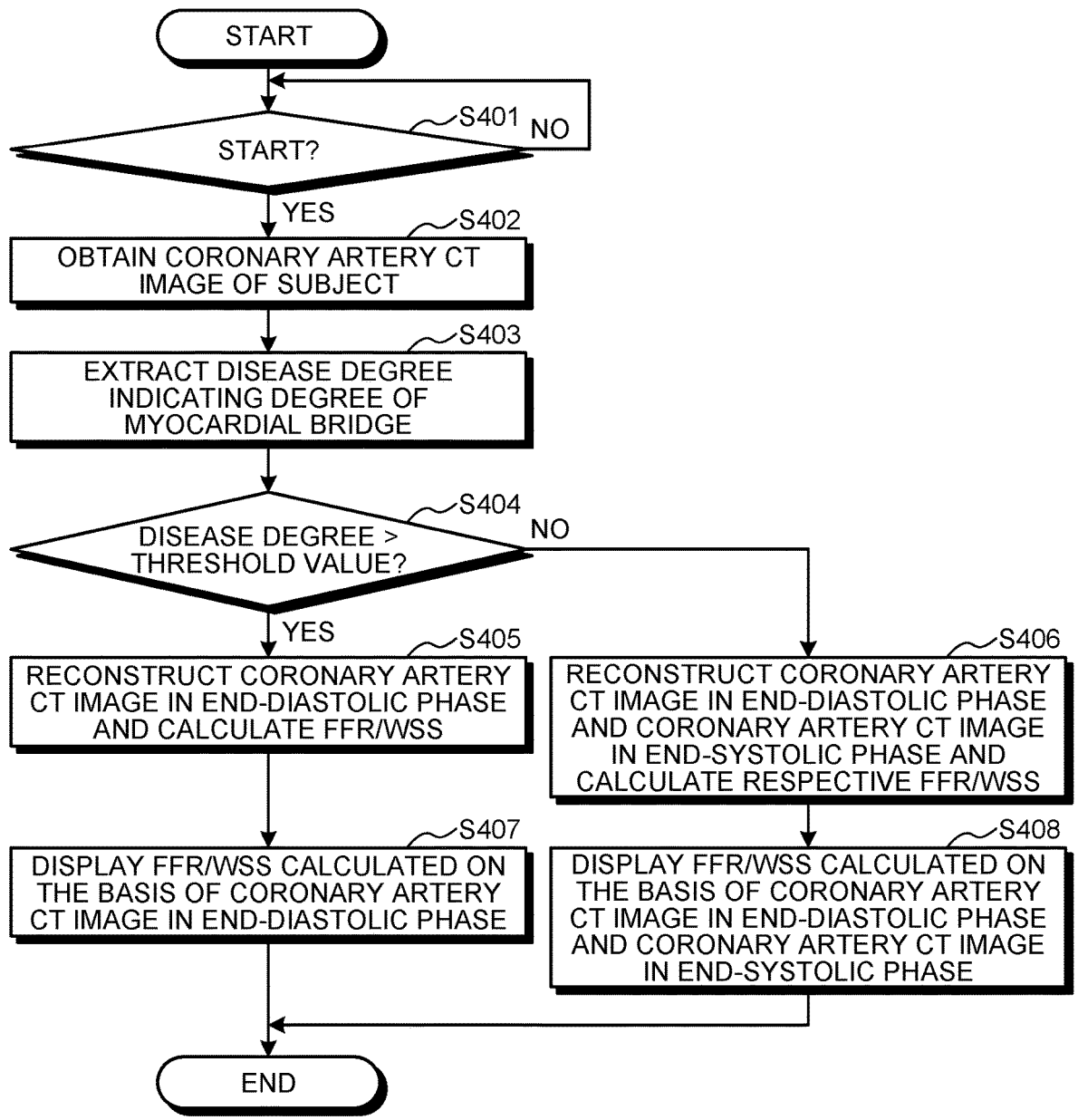
FIG. 26 is a flowchart illustrating a processing procedure of a process performed by processing functions included in processing circuitry of the medical image processing apparatus according to the fourth embodiment.

FIG. 26 is a flowchart illustrating a processing procedure of a process performed by the processing functions included in the processing circuitry 455 of the medical image processing apparatus 450 according to the fourth embodiment.

For example, as illustrated in FIG. 26, in the present embodiment, upon receipt of an instruction to start the process from the user via the input interface 153 (step S401: Yes), the obtaining function 155a obtains a coronary artery CT image of the subject from either the X-ray CT apparatus 110 or the medical image storage apparatus 120 (step S402). For example, this process is realized as a result of the processing circuitry 455 invoking and executing the program corresponding to the obtaining function 155a from the storage 152.

Subsequently, the extracting function 455c extracts a disease degree indicating the degree of a myocardial bridge from the coronary artery CT image of the subject obtained by the obtaining function 155a (step S403). For example, this process is realized as a result of the processing circuitry 455 invoking and executing a program corresponding to the extracting function 455c from the storage 152.

After that, when the disease degree indicating the degree of the myocardial bridge extracted by the extracting function 455c is high (step S404: Yes), the calculating function 455b reconstructs a coronary artery CT image in the end-diastolic phase and further calculates one or both of FFR and WSS on the basis of the reconstructed coronary artery CT image (step S405). On the contrary, when the disease degree indicating the degree of the myocardial bridge extracted by the extracting function 455c is low (step S404: No), the calculating function 455b reconstructs a coronary artery CT image in the end-diastolic phase and a coronary artery CT image in the end-systolic phase and further calculates one or both of FFR and WSS on the basis of each of the coronary artery CT images (step S406). For example, this process is realized as a result of the processing circuitry 455 invoking and executing a program corresponding to the calculating function 455b from the storage 152.

Subsequently, when the disease degree indicating the degree of the myocardial bridge is higher than the threshold value (step S404: Yes), the display controlling function 455d displays one or both of the FFR and the WSS calculated by the calculating function 455b on the basis of the coronary artery CT image in the end-diastolic phase (step S407). On the contrary, when the disease degree indicating the degree of the myocardial bridge is lower than the threshold value (step S404: No), the display controlling function 455d displays one or both of the FFR and the WSS calculated by the calculating function 455b on the basis of each of the coronary artery CT image in the end-diastolic phase and the coronary artery CT image in the end-systolic phase (step S408). For example, this process is realized as a result of the processing circuitry 455 invoking and executing a program corresponding to the display controlling function 455d from the storage 152.

As explained above, in the fourth embodiment, the medical image processing apparatus 450 is configured to display the FFR and/or the WSS calculated on the basis of the medical image in the specific cardiac phase, in accordance with the degree of the disease related to the heart. Accordingly, it is possible to automatically display the information in a cardiac phase suitable for each disease at the time of performing a diagnosing process and making a treatment plan in relation to cardiac diseases. Consequently, according to the fourth embodiment, it is possible to reduce the trouble of the user at the time of performing the diagnosing process, making the treatment plan, or the like in relation to cardiac diseases.

A First Modification Example of the Fourth Embodiment

In the fourth embodiment described above, the example was explained in which the cardiac phase of the coronary artery CT image in which the FFR and/or the WSS are to be displayed is determined in accordance with the degree of the myocardial bridge; however, possible embodiments are not limited to this example.

For instance, as a first modification example of the fourth embodiment, the medical image processing apparatus 450 may be configured to display FFR and/or WSS, in accordance with a degree of a valvular disease of each of the valves included in the heart valves.

For example, as a degree of a disease related to the heart, the extracting function 455c may extract the degree of a valvular disease of each of the valves included in the heart valves, from the coronary artery CT image of the subject obtained by the obtaining function 155a.

More specifically, the extracting function 455c may extract the disease degree indicating the degree of the valvular disease of each of the valves, by analyzing the coronary artery CT image of the subject. In another example, the extracting function 455c may extract a presence probability of a valvular disease, as the disease degree indicating the degree of the valvular disease. In this situation, for example, the extracting function 455c may extract the presence probability on the basis of a distribution of CT values with respect to each of the valves or may extract the presence probability by using a discriminator that has learned, in advance, characteristics of images in which a valvular disease is present and images in which no valvular disease is present, through the machine learning technology.

Further, in the present modification example, the disease degree indicating the degree of the valvular disease extracted by the extracting function 455c does not necessarily have to be the presence probability. The disease degree may be expressed with any value, as long as the value is calculated by the user for the purpose of controlling the display of the FFR and the WSS described below. For example, the extracting function 455c may directly assign a value serving as a disease degree on the basis of a result of a diagnosing process separately performed for the subject by the user such as a medical doctor or may extract, as a disease degree, a value indicating seriousness of the valvular disease on the basis of a perfusion index obtained from the coronary artery CT image.

Further, when the disease degree indicating a degree of a valvular disease of the aortic valve extracted by the extracting function 455c is high, the calculating function 455b reconstructs a coronary artery CT image in the end-systolic phase and further calculates one or both of FFR and WSS on the basis of the reconstructed coronary artery CT image. In contrast, when the disease degree indicating a degree of a valvular disease of the mitral valve extracted by the extracting function 455c is high, the calculating function 455b reconstructs a coronary artery CT image in the end-diastolic phase and further calculates one or both of FFR and WSS on the basis of the reconstructed coronary artery CT image.

For example, the calculating function 455b reconstructs the coronary artery CT image in the specific cardiac phase in accordance with the presence probability of the valvular disease of each of the valves extracted by the extracting function 455c and further calculates the FFR and the WSS on the basis of the coronary artery CT image. In this situation, for example, when the presence probability of the valvular disease of the aortic valve is higher than a threshold value set in advance, the calculating function 455b reconstructs the coronary artery CT image at a point in time in the end-systolic phase and further calculates the FFR and the WSS on the basis of the coronary artery CT image. In contrast, when the presence probability of the valvular disease of the mitral valve is lower than the threshold value, the calculating function 455b reconstructs the coronary artery CT image at a point in time in the end-diastolic phase and further calculates the FFR and the WSS on the basis of the coronary artery CT image. These processes are performed to make it easier to evaluate impacts in the FFR and WSS values from the opening and closing of various types of valves.

Further, when the disease degree indicating the degree of the valvular disease of the aortic valve is high, the display controlling function 455d displays one or both of the FFR and the WSS calculated by the calculating function 455b on the basis of the coronary artery CT image in the end-systolic phase. In contrast, when the disease degree indicating the degree of the valvular disease of the mitral valve is low, the display controlling function 455d displays one or both of the FFR and the WSS calculated by the calculating function 455b on the basis of the coronary artery CT image in the end-diastolic phase.

Figure 27:
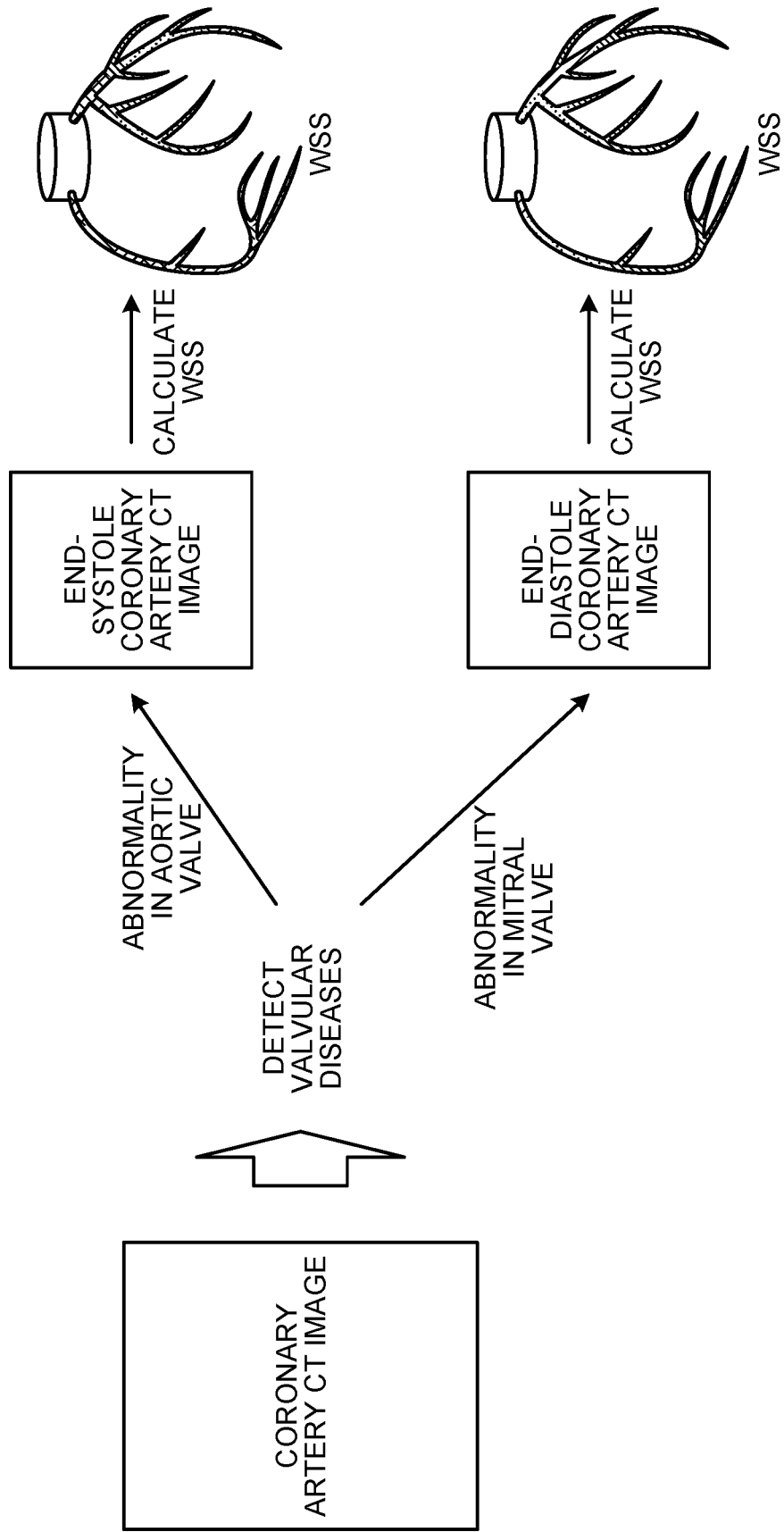
FIG. 27 is a drawing illustrating an example of information display performed by a display controlling function according to a first modification example of the fourth embodiment.

FIG. 27 is a drawing illustrating an example of the information display performed by the display controlling function 455d according to the first modification example of the fourth embodiment.

For example, as illustrated in FIG. 27, on the basis of the presence probability of the valvular disease of each of the valves extracted by the extracting function 455c, the display controlling function 455d determines the type of information to be displayed on the display 154. In this situation, for example, when the presence probability of the valvular disease of the aortic valve is higher than the threshold value set in advance (an aortic valve abnormality), the display controlling function 455d determines the type of information to be displayed as the WSS calculated by the calculating function 455b from the coronary artery CT image corresponding to the point in time in the end-systolic phase. In contrast, when the presence probability of the valvular disease of the mitral valve is higher than the threshold value set in advance (a mitral valve abnormality), the display controlling function 455d determines the type of information to be displayed as the WSS calculated by the calculating function 455b from the coronary artery CT image corresponding to the point in time in the end-diastolic phase. Alternatively, for example, the calculating function 455b may determine the type of information to be displayed either as the FFR or as both the FFR and the WSS.

After that, the display controlling function 455d causes the display 154 to display the determined type of information. For example, the display controlling function 455d causes the determined type of information to be displayed similarly to the first embodiment and the modification examples thereof.

In the fourth embodiment described above, the example was explained in which the judgment related to displaying the FFR and/or the WSS is made in accordance with the degree of the myocardial bridge or the degree of the valvular disease of each of the valves included in the heart valves; however, possible embodiments are not limited to this example. It is acceptable to make the judgment related to displaying the FFR and/or WSS in accordance with any state, as long as the state allows a cardiac phase used in the reconstruction to be determined on the basis of the original image or information obtained in advance (prior to the calculation of the FFR and/or the WSS) such as the patient information, for example.

Fifth Embodiment

Further, for example, in the first embodiment described above, the example was explained in which the WSS is displayed by using the image indicating the coronary arteries; however, possible embodiments are not limited to this example.

For instance, the medical image processing apparatus 150 may be configured to display a relation between distance from a reference position at a predetermined position along a coronary artery and magnitude of the WSS at the predetermined position. It may be displayed by using a graph. The following will describe configurations of a medical image processing system and a medical image processing apparatus according to the fifth embodiment, while a focus is placed on differences from the first embodiment. Some of the constituent elements that are the same will be referred to by using the same reference characters, and detailed explanations thereof will be omitted.

In the present embodiment, for example, when the degree of a coronary artery disease extracted by the extracting function 155c is low, the display controlling function 155d causes the display 154 to display a graph having a vertical axis that expresses magnitude of the WSS and a horizontal axis that expresses distance from a reference position along the coronary artery and thereby indicating a relation between the magnitude of the wall shear stress and the distance. In addition, the display controlling function 155d causes the display 154 to display, together with the graph, information indicating a range of the distance in which a third index value related to the blood vessel exhibits abnormal values.

In this situation, for example, the third index value is an index value representing a lesion part occurring in the coronary artery. For example, the third index value is a CT value of a wall of the coronary artery, and is determined as abnormal value when indicating a CT value within a range representing plaque, calcium, or the like.

Figure 28:
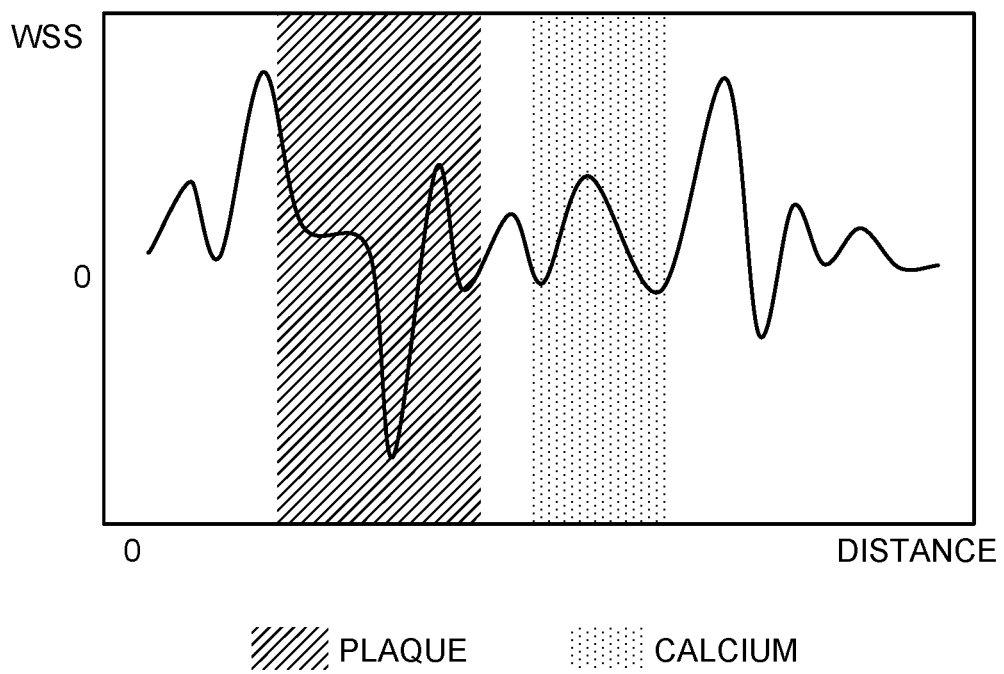
FIG. 28 is a drawing illustrating an example of information display performed by a display controlling function according to a fifth embodiment.

FIG. 28 is a drawing illustrating an example of the information display performed by the display controlling function 155d according to the fifth embodiment.

For example, as illustrated in FIG. 28, on the basis of values of the WSS calculated by the calculating function 155b, the display controlling function 155d displays a graph having a vertical axis that expresses the magnitude of the WSS and a horizontal axis that expresses the distance from the reference position along the coronary artery and thereby indicating the relation between the magnitude of the WSS and the distance by a curve.

Further, the display controlling function 155d displays the information indicating the range of the distance along the coronary artery in which the third index value exhibits the abnormal values, so as to be superimposed on a position indicating the distance on the graph.

For example, as illustrated in FIG. 28, on the basis of the coronary artery CT image of the subject obtained by the obtaining function 155a, the display controlling function 155d displays information indicating distance from the reference point along the coronary artery at a position on the coronary artery having a CT value representing plaque and information indicating distance from the reference point along the coronary artery at a position on the coronary artery having a CT value representing calcium, so as to be superimposed on positions indicating the distances on the graph.

For example, the display controlling function 155d may display the information indicating distance from the reference point along the coronary artery at a position on the coronary artery having a CT value representing plaque and the information indicating distance from the reference point along the coronary artery at a position on the coronary artery having a CT value representing calcium in mutually-different display modes. For example, the display controlling function 155d displays the regions indicating the ranges by using mutually-different colors, patterns, or textures.

Although the example was explained above in which the information indicating the range in which the third index value exhibits the abnormal values is displayed so as to be superimposed on the graph, possible embodiments are not limited to this example. For instance, the display controlling function 155d may display the information indicating the range in which the third index value exhibits the abnormal values, so as to be arranged above or below the graph corresponding to the position of the distance from the reference point along the coronary artery.

Further, although the example was explained above in which the third index value is an index value representing the lesion part occurring in the coronary artery, possible embodiments are not limited to this example.

For instance, the third index value may be an index value calculated from changes in blood pressure, the blood flow, the shape, or the position of the coronary artery. For example, the third index value may be a value of a fluid parameter indicating FFR, pressure, a flow rate, or the like. In other examples, the third index value may be a value of a shape parameter indicating a curvature, a stenosis percentage, the outside diameter, the inside diameter, the cross-sectional area, or the like of the blood vessel. In another example, the third index value may be a value indicating a movement amount of the blood vessel in conjunction with the movement of the heart.

Further, in yet another example, the third index value may be an index value predicted by applying virtual surgery or treatment to the coronary artery by using the coronary artery CT image. For example, the third index value may be a value of a fluid parameter or a shape parameter after the surgery or after the treatment that is predicted by applying a virtual surgery or treatment simulation while using the coronary artery CT image.

In that situation, for example, the display controlling function 155d receives, from the operator, a position in which the treatment device such as a stent or a balloon is arranged with the coronary artery, while using the coronary artery CT image, and thereby displays information indicating a range in which the treatment device is arranged, so as to be superimposed on the graph indicating the relation between distance from a reference position at a predetermined position along a coronary artery and magnitude of the WSS at the predetermined position. In addition, the display controlling function 155d displays, so as to be further imposed on the WSS graph, information indicating a range in which the fluid parameter or the shape parameter exhibits abnormal values after the treatment device is arranged and which is calculated by performing the surgery simulation or the treatment simulation.

Modification Examples of the Fifth Embodiment

In the fifth embodiment described above, the example was explained in which the graph indicating the relation between distance from a reference position at a predetermined position along a coronary artery and magnitude of the WSS at the predetermined position is displayed at the single point in time; however, possible embodiments are not limited to this example.

For instance, when the degree of the coronary artery disease extracted by the extracting function 155c is low, the display controlling function 155d may generate, with respect to each of a plurality of mutually-different points in time, a graph having a vertical axis that expresses magnitude of the WSS and a horizontal axis that expresses distance from a reference position along the coronary artery and thereby indicating a relation between the magnitude of the WSS and the distance, and cause the display 154 to display the graph with respect to each of the plurality of mutually-different points in time.

Figure 29:
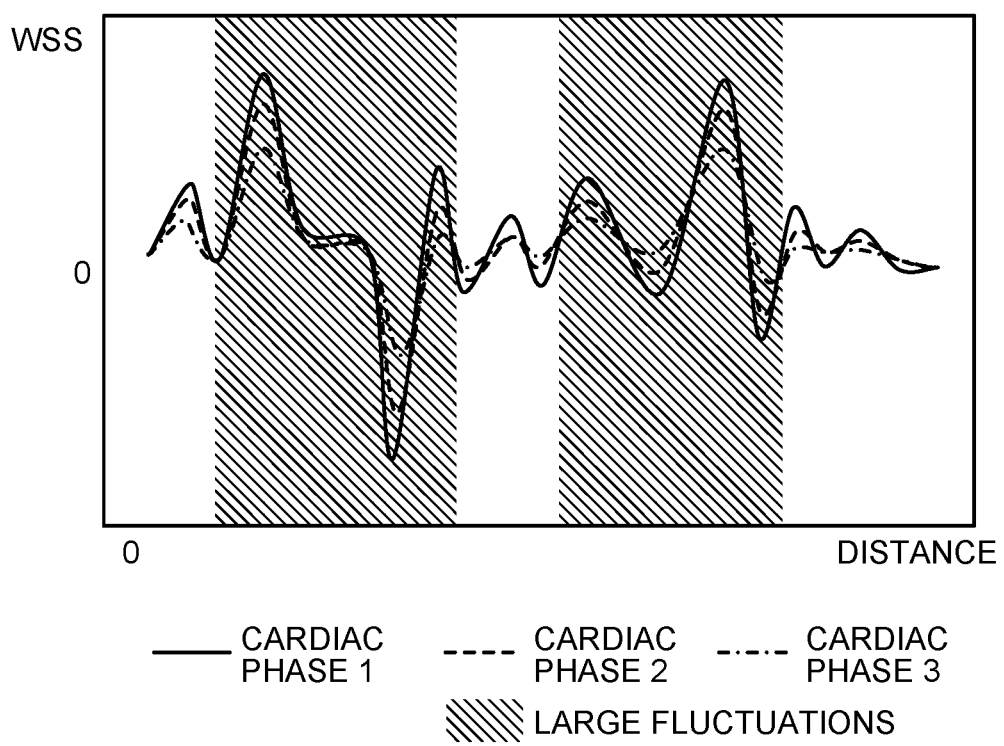
FIG. 29 is a drawing illustrating an example of information display performed by a display controlling function according to a modification example of the fifth embodiment.

FIG. 29 is a drawing illustrating an example of the information display performed by the display controlling function 155d according to the modification example of the fifth embodiment.

For example, as illustrated in FIG. 29, on the basis of the WSS calculated by the calculating function 155b from coronary artery CT images in a plurality of temporal phases, the display controlling function 155d generates, with respect to each of a plurality of mutually-different cardiac phases included in one heartbeat, a graph having a vertical axis that expresses magnitude of the WSS and a horizontal axis that expresses distance from a reference position along the coronary artery and thereby indicating a relation between the magnitude of the WSS and the distance, and superimposes and displays the graphs.

In addition, for example, the display controlling function 155d further displays information indicating a range in which temporal fluctuation amounts of the WSS exceed a threshold value in the distance from the reference position along the coronary artery, together with the graph. For example, the display controlling function 155d displays the information indicating the range in which the temporal fluctuation amounts of the WSS exceed the threshold value in the distance from the reference position along the coronary artery, so as to be superimposed on the graph by aligning the positions indicating the distance.

For example, as the information indicating the range in which the temporal fluctuation amounts of the WSS exceed the threshold value, the display controlling function 155d displays a region indicating the range by using a display mode determined in advance. For example, the display controlling function 155d displays the region indicating the range by using a color, a pattern, or a texture determined in advance.

In this situation, for example, similarly to the fifth embodiment described above, the display controlling function 155d may further display the information indicating the range of the distance from the reference position along the coronary artery in which the third index value related to the blood vessel exhibits abnormal values, together with the graph.

Further, in the explanation above, the example was explained in which the information indicating the changes in the WSS is displayed with respect to each of the plurality of mutually-different cardiac phases included in the one heartbeat, serving as the plurality of mutually-different points in time; however, possible embodiments are not limited to this example. For instance, the plurality of mutually-different points in time may be points in time before and after surgery or treatment (e.g., a drug therapy) or may be points in time at time intervals (e.g., fixed intervals such as one month apart) determined in advance.

Further, in the fifth embodiment and the modification examples above, the example was explained in which the information indicating the changes in the WSS is displayed with respect to the one blood vessel; however, possible embodiments are not limited to this example. For instance, the information indicating the changes in the WSS may be displayed with respect to a plurality of blood vessels. In that situation, for example, the plurality of blood vessels may be a plurality of blood vessel branches included in one or more coronary arteries.

In that situation, for example, with respect to the plurality of blood vessels, the display controlling function 155d may display, for each blood vessel, information such as the WSS and/or the third index value, by using the display method explained in any of the fifth embodiment and the modification examples above. In that situation, for example, the display controlling function 155d displays pieces of information indicating the changes in the WSS with respect to the plurality of blood vessels, so as to be arranged side by side by using a plurality of graphs or so as to be arranged on top of each other by using a single graph.

Further, in any of the fifth embodiment and the modification examples described above, for example, the display controlling function 155d may further display cross-sectional images of the coronary artery corresponding to the position of the distance from the reference position along the coronary artery. In this situation, for example, the cross-sectional images may be curved MPR images of the coronary artery.

Sixth Embodiment

Further, the embodiments and the modification examples described above may each be implemented alone or may each be implemented as being combined with one or more other embodiments and/or modification examples, as appropriate.

For example, when a predetermined condition is satisfied after the FFR and/or the WSS are displayed by using a method described in any of the embodiments and the modification examples described above, it is acceptable to display the FFR and/or the WSS by using another method either automatically or according to an instruction from the user.

In a specific example, in the first embodiment, when the disease degree indicating the degree of a coronary artery disease is higher than the first threshold value, the display controlling function 155d may receive, from the user, an instruction to display the FFR and/or the WSS by using a method described in any of the first to the sixth modification examples, while the FFR is being displayed. Further, the display controlling function 155d may further display the FFR and/or the WSS by using the method instructed by the user.

Further, for example, in the second embodiment, when the imaging time of the coronary artery CT image was before the subject was treated, the display controlling function 255d may receive, from the user, an instruction to display the FFR and/or the WSS by using a method described in any of the first to the fourth modification examples, while displaying the predicted FFR and/or the predicted WSS. Further, the display controlling function 255d may further display the FFR and/or the WSS by using the method instructed by the user.

Further, for example, in the third embodiment, while displaying the FFR and/or the WSS with respect to each of the blood vessel branches of the coronary arteries, the display controlling function 355d may receive, from the user, an instruction to display the FFR and/or the WSS with respect to each of the blood vessel branches by using a method described in any of the first and the second modification examples. After that, the display controlling function 355d may further display the FFR and/or the WSS by using the method instructed by the user.

Further, for example, in the fourth embodiment, when the disease degree indicating the degree of the myocardial bridge is higher than the threshold value, the display controlling function 455d may receive, from the user, an instruction to display the FFR and/or the WSS by using the method described in the first modification example, while displaying the FFR and/or the WSS calculated on the basis of the coronary artery CT image in the end-diastolic phase. Further, upon receipt of the instruction from the user, the display controlling function 455d may further display the FFR and/or the WSS, in accordance with the disease degree indicating the degree of a valvular disease of each of the valves.

Further, for example, while displaying the FFR and/or the WSS by using a method described in any of the first to the fifth embodiments, the display controlling function may receive, from the user, an instruction to display the FFR and/or the WSS by using a method described in any of the other embodiments and the modification examples. In that situation also, the display controlling function may further display the FFR and/or the WSS by using the method instructed by the user.

In any of the examples described above, when a predetermined condition is satisfied while displaying the FFR and/or the WSS by using any of the methods, the display controlling function may further display the FFR and/or the WSS either automatically or by using another predetermined method.

Seventh Embodiment

In the embodiments and the modification examples described above, the example was explained in which the medical image processing apparatus is configured to cause the display included therein to display the FFR and the WSS; however, possible embodiments are not limited to this example.

For instance, a medical information display apparatus may obtain, from the medical image processing apparatus via a network, and display the FFR and the WSS.

More specifically, in the present embodiment, the medical image processing apparatus is configured to extract a degree of a coronary artery disease from a medical image, in response to a request transmitted thereto from the medical information display apparatus. On the basis of the medical image, as information related to blood flows, the medical image processing apparatus calculates FFR when the degree of the coronary artery disease is high and calculates WSS when the degree of the coronary artery disease is low. Further, the medical information display apparatus obtains the information related to the blood flows from the medical image processing apparatus and causes a display included therein to display the obtained information.

In that situation, for example, the medical image processing apparatus and the medical information display apparatus may be realized as a client-server system in which the medical image processing apparatus serves as a server, whereas a medical information display apparatus serves as a client.

Other Embodiments

In the embodiments and the modification examples described above, the example was explained in which the coronary artery CT image is used as the medical image; however, possible embodiments are not limited to this example. For instance, it is acceptable to use any type of medical image, as long as the type of image makes it possible to calculate the shape of the blood vessel and flow information such as the flow rate of the blood. For example, it is acceptable to use an ultrasound image obtained from an ultrasound diagnosis image or an MR image obtained by an MRI apparatus. Further, the targeted site does not necessarily have to be blood vessels of the heart and may be blood vessels in another site such as cerebral blood vessels or hepatic arteries or portal veins.

Further, in the embodiments and the modification examples described above, the example was explained in which the FFR is used as the first index value displayed as being switched from or at the same time with the WSS; however, possible embodiments are not limited to this example. It is acceptable to use any index value, as long as the index value is related to blood vessels and calculated from one of blood pressure and blood flows, for example.

According to at least one aspect of the embodiments and the modification examples described above, it is possible to reduce the trouble of the user, because it is possible to display, for example, the WSS and the various types of information related to the blood flows, at an appropriate point in time or by using an appropriate display mode. Further, for example, because it is possible to automatically change the information to be displayed, in accordance with the characteristics of the coronary artery CT image serving as an image to be analyzed, the user is able to obtain necessary information when the information is needed. Further, for example, because it is possible to display the WSS calculated from the coronary artery CT image, together with the different type of information related to the coronary arteries, it is possible to more appropriately assist the medical doctor in performing diagnosing processes, making treatment plans, assessing advantageous effects of treatments, and the like.

In the embodiments and the modification examples described above, the example was explained in which the extracting unit, the display controlling unit, the identifying unit, the predicting unit, and the deriving unit of the present disclosure are realized as the extracting function, the display controlling function, the identifying function, the predicting function, and the deriving function included in the processing circuitry, respectively; however, possible embodiments are not limited to this example. For instance, instead of being realized as the extracting function, the display controlling function, the identifying function, the predicting function, and the deriving function described in the embodiments, the functions of the extracting unit, the display controlling unit, the identifying unit, the predicting unit, and the deriving unit of the present disclosure may be realized by only hardware, only software, or a combination of hardware and software.

Further, the term "processor" used in the above explanations of the embodiments denotes, for example, a Central Processing Unit (CPU), a Graphics Processing Unit (GPU), or a circuit such as an Application Specific Integrated Circuit (ASIC) or a programmable logic device (e.g., a Simple Programmable Logic Device [SPLD], a Complex Programmable Logic Device [CPLD], or a Field Programmable Gate Array [FPGA]). In this situation, instead of saving the programs in the storage, it is also acceptable to directly incorporate the programs into the circuits of the processors. In that situation, the processors realize the functions by reading and executing the programs incorporated in the circuits thereof. Further, the processors in the present embodiments do not each necessarily have to be structured as a single circuit. It is also acceptable to structure one processor by combining together a plurality of independent circuits, so as to realize the functions thereof.

In this situation, the programs executed by the one or more processors are provided as being incorporated, in advance, into a Read-Only Memory (ROM), a storage, or the like. Alternatively, the programs may be provided as being recorded on a computer-readable non-transitory storage medium such as a Compact Disk Read-Only Memory (CD-ROM), a Flexible Disk (FD), a Compact Disk Recordable (CD-R), a Digital Versatile Disk (DVD), or the like, in a file in a format that is installable or executable for these devices. Further, the programs may be stored in a computer connected to a network such as the Internet, so as to be provided or distributed as being downloaded via the network. For example, the programs are structured with modules including the processing functions described above. In the actual hardware, as a result of a CPU reading and executing the programs from a storage medium such as a ROM, the modules are loaded into a main storage apparatus so as to be generated in the main storage apparatus.

Further, the constituent elements of the apparatuses in the drawings of the above embodiments and modification examples are based on functional concepts. Thus, it is not necessarily required to physically configure the constituent elements as indicated in the drawings. In other words, specific modes of distribution and integration of the apparatuses are not limited to those illustrated in the drawings. It is acceptable to functionally or physically distribute or integrate all or a part of the apparatuses in any arbitrary units, depending on various loads and the status of use. Further, all or an arbitrary part of the processing functions performed by the apparatuses may be realized by a CPU and a program analyzed and executed by the CPU or may be realized as hardware using wired logic.

Further, with regard to the processes explained in the above embodiments and modification examples, it is acceptable to manually perform all or a part of the processes described as being performed automatically. Conversely, by using a publicly-known method, it is also acceptable to automatically perform all or a part of the processes described as being performed manually. Further, unless noted otherwise, it is acceptable to arbitrarily modify any of the processing procedures, the controlling procedures, specific names, and various information including various types of data and parameters that are presented in the above text and the drawings.

According to at least one aspect of the embodiments described above, it is possible to reduce the trouble of the user at the time of performing a diagnosing process, making a treatment plan, or the like, in relation to cardiac diseases.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

With respect to the above embodiments, the following notes are disclosed as one aspect and selective features of the invention.

Note 1:
A medical image processing apparatus, comprising:
an extracting unit configured to extract a degree of a disease related to a heart from a medical image; and
a display controlling unit configured to display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated on a basis of the medical image.

Note 2:
The display controlling unit may be further configured to:
display, when a disease degree indicating the degree of the disease related to the heart is higher than a first threshold value, the first index value;
display, when the disease degree indicating the degree of the disease related to the heart is lower than a second threshold value smaller than the first threshold value, the second index value; and
display, when the disease degree indicating the degree of the disease related to the heart falls between the first threshold value and the second threshold value, the first index value and the second index value.

Note 3:
The display controlling unit may be further configured to:
display, when the disease degree indicating the degree of the disease related to the heart is high, one or both of the first index value being one-dimensional and the second index value being one-dimensional; and
display, when the disease degree indicating the degree of the disease related to the heart is low, one or both of the first index value being three-dimensional and the second index value being three-dimensional.

Note 4:
The display controlling unit may be further configured to:
simultaneously display the first index value and the second index value;
make, when the disease degree indicating the degree of the disease related to the heart is high, a display region of the first index value larger than a display region of the second index value, and
make, when the disease degree indicating the degree of the disease related to the heart is low, the display region of the second index value larger than the display region of the first index value.

Note 5:
The display controlling unit may be further configured to display the first index value and the second index value in mutually-different display modes.

Note 6:
The display controlling unit may be further configured to display an image indicating the blood vessel and displays, within the image, the first index value and the second index value arranged on top of each other or side by side.

Note 7:

The display controlling unit may be further configured to:
receive, from a user, an operation to select a type of information to be displayed; and
display one or both of the first index value and the second index value in accordance with the received operation.

Note 8:

The display controlling unit may be further configured to:
receive, from the user, an operation to switch display between the first index value and the second index value; and
switch from a state in which one of the first index value and the second index value is displayed into a state in which the other is displayed in accordance with the received operation.

Note 9:

The medical image processing apparatus may further comprise:
an identifying unit configured to identify whether a time at which the medical image was taken was before a subject was treated or after the subject was treated; and
a predicting unit configured to calculate, when the time at which the medical image was taken is identified as before the subject was treated, one or both of a first predicted index value being the first index value after the treatment and a second predicted index value being the second index value after the treatment, by applying virtual treatment to the blood vessel while using the medical image, wherein
the display controlling unit is further configured to display, when the time at which the medical image was taken is identified as before the subject was treated, one or both of the first predicted index value and the second predicted index value.

Note 10:

The display controlling unit may be further configured to:
display, when the time at which the medical image was taken is identified as before the subject was treated, one or both of the first index value and the second index value calculated on the basis of the medical image and one or both of the first predicted index value and the second predicted index value; and
display, when the time at which the medical image was taken is identified as after the subject was treated, one or both of the first index value and the second index value calculated on the basis of the medical image.

Note 11:

The display controlling unit may be further configured to:
displays, when the time at which the medical image was taken is identified as before the subject was treated, one or both of the first index value being three-dimensional and the second index value being three-dimensional, and
display, when the time at which the medical image was taken is identified as after the subject was treated, one or both of the first index value being one-dimensional and the second index value being one-dimensional.

Note 12:

The predicting unit may be further configured to calculate, after the display controlling unit determines to display one or both of the first predicted index value and the second predicted index value, the one or both of the first predicted index value and the second predicted index value.

Note 13:

The predicting unit may be further configured to:
receive, from the user, an operation to input a parameter used at a time of applying the virtual treatment; and
calculate one or both of the first predicted index value and the second predicted index value by using the received parameter.

Note 14:

The display controlling unit may be further configured to display, when the time at which the medical image was taken is identified as after the subject was treated, one or both of the first index value and the second index value calculated on a basis of the medical image before the treatment and one or both of the first index value and the second index value calculated on a basis of the medical image after the treatment.

Note 15:

The medical image processing apparatus may further comprise:
a deriving unit configured to derive, with respect to each of blood vessel branches of a coronary artery, a position and a rupture probability of plaque occurring at the blood vessel branch, on the basis of the medical image, wherein
the display controlling unit is further configured to display, with respect to each of the blood vessel branches, one of the first index value and the second index value in accordance with the position and the rupture probability of the plaque.

Note 16:

The display controlling unit may be further configured to:
display the first index value with respect to any of the blood vessel branches having the plaque of which the rupture probability is high; and
display the second index value with respect to any of the blood vessel branches having no plaque or having the plaque of which the rupture probability is low.

Note 17:

The display controlling unit may be further configured to:
displays, with respect to any of the blood vessel branches having the plaque of which the rupture probability is high, a first representative value for one of the first index value and the second index value of the blood vessel branch; and
display, with respect to any of the blood vessel branches having no plaque and any of the blood vessel branches having the plaque of which the rupture probability is low, a second representative value different from the first representative value, for one of the first index value and the second index value of the blood vessel branch.

Note 18:

The display controlling unit may be further configured to:
display, with respect to any of the blood vessel branches having the plaque of which the rupture probability is high, one of a medical image taken by a first medical image diagnosis apparatus and information obtained from the taken medical image; and
display, with respect to any of the blood vessel branches having no plaque and any of the blood vessel branches having the plaque of which the rupture probability is low, one of a medical image taken by a second medical image diagnosis apparatus different from the first medical image diagnosis apparatus and information obtained from the taken medical image.

Note 19:

The display controlling unit may be further configured to display one or both of the first index value and the second index value calculated on a basis of the medical image that is in a specific cardiac phase and is reconstructed in accordance with the degree of the disease related to the heart.

Note 20:

The extracting unit may be further configured to extract a degree of a myocardial bridge, as the degree of the disease related to the heart, and the display controlling unit is further configured to:

display, when the disease degree indicating the degree of the myocardial bridge is high, one or both of the first index value and the second index value calculated on a basis of the medical image in an end-diastolic phase; and display, when the disease degree indicating the degree of the myocardial bridge is low, one or both of the first index value and the second index value calculated on a basis of the medical image in an end-diastolic phase and the medical image in an end-systolic phase.

Note 21:

The extracting unit may be further configured to extract a degree of a valvular disease of each of valves included in heart valves, as the degree of the disease related to the heart, and the display controlling unit is further configured to:

display, when the disease degree indicating the degree of the valvular disease of an aortic valve is high, one or both of the first index value and the second index value calculated on a basis of the medical image in an end-systolic phase; and display, when the disease degree indicating the degree of the valvular disease of a mitral valve is low, one or both of the first index value and the second index value calculated on a basis of the medical image in an end-diastolic phase.

Note 22:

The display controlling unit may be further configured to display, when the degree of the disease related to the heart is low, a graph having a vertical axis that expresses magnitude of the wall shear stress and a horizontal axis that expresses distance from a reference position along the blood vessel and thereby indicating a relation between the magnitude of the wall shear stress and the distance, and further display, together with the graph, information indicating a range of the distance in which a third index value related to the blood vessel exhibits abnormal values.

Note 23:

The display controlling unit may be further configured to display, when the degree of the disease related to the heart is low, with respect to each of a plurality of mutually-different points in time, a graph having a vertical axis that expresses magnitude of the wall shear stress and a horizontal axis that expresses distance from a reference position along the blood vessel and thereby indicating a relation between the magnitude of the wall shear stress and the distance.

Note 24:

The display controlling unit may be further configured to display, together with the graph, information indicating a range of the distance in which temporal fluctuation amounts of the wall shear stress exceed a threshold value.

Note 25:

The display controlling unit may be further configured to display, together with the graph, information indicating a range of the distance in which a third index value related to the blood vessel exhibits abnormal values.

Note 26:

The display controlling unit may be further configured to displays the information indicating the range of the distance in which the third index value exhibits the abnormal values, so as to be superimposed on the graph, by aligning positions in the distance direction.

Note 27:

The third index value may be one of: an index value representing a lesion part occurring in the blood vessel; an index value calculated from a change in blood pressure, a blood flow, a shape, or a position of the blood vessel; and an index value predicted by applying virtual surgery or treatment to the blood vessel while using the medical image.

Note 28:

A medical image processing apparatus including:

a display controlling unit configured to display, as information related to a blood flow of a blood vessel and calculated on the basis of a medical image: a first index value related to the blood vessel and calculated from one of blood pressure and the blood flow; and wall shear stress serving as a second index value related to the blood vessel.

The display controlling unit is further configured to switch the display between the first index value and the second index value on the basis of information about a subject.

Note 29:

A medical image processing system, comprising: a medical image processing apparatus and a medical information display apparatus, wherein the medical image processing apparatus is configured:

to extract a degree of a disease related to the heart from a medical image; and to calculate, when the degree of the disease related to the heart is high, a first index value related to a blood vessel and calculated from one of blood pressure and a blood flow and to calculate, when the degree of the disease related to the heart is low, wall shear stress serving as a second index value related to the blood vessel, as information related to the blood flow of the blood vessel and calculated on the basis of the medical image, whereas the medical information display apparatus is configured to obtain, from the medical image processing apparatus, and to display the information related to the blood flow of the blood vessel.

Note 30:

A medical image processing method, comprising:

extracting a degree of a disease related to the heart from a medical image; and displaying, when the degree of the disease related to the heart is high, a first index value related to a blood vessel and calculated from one of blood pressure and a blood flow and displaying, when the degree of the disease related to the heart is low, wall shear stress serving as a second index value related to the blood vessel, as information related to the blood flow of the blood vessel and calculated on the basis of the medical image.

What is claimed is:

1. A medical image processing apparatus, comprising:
processing circuitry configured to
extract a degree of a disease related to a heart from a medical image; and
display, when the degree of the disease related to the heart is high, a first index value related to a blood vessel and calculated from one of blood pressure and a blood flow, and display, when the degree of the disease related to the heart is low, wall shear stress serving as a second index value related to the blood vessel, as information related to the blood flow of the blood vessel and calculated based on the medical image, wherein the first index value is an index value of a different type from the wall shear stress serving as the second index value.

2. The medical image processing apparatus according to claim 1, wherein the processing circuitry is further configured to:
   display, when a disease degree indicating the degree of the disease related to the heart is higher than a first threshold value, the first index value;
   display, when the disease degree indicating the degree of the disease related to the heart is lower than a second threshold value smaller than the first threshold value, the second index value; and
   display, when the disease degree indicating the degree of the disease related to the heart falls between the first threshold value and the second threshold value, the first index value and the second index value.

3. The medical image processing apparatus according to claim 1, wherein the processing circuitry is further configured to:
   display, when the disease degree indicating the degree of the disease related to the heart is high, one or both of the first index value being one-dimensional and the second index value being one-dimensional; and
   display, when the disease degree indicating the degree of the disease related to the heart is low, one or both of the first index value being three-dimensional and the second index value being three-dimensional.

4. The medical image processing apparatus according to claim 1, wherein the processing circuitry is further configured to:
   simultaneously display the first index value and the second index value;
   make, when the disease degree indicating the degree of the disease related to the heart is high, a display region of the first index value larger than a display region of the second index value; and
   make, when the disease degree indicating the degree of the disease related to the heart is low, the display region of the second index value larger than the display region of the first index value.

5. The medical image processing apparatus according to claim 1, wherein the processing circuitry is further configured to display the first index value and the second index value in mutually-different display modes.

6. The medical image processing apparatus according to claim 1, wherein the processing circuitry is further configured to display an image indicating the blood vessel, and display, within the image, the first index value and the second index value arranged on top of each other or side by side.

7. The medical image processing apparatus according to claim 1, wherein the processing circuitry is further configured to:
   receive, from a user, an operation to select a type of information to be displayed; and
   display one or both of the first index value and the second index value in accordance with the received operation.

8. The medical image processing apparatus according to claim 1, wherein the processing circuitry is further configured to:
   receive, from the user, an operation to switch display between the first index value and the second index value; and
   switch from a state in which one of the first index value and the second index value is displayed into a state in which the other is displayed in accordance with the received operation.

9. The medical image processing apparatus according to claim 1, wherein the processing circuitry is further configured to:
   identify whether a time at which the medical image was taken was before a subject was treated or after the subject was treated;
   calculate, when the time at which the medical image was taken is identified as before the subject was treated, one or both of a first predicted index value being the first index value after the treatment and a second predicted index value being the second index value after the treatment, by applying virtual treatment to the blood vessel while using the medical image; and
   display, when the time at which the medical image was taken is identified as before the subject was treated, one or both of the first predicted index value and the second predicted index value.

10. The medical image processing apparatus according to claim 9, wherein the processing circuitry is further configured to:
    display, when the time at which the medical image was taken is identified as before the subject was treated, one or both of the first index value and the second index value calculated based on the medical image and one or both of the first predicted index value and the second predicted index value; and
    display, when the time at which the medical image was taken is identified as after the subject was treated, one or both of the first index value and the second index value calculated based on the medical image.

11. The medical image processing apparatus according to claim 9, wherein the processing circuitry is further configured to:
    display, when the time at which the medical image was taken is identified as before the subject was treated, one or both of the first index value being three-dimensional and the second index value being three-dimensional; and
    display, when the time at which the medical image was taken is identified as after the subject was treated, one or both of the first index value being one-dimensional and the second index value being one-dimensional.

12. The medical image processing apparatus according to claim 9, wherein the processing circuitry is further configured to calculate, after determining to display one or both of the first predicted index value and the second predicted index value, the one or both of the first predicted index value and the second predicted index value.

13. The medical image processing apparatus according to claim 9, wherein the processing circuitry is further configured to:
    receive, from the user, an operation to input a parameter used at a time of applying the virtual treatment; and
    calculate one or both of the first predicted index value and the second predicted index value by using the received parameter.

14. The medical image processing apparatus according to claim 9, wherein the processing circuitry is further configured to display, when the time at which the medical image was taken is identified as after the subject was treated, one or both of the first index value and the second index value calculated based on the medical image before the treatment and one or both of the first index value and the second index value calculated based on the medical image after the treatment.

15. The medical image processing apparatus according to claim 1, wherein the processing circuitry is further configured to:
derive, with respect to each of blood vessel branches of a coronary artery, a position and a rupture probability of plaque occurring at the blood vessel branch, based on the medical image; and
display, with respect to each of the blood vessel branches, one of the first index value and the second index value in accordance with the position and the rupture probability of the plaque.

16. The medical image processing apparatus according to claim 15, wherein the processing circuitry is further configured to:
display the first index value with respect to any of the blood vessel branches having the plaque of which the rupture probability is high; and
display the second index value with respect to any of the blood vessel branches having no plaque or having the plaque of which the rupture probability is low.

17. The medical image processing apparatus according to claim 15, wherein the processing circuitry is further configured to:
display, with respect to any of the blood vessel branches having the plaque of which the rupture probability is high, a first representative value for one of the first index value and the second index value of the blood vessel branch; and
display, with respect to any of the blood vessel branches having no plaque and any of the blood vessel branches having the plaque of which the rupture probability is low, a second representative value different from the first representative value, for one of the first index value and the second index value of the blood vessel branch.

18. The medical image processing apparatus according to claim 15, wherein the processing circuitry is further configured to:
display, with respect to any of the blood vessel branches having the plaque of which the rupture probability is high, one of a medical image taken by a first medical image diagnosis apparatus and information obtained from the taken medical image; and
display, with respect to any of the blood vessel branches having no plaque and any of the blood vessel branches having the plaque of which the rupture probability is low, one of a medical image taken by a second medical image diagnosis apparatus different from the first medical image diagnosis apparatus and information obtained from the taken medical image.

19. The medical image processing apparatus according to claim 1, wherein the processing circuitry is further configured to display one or both of the first index value and the second index value calculated based on the medical image that is in a specific cardiac phase and is reconstructed in accordance with the degree of the disease related to the heart.

20. The medical image processing apparatus according to claim 19, wherein the processing circuitry is further configured to:
extract a degree of a myocardial bridge, as the degree of the disease related to the heart;
display, when the disease degree indicating the degree of the myocardial bridge is high, one or both of the first index value and the second index value calculated based on the medical image in an end-diastolic phase; and
display, when the disease degree indicating the degree of the myocardial bridge is low, one or both of the first index value and the second index value calculated based on the medical image in an end-diastolic phase and the medical image in an end-systolic phase.

21. The medical image processing apparatus according to claim 19, wherein the processing circuitry is further configured to:
extract a degree of a valvular disease of each of valves included in heart valves, as the degree of the disease related to the heart;
display, when the disease degree indicating the degree of the valvular disease of an aortic valve is high, one or both of the first index value and the second index value calculated based on the medical image in an end-systolic phase; and
display, when the disease degree indicating the degree of the valvular disease of a mitral valve is low, one or both of the first index value and the second index value calculated based on the medical image in an end-diastolic phase.

22. The medical image processing apparatus according to claim 1, wherein the processing circuitry is further configured to display, when the degree of the disease related to the heart is low, a graph having a vertical axis that expresses magnitude of the wall shear stress and a horizontal axis that expresses distance from a reference position along the blood vessel and thereby indicating a relation between the magnitude of the wall shear stress and the distance, and further display, together with the graph, information indicating a range of the distance in which a third index value related to the blood vessel exhibits abnormal values.

23. The medical image processing apparatus according to claim 1, wherein the processing circuitry is further configured to display, when the degree of the disease related to the heart is low, with respect to each of a plurality of mutually-different points in time, a graph having a vertical axis that expresses magnitude of the wall shear stress and a horizontal axis that expresses distance from a reference position along the blood vessel and thereby indicating a relation between the magnitude of the wall shear stress and the distance.

24. The medical image processing apparatus according to claim 23, wherein the processing circuitry is further configured to display, together with the graph, information indicating a range of the distance in which temporal fluctuation amounts of the wall shear stress exceed a threshold value.

25. The medical image processing apparatus according to claim 23, wherein the processing circuitry is further configured to display, together with the graph, information indicating a range of the distance in which a third index value related to the blood vessel exhibits abnormal values.

26. The medical image processing apparatus according to claim 22, wherein the processing circuitry is further configured to display the information indicating the range of the distance in which the third index value exhibits the abnormal values, so as to be superimposed on the graph, by aligning positions in the distance direction.

27. The medical image processing apparatus according to claim 22, wherein the third index value is one of: an index value representing a lesion part occurring in the blood vessel; an index value calculated from a change in blood pressure, a blood flow, a shape, or a position of the blood vessel; and an index value predicted by applying virtual surgery or treatment to the blood vessel while using the medical image.

28. A medical image processing apparatus, comprising:
processing circuitry configured to display, as information related to a blood flow of a blood vessel and calculated based on a medical image: a first index value related to the blood vessel and calculated from one of blood pressure and the blood flow, and wall shear stress serving as a second index value related to the blood vessel, wherein the first index value is an index value of a different type from the wall shear stress serving as the second index value,
wherein the processing circuitry is further configured to switch the display between the first index value and the second index value based on information about a subject.

29. A medical image processing system, comprising:
a medical image processing apparatus; and
a medical information display apparatus, wherein
the medical image processing apparatus is configured to
extract a degree of a disease related to a heart from a medical image; and
calculate, when the degree of the disease related to the heart is high, a first index value related to a blood vessel and calculated from one of blood pressure and a blood flow and to calculate, when the degree of the disease related to the heart is low, wall shear stress serving as a second index value related to the blood vessel, as information related to the blood flow of the blood vessel and calculated based on the medical image, wherein the first index value is an index value of a different type from the wall shear stress serving as the second index value, and
the medical information display apparatus is configured to obtain, from the medical image processing apparatus, the information related to the blood flow of the blood vessel, and display the information related to the blood flow of the blood vessel.

30. A medical image processing method, comprising:
extracting a degree of a disease related to a heart from a medical image; and
displaying, when the degree of the disease related to the heart is high, a first index value related to a blood vessel and calculated from one of blood pressure and a blood flow, and displaying, when the degree of the disease related to the heart is low, wall shear stress serving as a second index value related to the blood vessel, as information related to the blood flow of the blood vessel and calculated based on the medical image, wherein the first index value is an index value of a different type from the wall shear stress serving as the second index value.

31. A medical image processing apparatus, comprising:
processing circuitry configured to
extract a degree of a disease related to a heart from a medical image; and
display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated based on the medical image, wherein the processing circuitry is further configured to
simultaneously display the first index value and the second index value;
make, when the disease degree indicating the degree of the disease related to the heart is high, a display region of the first index value larger than a display region of the second index value; and
make, when the disease degree indicating the degree of the disease related to the heart is low, the display region of the second index value larger than the display region of the first index value.

32. A medical image processing apparatus, comprising:
processing circuitry configured to
extract a degree of a disease related to a heart from a medical image; and
display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated based on the medical image, wherein the processing circuitry is further configured to
identify whether a time at which the medical image was taken was before a subject was treated or after the subject was treated;
calculate, when the time at which the medical image was taken is identified as before the subject was treated, one or both of a first predicted index value being the first index value after the treatment and a second predicted index value being the second index value after the treatment, by applying virtual treatment to the blood vessel while using the medical image; and
display, when the time at which the medical image was taken is identified as before the subject was treated, one or both of the first predicted index value and the second predicted index value.

33. A medical image processing apparatus, comprising:
processing circuitry configured to
extract a degree of a disease related to a heart from a medical image; and
display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated based on the medical image, wherein the processing circuitry is further configured to
derive, with respect to each of blood vessel branches of a coronary artery, a position and a rupture probability of plaque occurring at the blood vessel branch, based on the medical image; and
display, with respect to each of the blood vessel branches, one of the first index value and the second index value in accordance with the position and the rupture probability of the plaque, and
wherein the processing circuitry is further configured to
display the first index value with respect to any of the blood vessel branches having the plaque of which the rupture probability is high; and display the second index value with respect to any of the blood vessel branches having no plaque or having the plaque of which the rupture probability is low.

34. A medical image processing apparatus, comprising: processing circuitry configured to
    extract a degree of a disease related to a heart from a medical image; and
    display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated based on the medical image,
    wherein the processing circuitry is further configured to derive, with respect to each of blood vessel branches of a coronary artery, a position and a rupture probability of plaque occurring at the blood vessel branch, based on the medical image; and
    display, with respect to each of the blood vessel branches, one of the first index value and the second index value in accordance with the position and the rupture probability of the plaque, and
    wherein the processing circuitry is further configured to display, with respect to any of the blood vessel branches having the plaque of which the rupture probability is high, a first representative value for one of the first index value and the second index value of the blood vessel branch; and
    display, with respect to any of the blood vessel branches having no plaque and any of the blood vessel branches having the plaque of which the rupture probability is low, a second representative value different from the first representative value, for one of the first index value and the second index value of the blood vessel branch.

35. A medical image processing apparatus, comprising: processing circuitry configured to
    extract a degree of a disease related to a heart from a medical image; and
    display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated based on the medical image,
    wherein the processing circuitry is further configured to derive, with respect to each of blood vessel branches of a coronary artery, a position and a rupture probability of plaque occurring at the blood vessel branch, based on the medical image; and
    display, with respect to each of the blood vessel branches, one of the first index value and the second index value in accordance with the position and the rupture probability of the plaque, and
    wherein the processing circuitry is further configured to display, with respect to any of the blood vessel branches having the plaque of which the rupture probability is high, one of a medical image taken by a first medical image diagnosis apparatus and information obtained from the taken medical image; and
    display, with respect to any of the blood vessel branches having no plaque and any of the blood vessel branches having the plaque of which the rupture probability is low, one of a medical image taken by a second medical image diagnosis apparatus different from the first medical image diagnosis apparatus and information obtained from the taken medical image.

36. A medical image processing apparatus, comprising: processing circuitry configured to
    extract a degree of a disease related to a heart from a medical image; and
    display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated based on the medical image,
    wherein the processing circuitry is further configured to display one or both of the first index value and the second index value calculated on a basis of the medical image that is in a specific cardiac phase, and is reconstructed in accordance with the degree of the disease related to the heart, and
    wherein the processing circuitry is further configured to extract a degree of a myocardial bridge, as the degree of the disease related to the heart;
    display, when the disease degree indicating the degree of the myocardial bridge is high, one or both of the first index value and the second index value calculated based on the medical image in an end-diastolic phase; and
    display, when the disease degree indicating the degree of the myocardial bridge is low, one or both of the first index value and the second index value calculated based on the medical image in an end-diastolic phase and the medical image in an end-systolic phase.

37. A medical image processing apparatus, comprising: processing circuitry configured to
    extract a degree of a disease related to a heart from a medical image; and
    display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated based on the medical image,
    wherein the processing circuitry is further configured to display one or both of the first index value and the second index value calculated based on the medical image that is in a specific cardiac phase and is reconstructed in accordance with the degree of the disease related to the heart, and
    wherein the processing circuitry is further configured to extract a degree of a valvular disease of each of valves included in heart valves, as the degree of the disease related to the heart;
    display, when the disease degree indicating the degree of the valvular disease of an aortic valve is high, one or both of the first index value and the second index value calculated on a basis of the medical image in an end-systolic phase; and display, when the disease degree indicating the degree of the valvular disease of a mitral valve is low, one or both of the first index value and the second index value calculated on a basis of the medical image in an end-diastolic phase.

38. A medical image processing apparatus, comprising: processing circuitry configured to extract a degree of a disease related to a heart from a medical image; and display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated based on the medical image, wherein the processing circuitry is further configured to display, when the degree of the disease related to the heart is low, a graph having a vertical axis that expresses magnitude of the wall shear stress and a horizontal axis that expresses distance from a reference position along the blood vessel and thereby indicating a relation between the magnitude of the wall shear stress and the distance, and further display, together with the graph, information indicating a range of the distance in which a third index value related to the blood vessel exhibits abnormal values.

39. A medical image processing apparatus, comprising: processing circuitry configured to extract a degree of a disease related to a heart from a medical image; and display, when the degree of the disease related to the heart is high, a first index value related to a blood vessel and calculated from one of blood pressure and a blood flow and configured to display, when the degree of the disease related to the heart is low, wall shear stress serving as a second index value related to the blood vessel, as information related to the blood flow of the blood vessel and calculated based on the medical image, wherein the processing circuitry is further configured to display, when the degree of the disease related to the heart is low, with respect to each of a plurality of mutually-different points in time, a graph having a vertical axis that expresses magnitude of the wall shear stress and a horizontal axis that expresses distance from a reference position along the blood vessel and thereby indicating a relation between the magnitude of the wall shear stress and the distance.

* * * * *